United States Patent
Shimizu et al.

(10) Patent No.: US 12,383,136 B2
(45) Date of Patent: Aug. 12, 2025

(54) SLIT LAMP MICROSCOPE

(71) Applicant: Topcon Corporation, Tokyo (JP)

(72) Inventors: Hitoshi Shimizu, Tokyo (JP); Kazuhiro Ohmori, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 965 days.

(21) Appl. No.: 17/435,037

(22) PCT Filed: Mar. 5, 2020

(86) PCT No.: PCT/JP2020/009343
§ 371 (c)(1),
(2) Date: Aug. 31, 2021

(87) PCT Pub. No.: WO2020/189299
PCT Pub. Date: Sep. 24, 2020

(65) Prior Publication Data
US 2022/0133144 A1    May 5, 2022

(30) Foreign Application Priority Data

Mar. 19, 2019 (JP) ................................ 2019-051361
Dec. 25, 2019 (JP) ................................ 2019-234916

(51) Int. Cl.
*A61B 3/135* (2006.01)
*A61B 3/00* (2006.01)
*A61B 3/14* (2006.01)

(52) U.S. Cl.
CPC ............ *A61B 3/135* (2013.01); *A61B 3/0025* (2013.01); *A61B 3/14* (2013.01)

(58) Field of Classification Search
CPC ......... A61B 3/135; A61B 3/0025; A61B 3/14; A61B 3/10; A61B 3/117; A61B 3/1005;
(Continued)

(56) References Cited

U.S. PATENT DOCUMENTS

| | | | | |
|---|---|---|---|---|
| 5,512,965 A | * | 4/1996 | Snook | A61B 3/107 351/212 |
| 2011/0295617 A1 | * | 12/2011 | Berger | G16H 20/40 705/3 |

(Continued)

FOREIGN PATENT DOCUMENTS

| | | |
|---|---|---|
| JP | 2000-197607 A | 7/2000 |
| JP | 2012-93522 A | 5/2012 |

(Continued)

OTHER PUBLICATIONS

Extended European Search Report issued Nov. 23, 2022 in corresponding European Patent Application No. 20773788.3, 4 pages.

(Continued)

*Primary Examiner* — Travis S Fissel
(74) *Attorney, Agent, or Firm* — XSENSUS LLP

(57) ABSTRACT

A slit lamp microscope according to some aspect examples includes an illumination system and photographing system. The illumination system projects slit light onto an anterior segment of a subject's eye. The photographing system includes an optical system and an image sensor. The optical system directs light from the anterior segment onto which the slit light is being projected. The image sensor includes a light detecting surface that receives the light directed by the optical system. Further, a subject plane, a principal plane of the optical system, and the light detecting surface are arranged so as to satisfy a Scheimpflug condition. Here, the subject plane includes a focal point of the illumination system in which a position of the focal point is shifted on account of a refractive index of a tissue of the anterior segment.

11 Claims, 26 Drawing Sheets

(58) Field of Classification Search
CPC ......... A61B 3/101; A61B 3/107; A61B 3/113; A61B 3/13; A61B 3/145; G02B 21/0028; G02B 21/006; G02B 21/362
USPC ....................................................... 351/206
See application file for complete search history.

(56) References Cited

U.S. PATENT DOCUMENTS

| | | | |
|---|---|---|---|
| 2014/0218688 A1* | 8/2014 | Verdooner | A61B 3/024 351/208 |
| 2015/0265148 A1 | 9/2015 | Bajramovic et al. | |
| 2016/0193037 A1 | 7/2016 | Pinto et al. | |
| 2017/0156591 A1 | 6/2017 | Berestka et al. | |
| 2017/0258577 A1 | 9/2017 | Pinto et al. | |
| 2018/0092574 A1* | 4/2018 | Tzvieli | A61B 5/6803 |
| 2019/0053703 A1 | 2/2019 | Berestka et al. | |
| 2019/0076242 A1 | 3/2019 | Pinto | |
| 2020/0085567 A1 | 3/2020 | Pinto et al. | |
| 2020/0214830 A1 | 7/2020 | Pinto et al. | |
| 2020/0315451 A1 | 10/2020 | Berestka et al. | |
| 2021/0093445 A1 | 4/2021 | Pinto et al. | |

FOREIGN PATENT DOCUMENTS

| | | |
|---|---|---|
| JP | 2015-533322 A | 11/2015 |
| JP | 2016-159073 A | 9/2016 |
| JP | 2017-526507 A | 9/2017 |
| JP | 2017-526517 A | 9/2017 |

OTHER PUBLICATIONS

International Search Report and Written Opinion mailed on Apr. 21, 2020, received for PCT Application PCT/JP2020/009343, Filed on Mar. 5, 2020, 8 pages including English Translation.

* cited by examiner

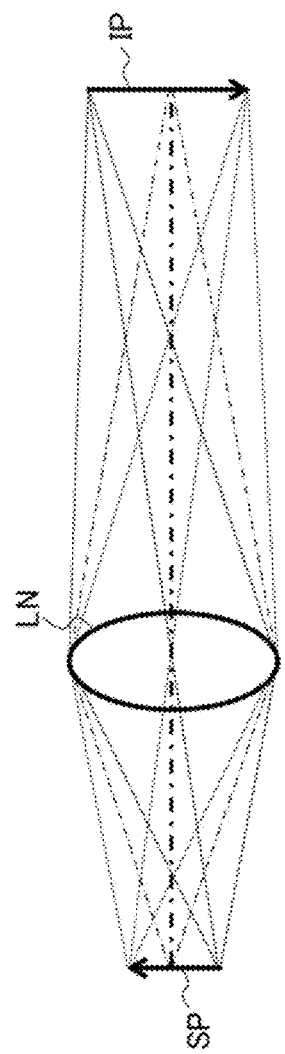

SLIT LAMP MICROSCOPE

FIELD OF THE INVENTION

The present disclosure relates generally to a slit lamp microscope.

BACKGROUND OF THE INVENTION

Diagnostic imaging serves an important role in the field of ophthalmology. Various kinds of ophthalmic imaging apparatuses (modalities) are utilized for diagnostic imaging. Examples of ophthalmic imaging apparatuses include a slit lamp microscope, a fundus camera, a scanning laser ophthalmoscope (SLO), an optical coherence tomography (OCT) apparatus, and the like. In addition, various kinds of ophthalmic examination apparatuses such as a refractometer, a keratometer, a tonometer, a specular microscope, a wave front analyzer, and a microperimeter, are equipped with the function of imaging an anterior eye segment and/or an eye fundus.

A slit lamp microscope is one of the most widely and frequently used modalities among various kinds of ophthalmic apparatuses. A slit lamp microscope is an ophthalmic apparatus for illuminating a subject's eye with slit light and observing and/or photographing (imaging) the illuminated cross section of the subject's eye from an oblique direction with a microscope.

For example, Patent Document 1 below discloses a slit lamp microscope capable of performing anterior segment imaging in parallel with performing a combination of movement of the illumination system and the photographing system and movement of their focal points. Such a conventional technique is capable of acquiring a three dimensional image in focus over a wide area of the anterior segment. However, it takes time and effort to conduct photographing because the conventional technique requires both scanning in the optical axis direction of the optical system and scanning in a direction perpendicular to the optical axis direction, that is, both the movement of the focal points and the movement of the optical systems.

Patent Documents 2 and 3 below disclose techniques for performing anterior segment imaging using the Scheimpflug principle. The Scheimpflug principle is a geometric rule that describes the orientation of the focal plane of the optical system in the case where the lens plane and the image plane are not parallel to one another. The Scheimpflug principle asserts that if the principal plane of the lens (optical system) and the light detecting surface of the image sensor meet at a certain straight line, the subject plane in focus also meets at the same straight line.

According to the Scheimpflug principle, if a slit lamp microscope is configured in such a manner that a plane passing through the optical axis of the illumination system (this plane includes the subject plane), the principal plane of the photographing system, and the light detecting surface of the image sensor meet at a common straight line, then the slit lamp microscope is capable of acquiring an image in focus over the entire subject plane.

According to such a conventional Scheimpflug-type slit lamp microscope, when observing and/or photographing the anterior segment from an oblique direction with respect to the optical axis of the subject's eye, the light beam is refracted by the difference between the refractive indices inside and outside the subject's eye, thereby disordering the optical system arrangement in accordance with the Scheimpflug principle. Furthermore, there are individual differences in the arrangement disorder owing to individual differences in the shapes and characteristics of the eye tissues. For example, individual differences in the corneal shapes (corneal curvatures) and the refractive indices of anterior segment tissues may have influence on the arrangement disorder.

PRIOR ART DOCUMENTS

Patent Documents

[PATENT DOCUMENT 1] Japanese Unexamined Patent Application Publication No. 2016-159073
[PATENT DOCUMENT 2] Japanese Unexamined Patent Application Publication No. 2000-197607
[PATENT DOCUMENT 3] Japanese Unexamined Patent Application Publication (Translation of PCT Application) No. 2015-533322

BRIEF SUMMARY OF THE INVENTION

Problem to be Solved by the Invention

An object of the present disclosure is to solve a problem of Scheimpflug-type slit lamp microscopes caused by the refractive index differences between the inside and outside of the subject's eye.

Means for Solving the Problem

The first aspect example of the present disclosure is a slit lamp microscope comprising: an illumination system configured to project slit light onto an anterior segment of a subject's eye; and a photographing system that includes an optical system and an image sensor, the optical system being configured to direct light from the anterior segment onto which the slit light is being projected to the image sensor, and the image sensor including a light detecting surface and being configured to receive the light directed by the optical system by the light detecting surface, wherein a subject plane, a principal plane of the optical system, and the light detecting surface are arranged so as to satisfy a Scheimpflug condition, the subject plane including a focal point of the illumination system wherein a position of the focal point is shifted on account of a refractive index of a tissue of the anterior segment.

The second aspect example of the present disclosure is the slit lamp microscope of the first aspect, further comprising a movement mechanism configured to move the illumination system and the photographing system, wherein the photographing system is configured to acquire a plurality of images of the anterior segment by repetitively performing photography in parallel with movement of the illumination system and the photographing system by the movement mechanism.

The third aspect example of the present disclosure is the slit lamp microscope of the second aspect, further comprising a three dimensional image constructing processor configured to construct a three dimensional image based on the plurality of images.

The fourth aspect example of the present disclosure is the slit lamp microscope of the third aspect, further comprising a rendering processor configured to construct a rendered image by applying rendering to the three dimensional image.

The fifth aspect example of the present disclosure is the slit lamp microscope of any of the second to fourth aspect examples, further comprising an analyzing processor configured to apply predetermined analysis processing to at least one of the plurality of images or an image generated by processing at least one of the plurality of images.

The sixth aspect example of the present disclosure is the slit lamp microscope of any of the first to fifth aspect examples, wherein a shift angle of the subject plane on account of the refractive index belongs to a range of 3 to 13 degrees.

The seventh aspect example of the present disclosure is the slit lamp microscope of the sixth aspect, wherein the shift angle of the subject plane on account of the refractive index belongs to a range of 6 to 10 degrees.

The eighth aspect example of the present disclosure is the slit lamp microscope of any of the first to seventh aspect examples, wherein a shift angle of the subject plane on account of the refractive index is determined based at least on a value of a corneal curvature radius and a value of an ocular refractive index of a predetermined eye model.

The ninth aspect example of the present disclosure is the slit lamp microscope of any of the first to fifth aspect examples, wherein a shift angle of the subject plane on account of the refractive index is determined based at least on an angle formed by an optical axis of the illumination system and an optical axis of the photographing system.

The tenth aspect example of the present disclosure is the slit lamp microscope of the ninth aspect, wherein the angle is set to a value greater than 0 degrees and not exceeding 60 degrees.

The eleventh aspect example of the present disclosure is the slit lamp microscope of the ninth or tenth aspect, wherein the shift angle of the subject plane on account of the refractive index is determined based at least on the angle and a corneal curvature radius.

The twelfth aspect example of the present disclosure is the slit lamp microscope of the eleventh aspect, wherein a value of the corneal curvature radius is set based on a predetermined eye model.

The thirteenth aspect example of the present disclosure is the slit lamp microscope of the twelfth aspect, wherein the value of the corneal curvature radius is set to a value belonging to a range of 7.7 mm±0.5 mm according to a Gullstrand eye model.

The fourteenth aspect example of the present disclosure is the slit lamp microscope of the ninth or tenth aspect, wherein the shift angle of the subject plane on account of the refractive index is determined based at least on the angle and an ocular refractive index.

The fifteenth aspect example of the present disclosure is the slit lamp microscope of the fourteenth aspect, wherein a value of the ocular refractive index is set based on a predetermined eye model.

The sixteenth aspect example of the present disclosure is the slit lamp microscope of the fifteenth aspect, wherein the value of the ocular refractive index is set to a value belonging to a range of 1.336±0.001 according to a Gullstrand eye model.

The seventeenth aspect example of the present disclosure is the slit lamp microscope of the ninth or tenth aspect, wherein the shift angle of the subject plane on account of the refractive index is determined based at least on the angle, a corneal curvature radius, and an ocular refractive index.

The eighteenth aspect example of the present disclosure is the slit lamp microscope of the seventeenth aspect, wherein each of a value of the corneal curvature radius and a value of the ocular refractive index is set based on a predetermined eye model.

The nineteenth aspect example of the present disclosure is the slit lamp microscope of the eighteenth aspect, wherein according to a Gullstrand eye model, the value of the corneal curvature radius is set to a value belonging to a range of 7.7 mm±0.5 mm, and the value of the ocular refractive index is set to a value belonging to a range of 1.336±0.001.

The twentieth aspect example of the present disclosure is the slit lamp microscope of the nineteenth aspect, wherein the shift angle is set to a value greater than 0 degrees and not exceeding 11.09 degrees.

The twenty first aspect example of the present disclosure is the slit lamp microscope of any of the first to twentieth aspect examples, further comprising a first orientation changing mechanism configured to change an orientation of an optical axis of the photographing system.

The twenty second aspect example of the present disclosure is the slit lamp microscope of the twenty first aspect, wherein the first orientation changing mechanism is configured to turn the optical axis of the photographing system substantially about an intersection of the subject plane and the optical axis of the photographing system.

The twenty third aspect example of the present disclosure is the slit lamp microscope of the twenty first or twenty second aspect, further comprising: an image quality evaluating processor configured to evaluate image quality by analyzing an image of the subject's eye acquired by the photographing system; and a first orientation changing controller configured to control the first orientation changing mechanism based at least on a result of evaluation performed by the image quality evaluating processor.

The twenty fourth aspect example of the present disclosure is the slit lamp microscope of any of the twenty first to twenty third aspect examples, further comprising: a measuring processor configured to measure a corneal curvature radius by analyzing an image of the subject's eye acquired by the photographing system; and a first determining processor configured to determine a target orientation of the optical axis of the photographing system based at least on a result of measurement performed by the measuring processor, wherein the first orientation changing mechanism is configured to change the orientation of the optical axis of the photographing system to the target orientation.

The twenty fifth aspect example of the present disclosure is the slit lamp microscope of any of the twenty first to twenty third aspect examples, further comprising: a data receiver configured to receive measurement data of a corneal curvature radius of the subject's eye acquired in advance; and a second determining processor configured to determine a target orientation of the optical axis of the photographing system based at least on the measurement data, wherein the first orientation changing mechanism is configured to change the orientation of the optical axis of the photographing system to the target orientation.

The twenty sixth aspect example of the present disclosure is the slit lamp microscope of any of the twenty first to twenty fifth aspect examples, wherein the photographing system is configured to start photography of the anterior segment in response to a change of the orientation of the optical axis of the photographing system made by the first orientation changing mechanism.

The twenty seventh aspect example of the present disclosure is the slit lamp microscope of any of the first to twentieth aspect examples, further comprising a second orientation changing mechanism configured to change an orientation of an optical axis of the illumination system.

The twenty eighth aspect example of the present disclosure is the slit lamp microscope of the twenty seventh aspect, wherein the second orientation changing mechanism is configured to turn the optical axis of the illumination system substantially about an intersection of a cornea of the subject's eye and the optical axis of the illumination system.

The twenty ninth aspect example of the present disclosure is the slit lamp microscope of the twenty seventh or twenty eighth aspect, further comprising: an image quality evaluating processor configured to evaluate image quality by analyzing an image of the subject's eye acquired by the photographing system; and a second orientation changing controller configured to control the second orientation changing mechanism based at least on a result of an evaluation performed by the image quality evaluating processor.

The thirtieth aspect example of the present disclosure is the slit lamp microscope of any of the twenty seventh to twenty ninth aspect examples, further comprising: a measuring processor configured to measure a corneal curvature radius by analyzing an image of the subject's eye acquired by the photographing system; and a third determining processor configured to determine a target orientation of the optical axis of the illumination system based at least on a result of measurement performed by the measuring processor, wherein the second orientation changing mechanism is configured to change the orientation of the optical axis of the illumination system to the target orientation.

The thirty first aspect example of the present disclosure is the slit lamp microscope of any of the twenty seventh to twenty ninth aspect examples, further comprising: a data receiver configured to receive measurement data of a corneal curvature radius of the subject's eye acquired in advance; and a fourth determining processor configured to determine a target orientation of the optical axis of the illumination system based at least on the measurement data, wherein the second orientation changing mechanism is configured to change the orientation of the optical axis of the illumination system to the target orientation.

The thirty second aspect example of the present disclosure is the slit lamp microscope of any of the twenty seventh to thirty first aspect examples, wherein the photographing system is configured to start photography of the anterior segment in response to a change of the orientation of the optical axis of the illumination system made by the second orientation changing mechanism.

Effect of the Invention

According to some aspect examples, it becomes possible to avoid a deviation from the Scheimpflug condition caused by the refractive index difference between the inside and outside of the subject's eye.

BRIEF DESCRIPTION OF THE SEVERAL VIEWS OF THE DRAWING

FIG. 1A is a schematic diagram for describing the background of the embodiment examples.

DETAILED DESCRIPTION OF THE INVENTION

Figure 1B:
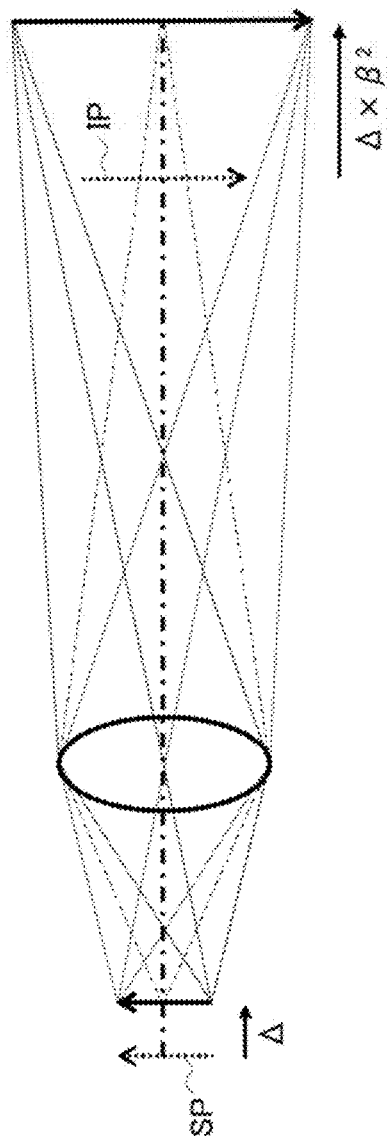
FIG. 1B is a schematic diagram for describing the background of the embodiment examples.

Some embodiment examples will be described in detail with referring to the drawings. It should be noted that any of the matters and items disclosed in the documents cited herein and any known techniques or technology may be combined with any of the embodiment examples. Hereinafter, the background and the outline of the embodiment examples will be briefly described first, and then some aspect examples will be described.

<Background and Outline>

As shown in FIG. 1A, it is known that the subject plane SP, in which the focal point of the lens LN is located, is imaged as the image plane IP at a position calculated from the position with respect to the lens LN and the focal length of the lens LN (Newton's formula). Further, as shown in FIG. 1B, it is also known that when the position of the subject plane SP is shifted by the distance $\Delta$ in a certain direction, the position of the image plane IP also shifts in the same direction by the distance of the product ($\Delta \times \beta^2$) of the square of the lateral magnification $\beta$ of the optical system (that is, the longitudinal magnification) and the distance $\Delta$.

Figure 1C:
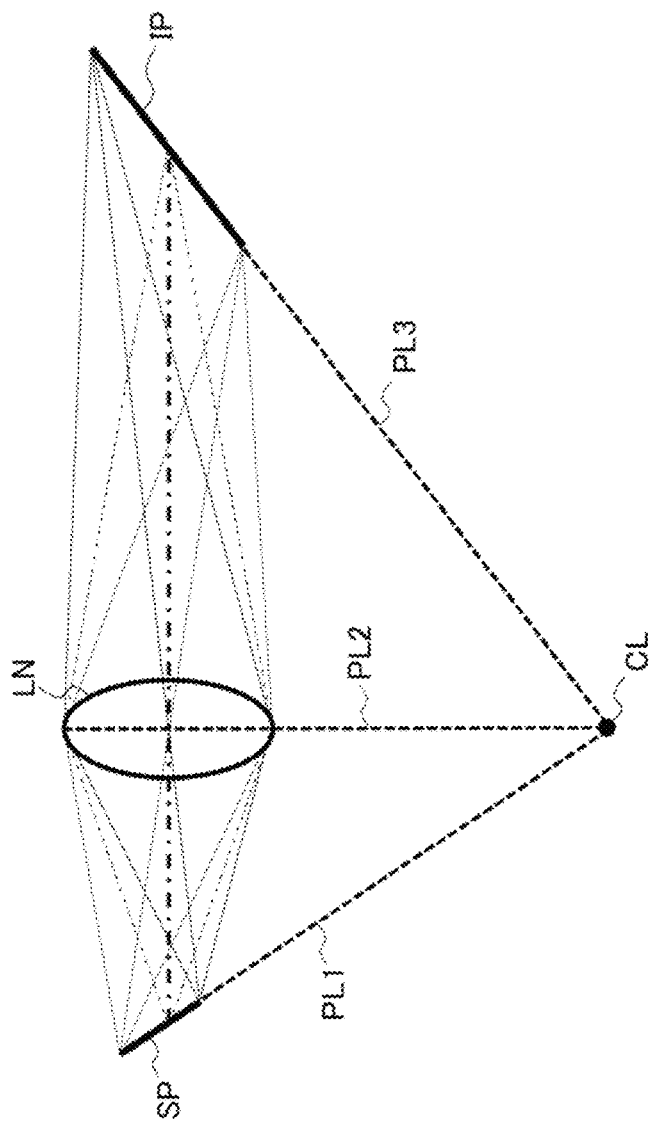
FIG. 1C is a schematic diagram for describing the background of the embodiment examples.

Considering the case where the subject plane SP is tilted with respect to the optical axis of the lens LN, based on the Newton's formula for the case in which the positional shift of the subject plane is taken into account, the Scheimpflug principle asserts, as shown in FIG. 1C, that the plane PL1 including the subject plane SP, the principal plane PL2 of the lens LN, and the plane PL3 including the image plane IP all intersect on the same straight line CL.

Figure 1D:
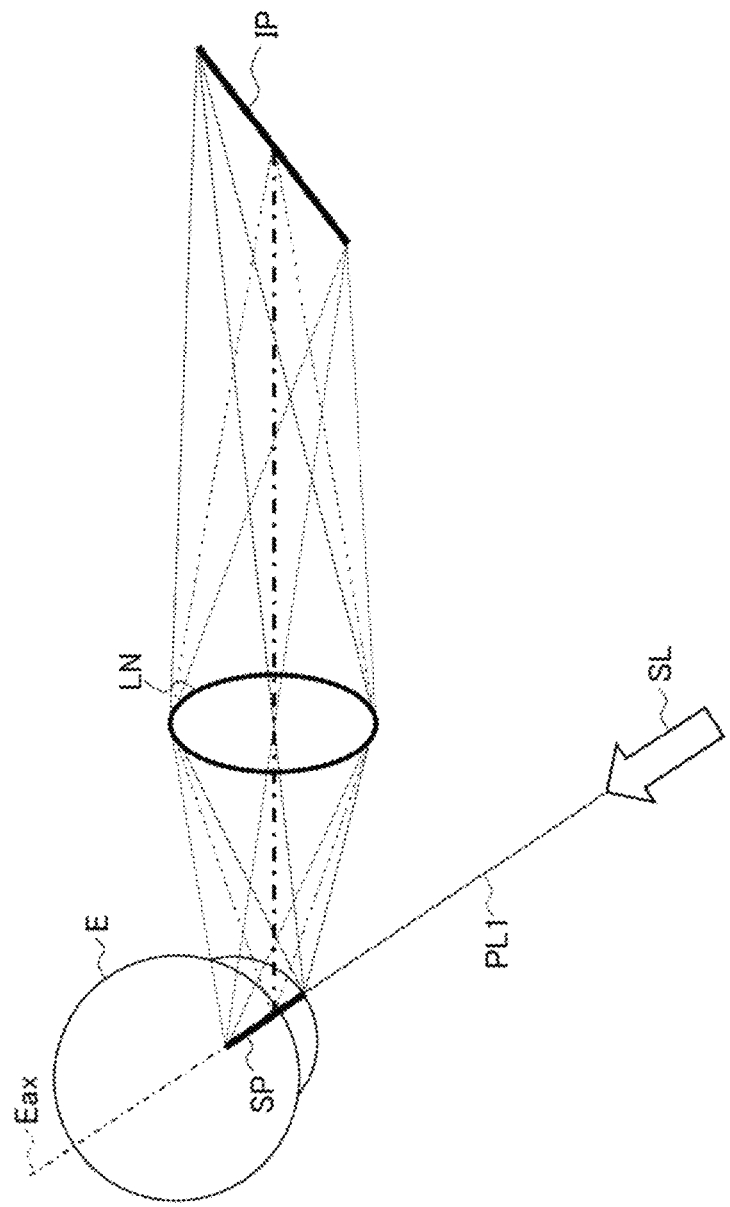
FIG. 1D is a schematic diagram for describing the background of the embodiment examples.

Therefore, in the event that the condition shown in FIG. 1C is met, a slit lamp microscope, which is capable of performing photography with the entire subject plane SP in focus, is realized in theory by matching the ocular optical axis Eax of the subject's eye E and the subject plane SP, as shown in FIG. 1D, that is, by making the slit light SL be incident on the subject's eye E along the plane PL1 that intersects with both the principal plane PL2 and the plane PL3 the same straight line CL.

However, the slit light SL is refracted due to the difference in the refractive index inside and outside of the subject's eye E such as the difference between the refractive index of air and the refractive index of the cornea, the difference in the refractive indices at the ocular tissue boundary (interface), and the like. Therefore, the subject plane SP is not accurate and the Scheimpflug condition is not satisfied when the refraction of the slit light SL is ignored.

Figure 1E:
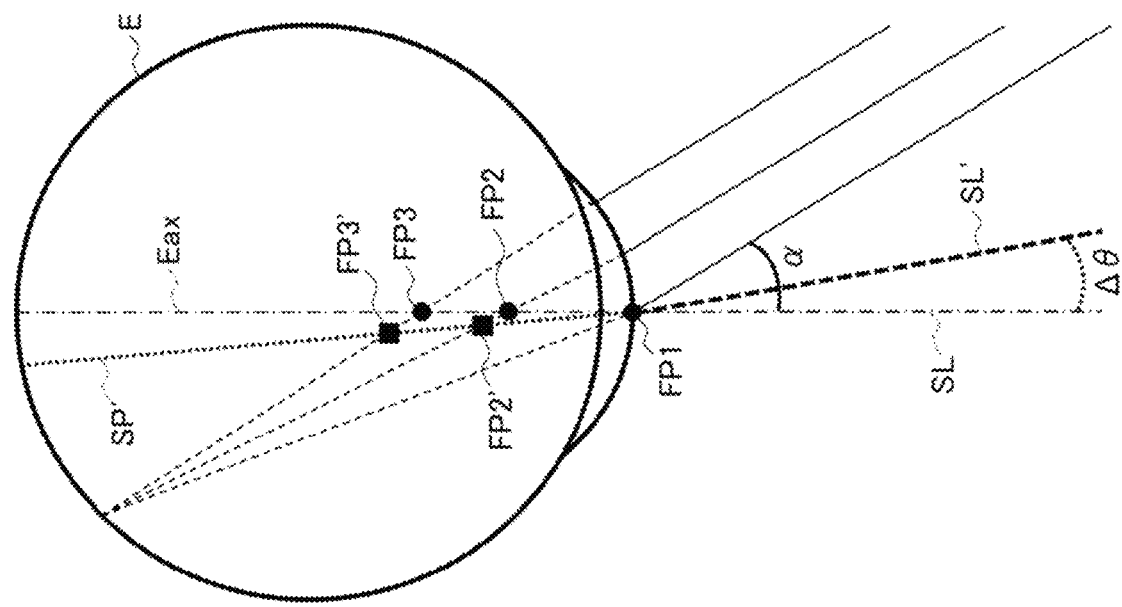
FIG. 1E is a schematic diagram for describing the background of the embodiment examples.

For example, FIG. 1E shows the case where imaging is performed at an angle tilted by the imaging angle $\alpha$ with respect to the incident direction of the slit light SL coincident with the ocular optical axis Eax. Here, the incident direction is also denoted by the reference character SL. In this case, when considering the refraction at the anterior surface of the cornea, the focal point position FP1 of the lens LN located at the corneal apex is not shifted while the (illustrative) focal point positions FP2 and FP3 located inside the subject's eye E are shifted to the positions indicated by the reference characters FP2' and FP3' respectively. Therefore, the subject plane SP' should be employed, rather than the original subject plane SP, as the subject plane that satisfies the Scheimpflug condition. Here, the original subject plane SP coincides with the ocular optical axis Eax, and the subject plane SP' is located on the plane that passes through the plurality of focal point positions FP1, FP2', and FP3' determined by taking into account the effect of refraction.

Furthermore, in order to realize the subject plane SP', considering the angle between the subject plane SP' and the subject plane SP (the ocular optical axis Eax) as well as considering refraction at least at the anterior surface of the cornea, it becomes understood that the slit light should be incident onto the subject's eye E along the direction SL' that is tilted with respect to the original incident direction SL by the angle $\Delta \theta$. As an example of this, suppose that the subject's eye is a sphere, the imaging angle $\alpha$ is 30 degrees. Then, calculation using the corneal curvature radius 7.7 mm and the ocular refractive index 1.336 of the Gullstrand eye model, yields the following results: the tilt angle of the subject plane SP' with respect to the subject plane SP is approximately 6 degrees; and the angle of the incident direction SL' with respect to the incident direction SL is approximately 8 degrees.

Considering the range of individual differences in these parameters and the types of eye models to be referred to, the shift angle $\Delta \theta$ of the subject plane caused by the refractive index of the subject's eye E may belong to the range of 3 to 13 degrees, and further, may belong to the range of 6 to 10 degrees. Any type of eye model may be referred to for determining the shift angle $\Delta \theta$. For example, the type of eye model may be any of the following: the Gullstrand eye model, the Navarro eye model, the Liou-Brennan eye model, the Badal eye model, the Arizona eye model, the Indiana eye model, any standardized eye model, and any eye model equivalent to any of these. Note that various types of eye models are described in Japanese Unexamined Patent Application Publication No. 2012-93522 and Japanese Unexamined Patent Application Publication (Translation of PCT Application) No. 2017-526517, for example.

In the above example, the shift angle $\Delta \theta$ is determined based at least on the value of the corneal curvature radius and the value of the ocular refractive index of an eye model. However, the method of determining the shift angle $\Delta \theta$ is not limited to this. For example, in addition to or instead of the corneal curvature radius, other parameter value(s) may be used to determine the shift angle $\Delta \theta$. Alternatively, information other than an eye model may be used. For example, the shift angle $\Delta \theta$ may be determined using measurement data of the subject's eye E. Some examples of this will be described later.

<On Slit Lamp Microscope>

In general, slit lamp microscopes are widely used in various kinds of medical facilities. The installation locations of the slit lamp microscope according to some embodiments are not limited to medical facilities. The slit lamp microscope according to some embodiments may be used in situations and environments where no technical experts of that apparatus is present nearby, or in situations and environments where a technical expert can provide monitoring, give instructions, and perform operation from a remote place. Further, the slit lamp microscope according to some embodiments may be portable. In addition to medical facilities, examples of the facilities in which the slit lamp microscope according to some embodiments may be installed include optician's stores, optometrist's offices, health facilities, medical institutions, health check and screening venues, patients' homes, welfare facilities, public facilities, medical examination vehicles, and the like.

The slit lamp microscope according to some embodiments is an ophthalmic imaging apparatus (or, more generally, a medical apparatus) having at least the function for observation and photography using slit light (slit lamp microscope function). The slit lamp microscope according to some embodiments may be further provided with other photographing functions (other modalities). Examples of such modalities include a fundus camera, an SLO, an OCT, and the like.

The slit lamp microscope according to some embodiments may further have a function of measuring a characteristic of the subject's eye. Examples of such measurements include visual acuity measurement, refraction measurement, intraocular pressure measurement, corneal endothelial cell measurement, aberration measurement, visual field measurement, and the like.

The slit lamp microscope according to some embodiments may further include application software for analyzing photographed images, measurement data, or the like. In addition, the slit lamp microscope according to some embodiments may further include a function for treatment or surgery. Photocoagulation treatment and photodynamic therapy are examples of such treatment and surgery.

Hereinafter, several aspect examples of some embodiments will be described. Any two or more of the aspect examples may be combined. Further, any known technology or technique may be combined with any one of the aspect examples or with any combination of two or more of the aspect examples. Furthermore, any modifications, such as additions, substitutions, or replacements, based on any known technology or technique may be applied to any one of the aspect examples or to any combination of two or more of the aspect examples.

Note that, in the embodiment examples described below, a "processor" may be a circuit such as a central processing unit (CPU), a graphics processing unit (GPU), an application specific integrated circuit (ASIC), or a programmable logic device (PLD). Examples of the PLD include a simple programmable logic device (SPLD), a complex programmable logic device (CPLD), and a field programmable gate array (FPGA). For example, the processor loads and executes a program and/or data stored in a memory circuit or a storage device, to implement the functions according to the embodiment examples.

The configuration of the slit lamp microscope according to some aspect examples will now be described. First, the directions are defined in the following manner. Suppose that the optical system of the slit lamp microscope is placed in front of the subject's eye (i.e., the neutral position). Then, the front direction (or, the depth direction or the Z direction) is defined as the direction towards the subject's eye from the lens positioned closest to the subject's eye (e.g., an objective lens) in the optical system, and the back direction (the −Z direction) is defined as the opposite direction of the front direction. Further, the lateral direction (or, the left and right direction or the ±X direction) is defined as the horizontal direction orthogonal to the Z direction. In addition, the vertical direction (or, the up and down direction or the ±Y direction) is defined as the direction orthogonal to both the Z direction and the X direction. The XYZ coordinate system is, for example, a three dimensional orthogonal coordinate system (also called a three dimensional Cartesian coordinate system) defined as right-handed coordinates or left-handed coordinates.

Further, the observation and photographing system of the slit lamp microscope can be turned (can be rotated, can pivot) at least in the horizontal direction. The $r_1$ direction is the radial direction that is the direction along the optical axis of the observation and photographing system (the observation and photographing optical axis), and the $\theta_1$ direction is the rotational direction (the angular direction, turning direction). Similarly, the illumination system of the slit lamp microscope can be turned. The $r_2$ direction is the radial direction that is the direction along the optical axis of the illumination system (the illumination optical axis), and the $\theta_2$ direction is the rotational direction (the angular direction). For example, the positive (or forward) direction of the radial direction is the direction from the objective lens toward the subject's eye, and the positive direction of the rotational direction is the counterclockwise direction when viewed from above. For example, the rotational direction is defined on the basis of the Z direction. This means that the Z direction is defined as a rotation angle of 0 degrees. In the state where the observation and photographing system is located at the neutral position, that is, in the state where $\theta_1=0$ degrees, the $r_1$ direction coincides with the Z direction. Similarly, in the state where the illumination system is located at the neutral position, that is, in the state where $\theta_2=0$ degrees, the $r_2$ direction coincides with the Z direction. At least one of the illumination system and the observation and photographing system can be turned in the vertical direction. If this is the case, the radial direction and the rotational direction for the vertical turn can be defined in a similar manner to those for the lateral turn described above.

Figure 2:
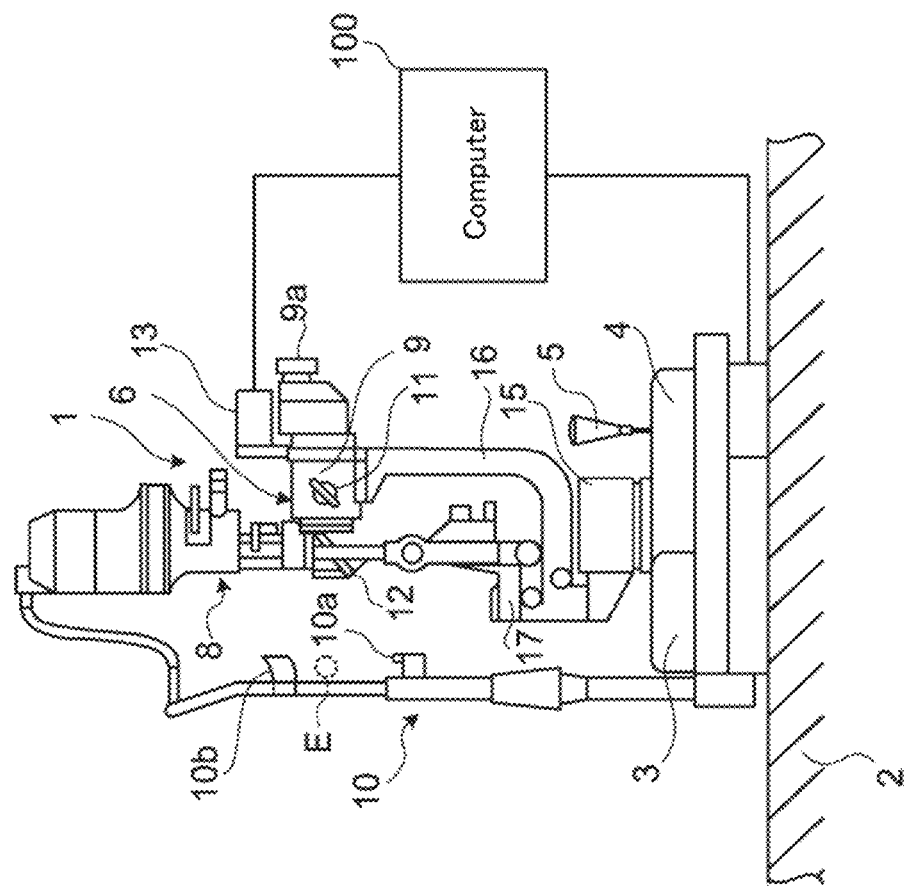
FIG. 2 is a schematic diagram illustrating the configuration of the slit lamp microscope according to the aspect example.

FIG. 2 shows an example of the exterior configuration of the slit lamp microscope according to some aspect examples. The computer 100 is connected to the slit lamp microscope 1. The computer 100 executes various kinds of information processing such as control processing and arithmetic processing. The computer 100 may be connected to the slit lamp microscope 1 via a communication line, and may be a server or the like on a network, for example. Alternatively, the computer 100 may be part of the slit lamp microscope 1.

The slit lamp microscope 1 is placed on the table 2. The base 4 is configured to be movable in three dimensions via the movement mechanism part 3, for example. The base 4 is moved by tilting manipulation of the operation handle 5. Alternatively, the movement mechanism part 3 includes an actuator.

The support portion 15 is provided on the upper surface of the base 4. The support portion 15 is configured to support the observation and photographing system 6 and the illumination system 8. The support arm 16 that supports the observation and photographing system 6 is attached to the support portion 15. The support arm 16 is turnable in the lateral direction. The support arm 17 that supports the illumination system 8 is attached to the upper portion of the support arm 16. The support arm 17 is turnable in the lateral direction. The support arms 16 and 17 are configured to be capable of turning independently of and coaxially with one another.

The observation and photographing system 6 is moved by turning the support arm 16. The illumination system 8 is moved by turning the support arm 17. Each of the support arms 16 and 17 is turned by an electrical mechanism. The movement mechanism part 3 is provided with a mechanism for turning the support arm 16 and a mechanism for turning the support arm 17. The observation and photographing system 6 may be moved by manual turning operation of the support arm 16. Likewise, the illumination system 8 may be moved by manual turning operation of the support arm 17.

The illumination system 8 projects illumination light onto the subject's eye E. As described above, the illumination system 8 may be turned in the lateral direction. Further, the illumination system 8 may be turnable in the vertical direction. In other words, the elevation angle and the depression angle of the illumination system 8 may be changeable. By such swinging (turning, rotating) motions of the illumination system 8, the projection direction of the illumination light with respect to the subject's eye E can be changed.

The observation and photographing system 6 includes a pair of left and right optical systems. Each of the left and the right optical systems is configured to guide return light of the illumination light projected onto the subject's eye E. The left and the right optical systems are stored in the body tube (also called the lens tube or the lens barrel) 9. The terminal end of the body tube 9 is the eyepiece portion 9a. The examiner can observe the subject's eye E by looking into the eyepiece portion 9a. As described above, the body tube 9 can be turned in the lateral direction by turning the support arm 16. In addition, the observation and photographing system 6 may be configured to be turnable in the vertical direction. In other words, the elevation angle and the depression angle of the observation and photographing system 6 may be changeable. By such swinging motions of the observation and photographing system 6, the direction of observing the subject's eye E and the direction of photographing the subject's eye E can be changed.

The chin rest base 10 is disposed at a position facing the body tube 9. The chin rest base 10 is provided with the chin rest 10a and the forehead rest 10b used for stably positioning the subject's face.

The magnification operation knob 11 is disposed on the side surface of the body tube 9. The magnification operation knob 11 is operated to change magnification (enlargement ratio, magnification ratio). Furthermore, the imaging device 13 used for capturing an image of the subject's eye E is attached to the body tube 9. The imaging device 13 includes an image sensor. The image sensor is a photoelectric conversion element configured to detect light and output an image signal (electric signal). The image signal is input to the computer 100. The image sensor may be a CCD image sensor or a CMOS image sensor for example.

The mirror 12 is disposed at the lower position of the illumination system 8. The mirror 12 reflects and redirects the illumination light beam output from the illumination system 8 toward the subject's eye E.

Figure 3:
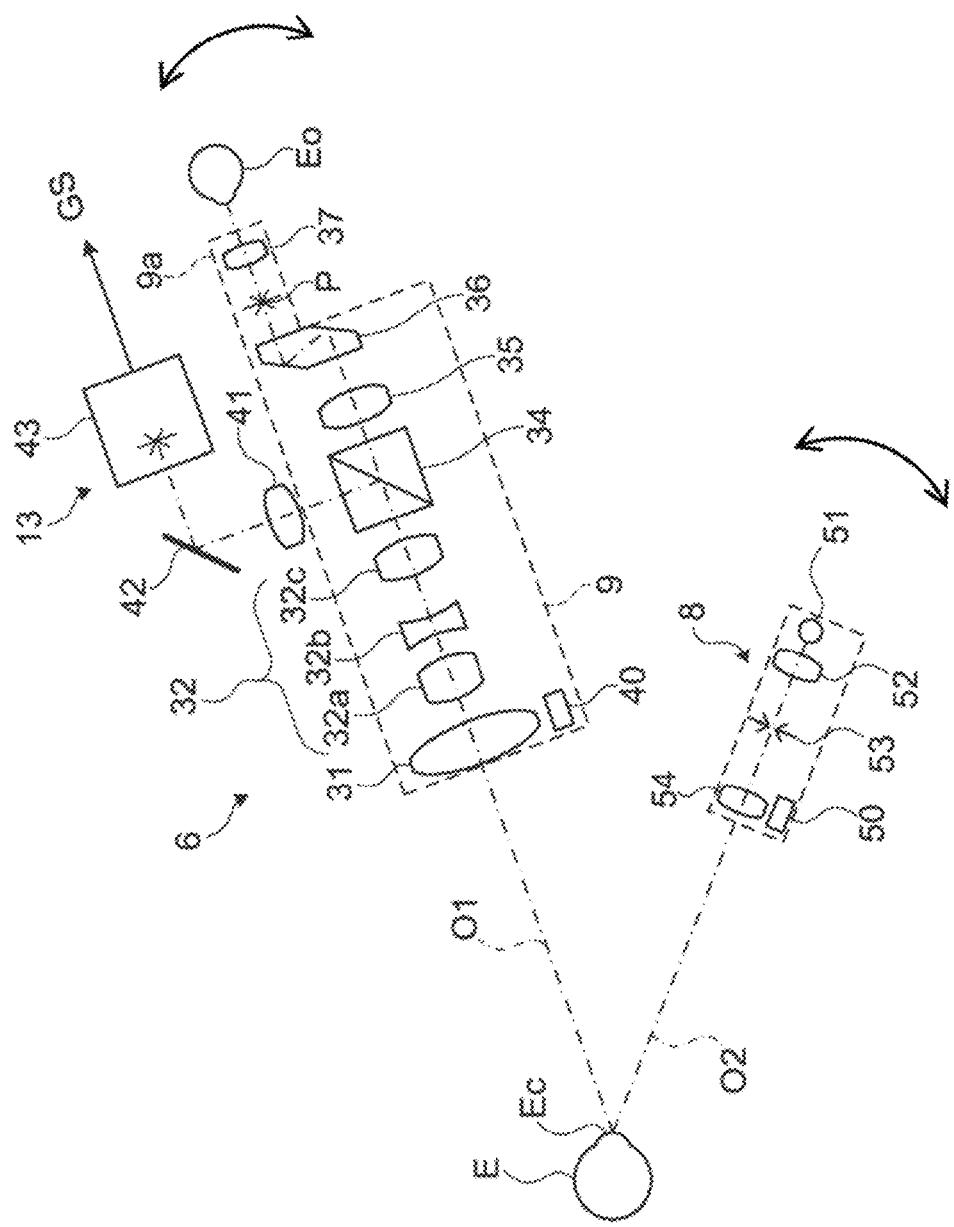
FIG. 3 is a schematic diagram illustrating the configuration of the slit lamp microscope according to the aspect example.

FIG. 3 shows an example of the configuration of the optical systems of the slit lamp microscope 1. As described above, the slit lamp microscope 1 includes the observation and photographing system 6 and the illumination system 8.

The observation and photographing system 6 includes a pair of the left and the right optical systems. The configurations of the left and the right optical systems are almost the same as one another, and allows the examiner to observe the subject's eye E with the examiner's both eyes. Note that FIG. 3 shows only one of the left and the right optical systems of the observation and photographing system 6. The observation and photographing system 6 is not limited to a binocular optical system, and may be a monocular optical system. The reference character O1 denotes the optical axis of the observation and photographing system 6.

Each of the left and the right optical systems of the observation and photographing system 6 includes the objective lens 31, the variable magnification optical system (or the zooming optical system) 32, the beam splitter 34, the imaging lens 35, the prism 36, and the eyepiece 37. Here, the beam splitter 34 is provided in one or both of the left and the right optical systems. The eyepiece 37 is provided inside the eyepiece portion 9a. The reference character P denotes the imaging position of the light guided toward the eyepiece 37. The reference character Ec denotes the cornea of the subject's eye E. The reference character Eo denotes the examiner's eye.

The variable magnification optical system 32 includes a plurality of (e.g., three pieces of) variable magnification lenses 32a, 32b, and 32c. In the present embodiment, a plurality of variable magnification lens groups is prepared and provided. The multiple variable magnification lens groups are selectively inserted into the optical path of the observation and photographing system 6. The multiple variable magnification lens groups corresponds to mutually difference magnifications, respectively. One of the multiple variable magnification lens groups selectively disposed in the optical path of the observation and photographing system 6 is used as the variable magnification optical system 32. The selective insertion of the multiple variable magnification lens groups performed in this way allows the magnification (the angle of view) of photographed images and observation images of the subject's eye E, to be varied. The change in the magnification, that is, the selection from the multiple variable magnification lens groups to be disposed in the optical path of the observation and photographing system 6, can be performed by the operation of the magnification operation knob 11. Some aspect examples may be configured to change the magnification in an electrical way by using a switch (not shown in the drawings) or the like.

The beam splitter 34 splits the optical path of the light traveling along the optical axis O1 into an optical path located on the extension of the optical axis O1 and an optical path orthogonal to the optical axis O1. The light that has entered the optical path located on the extension of the optical axis O1 is guided to the examiner's eye Eo via the imaging lens 35, the prism 36, and the eyepiece 37. The prism 36 translates the traveling direction of the light upward.

On the other hand, the light that has entered the optical path orthogonal to the optical axis O1 is guided to the image sensor 43 of the imaging device 13 via the condenser lens 41 and the mirror 42. In other words, the observation and photographing system 6 can guide the return light from the subject's eye E to the imaging device 13. The image sensor 43 detects the return light and generates the image signal GS. The imaging device 13 is provided in one or both of the left and the right optical systems.

The observation and photographing system 6 includes the focus mechanism 40 for changing the focal position of the observation and photographing system 6. The focus mechanism 40 moves the objective lens 31 in the direction along the optical axis O1. The movement of the objective lens 31 is carried out automatically and/or manually. In the case where automatic movement of the objective lens 31 is employed, for example, the computer 100 may determine the focal position based on the return light from the subject's eye E using a known technique of focus adjustment such as a phase difference detection technique or a contrast detection technique. In addition, the computer 100 may further control the actuator so as to move the objective lens 31 in the direction along the optical axis O1 to the focal position determined. On the other hand, in the case where manual movement of the objective lens 31 is employed, the actuator may be operated to move the objective lens 31 in the direction along the optical axis O1 in accordance with an operation performed by the user.

The observation and photographing system 6 may include the first focusing lens that is disposed at a position on the optical axis O1 between the objective lens 31 and the image sensor 43. In the case where such a first focusing lens is provided, the focus mechanism 40 is configured to change the focal position of the observation and photographing system 6 by moving the first focusing lens along the optical axis O1. Some aspect examples may be configured to move the entire (or, a part of the) observation and photographing system 6 along the optical axis O1. If this is the case, the focus mechanism 40 is configured to vary the focal position of the observation and photographing system 6 by moving the entire (or, the part of the) observation and photographing system 6 in the direction along the optical axis O1. As in the case of moving the objective lens 31, the movement of the first focusing lens or the observation and photographing system 6 induced by the focus mechanism 40 may be carried out automatically or manually.

while the present aspect example employs the observation and photographing system 6 that is capable of performing both observation with an eyepiece and photographing with an image sensor, slit lamp microscopes of some aspect examples may include a photographing system that is capable of performing only photographing with an image sensor.

The illumination system 8 includes the illumination light source 51, the condenser lens 52, the slit forming part 53, and the objective lens 54. The reference character O2 denotes the optical axis of the illumination system 8.

The illumination light source 51 outputs illumination light. The illumination system 8 may include a plurality of light sources. For example, the illumination light source 51 may include both a light source that outputs steady light or continuous light and a light source that outputs flash light. Examples of the light source that outputs steady light or continuous light include a halogen lamp and a light emitting diode (LED). Examples of the light source that outputs flash light include a xenon lamp and an LED. The illumination light source 51 may include a light source for anterior eye segment observation and another light source for posterior eye segment observation. For example, the illumination light source 51 may include a visible light source that outputs visible light. The illumination light source 51 may include an infrared light source that outputs infrared light. Here, the center wavelength of the infrared light may belong to a range between 800 nm and 1000 nm, for example.

The slit forming part 53 is configured and used to generate slit light. The slit forming part 53 may have a pair of slit blades. The width of the slit light to be generated may be varied by changing the interval between the slit blades. The interval between the slit blades is referred to as the slit width. Further, the orientation of the slit light may be varied by turning the pair of slit blades together. The configuration of the slit forming part 53 is not limited to the aspects including a pair of slit blades, and may be any other aspects.

The illumination system 8 includes the focus mechanism 50 for changing the focal position (focal point) of the illumination system 8. The focus mechanism 50 is configured to move the objective lens 54 in the direction along the optical axis O2. The movement of the objective lens 54 may be carried out automatically and/or manually. In the case where automatic movement of the objective lens 54 is employed, the computer 100 may be configured to determine the focal position by analyzing an image in which an image corresponding to the return light from the subject's eye E is depicted, for example. In addition, the computer 100 may further control the actuator so as to move the objective lens 54 in the direction along the optical axis O2 to the focal position determined. On the other hand, in the case where manual movement of the objective lens 54 is employed, the actuator may be operated to move the objective lens 54 in the direction along the optical axis O2 in accordance with an operation performed by the user.

The illumination system 8 may include the second focusing lens that is disposed at a position on the optical axis O2 between the objective lens 54 and the slit forming part 53. In the case where such a second focusing lens is provided, the focus mechanism 50 varies the focal position of the slit light by moving the second focusing lens in the direction along the optical axis O2. Further, the entire (or, a part of the) illumination system 8 may be configured to be movable in the direction along the optical axis O2. If this is the case, the focus mechanism 50 changes the focal position of the slit light by moving the entire (or, a part of the) illumination system 8 in the direction along the optical axis O2. As in the case where the objective lens 54 is moved, the movement of the second focusing lens or the illumination system 8 with the focus mechanism 50 may be carried out automatically or manually.

Although not shown in FIG. 3, the mirror 12 is disposed on the optical axis O2 that reflects and redirects the illumination light beam output from the illumination system 8 toward the subject's eye E. Some typical aspect examples may be configured to turn the illumination system 8 and the mirror 12 together.

In some aspect examples described below, the description will be made with reference to the slit lamp microscope 1 unless otherwise mentioned. However, slit lamp microscopes applicable to the aspect examples below or other aspect examples are not limited to the slit lamp microscope 1.

<First Aspect>

Figure 4:
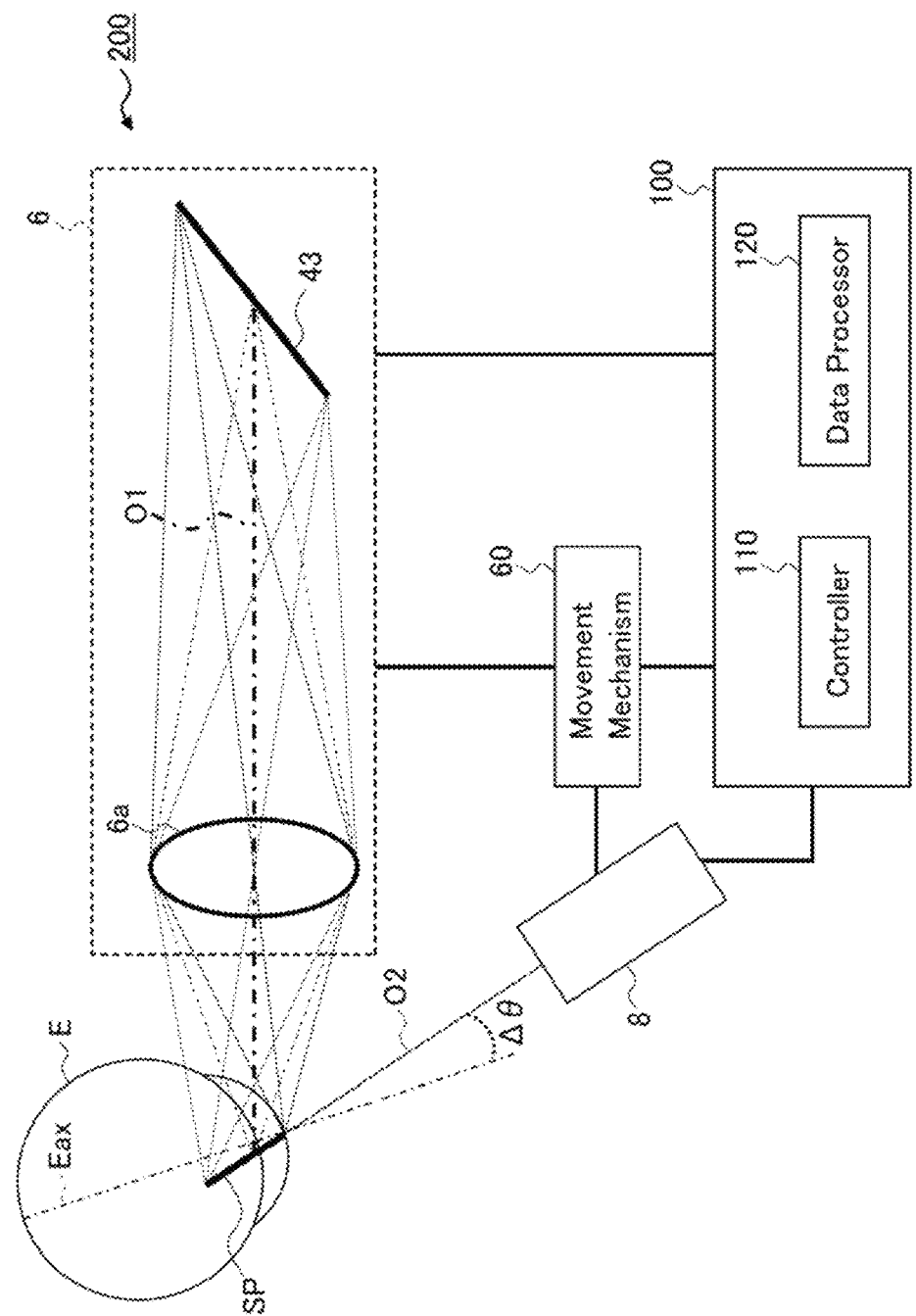
FIG. 4 is a schematic diagram illustrating the configuration of the slit lamp microscope according to the aspect example.
Figure 5:
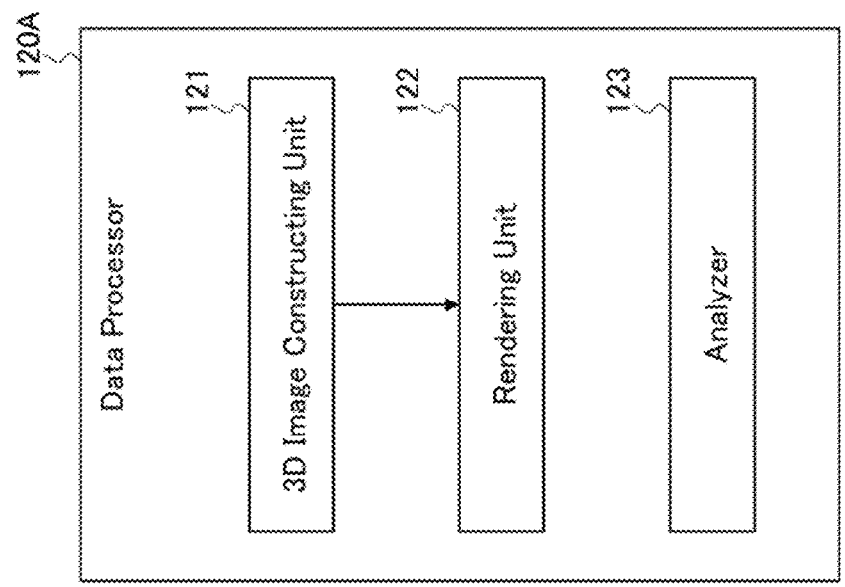
FIG. 5 is a schematic diagram illustrating the configuration of the slit lamp microscope according to the aspect example.

The slit lamp microscope according to the first aspect will now be described. FIG. 4 and FIG. 5 show configuration examples of the slit lamp microscope 200 according to the present aspect.

As shown in FIG. 4, the slit lamp microscope 200 includes the movement mechanism 60 in addition to the photographing system (observation and photographing system) 6, the illumination system 8 and the computer 100 that are same as those of the slit lamp microscope 1. The computer 100 includes the controller 110 and the data processor 120. The data processor 120A shown in FIG. 5 is an example of the data processor 120. The data processor 120 (120A) includes the three dimensional image constructing processor 121, the rendering processor 122, and the analyzing processor 123.

The slit lamp microscope 200 may be a single apparatus or may be a system that includes two or more apparatuses. In some aspect examples, the slit lamp microscope 200 includes a main body apparatus, the computer 100, and a communication device. The main body apparatus includes the illumination system 8, the photographing system 6, and the movement mechanism 60. The communication device establishes and performs communication between the main body apparatus and the computer 100. Further, in some aspect examples, the slit lamp microscope 200 includes, in addition to the main body apparatus (and the computer 100) same as the above, a computer for remote operation that is capable of accessing the main body apparatus (or the computer 100) via a communication line.

The illumination system 8 illuminates the anterior segment of the subject's eye E with slit light. The reference character O2 denotes the optical axis of the illumination system 8 (referred to as the illumination optical axis). The illumination system 8 may be capable of changing the width, the length, and the orientation of slit light, for example. The length of the slit light may be the size of a cross section of the slit light in the direction perpendicular to the cross sectional width direction of the slit light. Here, the cross sectional width direction is a direction corresponding to the slit width. In some typical aspect examples, the slit width and the slit length may be represented as sizes of a projection image of the slit light formed on the anterior segment, or as sizes of the slit formed by the slit forming part 53.

The photographing system 6 photographs the anterior segment being illuminated with the slit light from the illumination system 8. The reference character O1 denotes the optical axis of the photographing system 6 (referred to as the photographing optical axis). The photographing system 6 includes the optical system 6a and the image sensor 43.

The optical system 6a directs light from the anterior segment of the subject's eye E, which is being illuminated with the slit light, to the image sensor 43. The image sensor 43 receives the light directed by the optical system 6a with its light detecting surface (light detecting plane, light detector array).

The light directed by the optical system 6a (i.e., the light from the anterior segment of the subject's eye E) include return light of the slit light being projected onto the anterior segment, and may further include other kinds of light. Examples of the return light include reflected light, scattered light, and fluorescence. Examples of the other kinds of light include light from the environment in which the slit lamp microscope 200 is installed, such as indoor light (interior light) and sunlight.

The illumination system 8 and the photographing system 6 according to the present aspect function as a Scheimpflug camera. In other words, the configurations and the arrangement of the illumination system 8 and the photographing system 6 are determined such that the subject plane SP determined based on the illumination system 8, the principal plane of the optical system 6a, and the light detecting surface of the image sensor 43 meet the Scheimpflug condition.

More specifically, as shown in FIG. 1E, the configurations and the arrangement of the illumination system 8 and the photographing system 6 are determined as in the following manner: the subject plane SP including the focal point of the illumination system 8 whose position has been shifted under the influence of the refractive index of a tissue of the anterior segment, the principal plane of the optical system 6a, and the light detecting surface of the image sensor 43 are arranged such that these three planes intersect on (pass through) the same straight line. Such configurations and arrangement allow the entire subject plane SP to be in focus and photographed. Note that as described above, because a conventional Scheimpflug-type slit lamp microscope does not take into consideration the positional shift of the focal point of the illumination system caused by the refractive index of a tissue of the anterior segment, the conventional Scheimpflug-type slit lamp microscope cannot perform photography with the entire subject plane SP in focus.

For example, the area of the subject plane SP may be set wider than the area from the anterior surface of the cornea to the crystalline lens (typically, the posterior surface of the crystalline lens). The area of the subject plane SP is not limited to this. In addition, position matching of the subject plane SP may be performed with respect to a predetermined area of the subject's eye E to be photographed. Here, the predetermined area of the subject's eye E to be photographed may include the area from the anterior surface of the cornea to the posterior surface of the crystalline lens, for example. The operation for the position matching may include a known operation for alignment, for example.

In order to satisfy the Scheimpflug condition, designing, adjustment, and processing relating to the following items or matters are performed in some typical aspect examples: the configurations and the arrangement of the elements included in the illumination system 8; the configurations and the arrangement of the elements included in the photographing system 6; and the relative position between the illumination system 8 and the photographing system 6.

The angle formed by the illumination optical axis O2 and the photographing optical axis O1 may be used as a parameter indicating the relative position between the illumination system 8 and the photographing system 6. The angle is referred to as the imaging angle. Note that the illumination optical axis O2 coincides with the ocular optical axis Eax in a conventional Scheimpflug-type slit lamp microscope. In contrast, in the slit lamp microscope 200 according to the present aspect, the ocular optical axis Eax and the illumination optical axis O2 form the angle $\Delta\theta$. The angle $\Delta\theta$ is referred to as the shift angle.

The shift angle $\Delta\theta$ is determined based at least on the refractive index of the anterior segment. The refractive index may be a measured value of the refractive index of the subject's eye E, or may be a standard value. Any of the values indicated by the eye models described above are examples of the standard value.

The shift angle $\Delta\theta$ may be determined based further on other ocular parameters. Examples of such ocular parameters include the corneal curvature radius, the corneal thickness, the anterior chamber depth, the curvature radius of the anterior surface of the crystalline lens, the crystalline lens thickness, and the curvature radius of the posterior surface of the crystalline lens. In addition, the shift angle $\Delta\theta$ may be determined depending on the imaging angle formed by the illumination optical axis O2 and the photographing optical axis O1.

As described above, the shift angle $\Delta\theta$ may be set to a value belonging to the range of 3 to 13 degrees, on the basis of any one or more of the individual differences in ocular parameters, the type of the eye model to be referred to, and the imaging angle, and the like. Further, the shift angle $\Delta\theta$ may be set to a value belonging to the range of 6 to 10 degrees. Note that the value of the shift angle $\Delta\theta$ is not limited to these examples.

The movement mechanism 60 is configured to move the illumination system 8 and the photographing system 6. In the present aspect, the movement mechanism 60 can move the illumination system 8 and the photographing system 6 together in the lateral direction. In some typical aspect examples, when moving the illumination system 8 and the photographing system 6 together in the lateral direction, the longitudinal direction of the slit light is oriented along the vertical direction. In other words, in some typical control examples, the orientation of the slit light (the longitudinal direction of the slit light) and the moving direction of the illumination system 8 and the photographing system 6 are perpendicular to each other. This allows the subject's eye E to be scanned with the slit light.

In addition, the movement mechanism 60 may be capable of performing movement of the illumination system 8 and movement of the photographing system 6 independently of each other. For example, the movement mechanism 60 may be capable of performing the rotation (turning, turn) of the illumination system 8 in the horizontal direction and the rotation of the photographing system 6 in the horizontal direction independently of each other. With this, the imaging angle formed by the illumination optical axis O2 and the photographing optical axis O1 can be changed.

In the case where the configuration illustrated in FIG. 2 is employed, the movement mechanism 60 may include two actuators. One of the two actuators is configured to turn the support arm 16 that supports the photographing system (observation and photographing system) 6, in the lateral direction. The other actuator is configured to turn the support arm 17 that supports the illumination system 8, in the lateral direction. This makes it possible to turn the illumination system 8 and the photographing system 6 independently of each other as well as coaxially with each other.

The movement modes (movement aspects) of the illumination system 8 by the movement mechanism 60 are not limited to the examples described above. Likewise, the movement modes (movement aspects) of the photographing system 6 are not limited to the examples described above. In some aspect examples, the movement mechanism 60 may be configured to be capable of moving the illumination system 8 and the photographing system 6 together in an arbitrary direction. Also, in some aspect examples, the movement mechanism 60 may be configured to be capable of arbitrarily changing the relative position between the illumination system 8 and the photographing system 6.

The controller 110 of the computer 100 controls each part of the slit lamp microscope 200. For example, the controller 110 controls the elements of the illumination system 8, the elements of the photographing system 6, the movement mechanism 60, the data processor 120, and the like.

The controller 110 includes one or more processors, one or more main storage devices (main memories, primary storage), one or more auxiliary storage devices (auxiliary memories, secondary storage), and the like. the auxiliary storage device stores control programs. The control programs may be stored in a computer or a storage device accessible by the slit lamp microscope 200. The functions of the controller 110 are implemented through cooperation of software such as the control programs and hardware such as the processors.

In order to conduct scanning of a three dimensional region of the subject's eye E with slit light, the controller 110 may apply the following controls of the illumination system 8, the photographing system 6, and the movement mechanism 60.

To begin with, the controller 110 controls the movement mechanism 60 in order to place the illumination system 8 and the photographing system 6 at a scan start position determined in advance. This control is referred to as the alignment control. The scan start position of some aspect examples may be a position corresponding to the end portion (the first end portion) of the cornea of the subject's eye E in the lateral direction. Alternatively, the scan start position of some aspect examples may be a position further away in the lateral direction from the ocular optical axis Eax than the position corresponding to the first end portion of the cornea of the subject's eye E. Some aspect examples of the alignment control will be described below; however, aspects of the alignment control are not limited thereto.

The alignment control of some aspect examples may include the following controls: control for determining the arrangement of the illumination system 8 in such a way that the angle of the illumination optical axis O2 against the ocular optical axis Eax of the subject's eye E becomes equal to a predetermined shift angle ($\Delta\theta$); control for determining the arrangement of the photographing system 6 in such a way that the angle of the photographing optical axis O1 against the illumination optical axis O2 of the illumination system 8 that has been placed in the above arrangement state becomes equal to a predetermined imaging angle ($\alpha$-$\Delta\theta$); and control for moving together the illumination system 8 and the photographing system 6 that have been placed in the respective above arrangement states, to the scan start position determined in advance.

The alignment control of some other aspect examples may include the following controls: control for determining the arrangement between the illumination system 8 and the photographing system 6 in such a way that the angle formed by the illumination optical axis O2 and the photographing optical axis O1 becomes equal to a predetermined imaging angle ($\alpha$-$\Delta\theta$): control for determining the arrangement of the illumination system 8 in such a way that the illumination optical axis O2 of the illumination system 8, which has been place at such a relative position with respect to the photographing system 6, forms a predetermined shift angle ($\Delta\theta$) with respect to the ocular optical axis Eax of the subject's eye E; and control for moving together the illumination system 8 and the photographing system 6, which have been placed in the above arrangement, to the scan start position determined in advance.

The alignment control of some yet other aspect examples may include the following controls: control for determining the arrangement between the illumination system 8 and the photographing system 6 in such a way that the angle formed by the illumination optical axis O2 and the photographing optical axis O1 becomes equal to a predetermined imaging angle ($\alpha$); control for moving together the illumination system 8 and the photographing system 6, which have been placed in the above arrangement, to the scan start position determined in advance in such a way that the illumination optical axis O2 becomes to coincide with the ocular optical axis Eax of the subject's eye E; and control for moving the illumination system 8 so as to rotate the illumination optical axis O2, which has been placed to coincide with the ocular optical axis Eax, by a predetermined shift angle ($\Delta\theta$).

After the illumination system 8 and the photographing system 6 have been arranged at the scan start position, the controller 110 controls the illumination system 8 to start illumination of the subject's eye E with the slit light. This control is referred to as the slit light illuminating control. Note that the slit light illuminating control may be performed prior to the execution of the alignment control or during the execution of the alignment control. The illumination system 8 of some typical aspect examples emits continuous light as the slit light; however, the illumination system 8 of some other aspect examples may emit intermittent light (pulse light) as the slit light. Furthermore, the illumination system 8 of some typical aspect examples emits visible light as the slit light; however, the illumination system 8 of some other aspect examples may emit infrared light as the slit light.

At the same time as the start of the slit light illumination, or at an arbitrary time before or after the start of the slit light illumination, the controller 110 controls the photographing system 6 to start motion-picture photography of the subject's eye E. This control is referred to as the imaging control (photography control). More specifically, the photographing system 6 acquires a plurality of images of the anterior segment of the subject's eye E, by performing repetitive imaging (repetitive photographing) in parallel with the movement of the illumination system 8 and the photographing system 6 executed by the movement mechanism 60. The motion-picture photography is performed at a predetermined repetition rate (frame rate, photographing rate).

After having executed the alignment control, the slit light illuminating control, and the imaging control, the controller 110 controls the movement mechanism 60 to start the movement of the illumination system 8 and the photographing system 6 (the movement control). By the movement control, the illumination system 8 and the photographing system 6 are integrally moved. In other words, the movement control induces the movement of the illumination system 8 and the photographing system 6 while the relative position between the illumination system 8 and the photographing system 6 (e.g., the imaging angle $\alpha$-$\Delta\theta$) is being maintained. The illumination system 8 and the photographing system 6 are moved from the above-described scan start position to a scan end position determined in advance. As with the scan start position, the scan end position of some aspect examples may be a position corresponding to the end portion (the second end portion) of the cornea on the opposite side of the first end portion in the lateral direction. In some other aspect examples, the scan end position may be a position further away in the lateral direction from the ocular optical axis Eax than the second end portion. The scan area is an area from the scan start position to the scan end position.

Scanning with the slit light of some aspect examples is conducted in such a way that motion-picture photography is being performed by the photographing system 6 while the subject's eye E is being illuminated with the slit light as well as while the illumination system 8 and the photographing system 6 are being moved in the horizontal direction. Here, the slit light is oriented such that its width direction coincides with the horizontal direction and its longitudinal direction coincides with the vertical direction.

Also, the length of the slit light (i.e., the size of the slit light in the vertical direction) of some aspect examples may be set to a value equal to or larger than the diameter of the cornea. That is, the length of the slit light may be set to be equal to or larger than the corneal diameter. In addition, as described above, the moving distance of the illumination system 8 and the photographing system 6 (i.e., the scan area) may be set to a value equal to or larger than the corneal diameter in the lateral direction. This makes it possible to apply scanning with the slit light to at least the entire cornea of the subject's eye E. Note that a wider scan area may be applied in the case of scanning the sclera, scanning the iris, scanning the corner angle, or the like. Scan areas are not limited to the above examples, and a scan area may be set in an arbitrary manner on the basis of the site to be imaged.

Such scanning yields a plurality of cross sectional images respectively corresponding to a plurality of different positions (locations) to each of which the slit light is applied. In other words, such scanning yields a moving image that represent a state in which the area illuminated with the slit light is moving in the horizontal direction. Each of the cross sections represented by the respective cross sectional images includes the subject plane SP shown in FIG. 4. The entire subject plane SP is in focus of the photographing system 6. The subject plane SP includes, for example, an area from the anterior surface of the cornea to the posterior surface of the crystalline lens. If this is the case, the slit lamp microscope 200 can obtain a clear (focused, high quality, fine, high definition) image of the three dimensional region at least from the anterior surface of the cornea to the posterior surface of the crystalline lens.

The data processor 120 executes various kinds of data processing. Examples of data processed by the data processor 120 include data obtained by the slit lamp microscope 200 and data input from the outside. For example, the data processor 120 may process images acquired by the illumination system 8 and the photographing system 6.

The data processor 120 includes one or more processors, one or more main storage devices, one or more auxiliary storage devices, and the like. Programs such as data processing programs may be stored in the auxiliary storage device. The data processing programs may be stored in a computer or a storage device accessible by the slit lamp microscope 200. The functions of the data processor 120 are implemented through cooperation of software such as the data processing programs and hardware such as the processors.

As described above, the data processor 120A, which is an aspect example of the data processor 120, includes the three dimensional image constructing processor 121, the rendering processor 122, and the analyzing processor 123 (see FIG. 5).

The three dimensional image constructing processor 121 is configured to construct a three dimensional image based on a plurality of images of the subject's eye E acquired using the illumination system 8 and the photographing system 6. The three dimensional image constructing processor 121 of the present aspect may construct a three dimensional image based on a plurality of cross sectional images acquired by performing the above scanning with the slit light to the subject's eye E.

A three dimensional image is an image (image data) whose pixel positions are defined by a three dimensional coordinate system. Examples of the three dimensional image include stack data and volume data. Stack data is constructed by embedding a plurality of two dimensional images (e.g., a plurality of cross sectional images) in a single three dimensional coordinate system based on the positional relationship of the plurality of two dimensional images. Volume data is also referred to as voxel data, and may be constructed by applying voxelization to stack data, for example.

An example of the processing for constructing a three dimensional image will now be described. The three dimensional image constructing processor 121 may extract a partial image from each of the plurality of images, and then may construct a three dimensional image from the plurality of partial images respectively extracted from the plurality of images. Here, the partial image may be any of an image corresponding to the subject plane SP (subject plane image) and an image including at least part of the subject plane image, for example. The present example enables the construction of a clear (focused, high quality, fine, high definition) three dimensional image of the area from the anterior surface of the cornea to the posterior surface of the crystalline lens.

The rendering processor 122 is configured to construct a new image (referred to as a rendered image) by performing rendering on a three dimensional image constructed by the three dimensional image constructing processor 121.

The rendering may be any kinds of processing. The rendering of some aspect examples may include three dimensional computer graphics. The three dimensional computer graphics is arithmetic processing of constructing an image having a stereoscopic effect, by converting a virtual three dimensional object (e.g., a three dimensional image such as stack data or volume data) in a three dimensional space defined by a three dimensional coordinate system, into two dimensional information.

Examples of the rendering include the volume rendering, the maximum intensity projection (MIP), the minimum intensity projection (MinIP), the surface rendering, the multi planar reconstruction (MPR), the projection image construction, the shadowgram construction, and the reproduction of cross sectional images obtained with a slit lamp microscope. In addition, the rendering processor 122 may be capable of executing arbitrary processing along with the rendering of the above-mentioned kinds.

The rendering processor 122 may identify a region in the three dimensional image corresponding to a specific site of the subject's eye E. For example, the rendering processor 122 may identify any of the following regions: a region corresponding to the cornea; a region corresponding to the anterior surface of the cornea; a region corresponding to the posterior surface of the cornea; a region corresponding to the crystalline lens; a region corresponding to the anterior surface of the crystalline lens; a region corresponding to the posterior surface of the crystalline lens; a region corresponding to the iris; and a region corresponding to the corner angle. Any known image processing, such as segmentation, edge detection, thresholding, filtering, or labeling, may be applied to the image region identification processing. Some aspect examples may introduce machine learning with a convolutional neural network to the image region identification processing.

A three dimensional image is typically stack data or volume data. Designation of a cross section of a three dimensional image may be performed manually or automatically. The automatic cross section designation of some aspect examples may be performed by the application of the image region identification described above.

On the other hand, in the case of employing manual designation of a cross section of a three dimensional image, the rendering processor 122 may apply rendering to the three dimensional image to construct a display image for manual cross section designation. The display image is typically an image representing the whole of a site to be observed, and represents an area from the anterior surface of the cornea to the posterior surface of the crystalline lens, for example. The rendering for constructing the display image is typically volume rendering or surface rendering.

The controller 110 displays the display image constructed by the rendering processor 122 on a display device (not shown in the drawings). The user designates a desired cross section in the display image using an operation device such as a pointing device. The position information of the cross section designated in the display image is input to the rendering processor 122.

Since the displayed image is a rendered image of the three dimensional image, there is a trivial positional correspondence between the displayed image and the three dimensional image. Based on this positional correspondence, the rendering processor 122 may identify the position of the cross section in the three dimensional image that corresponds to the position of the cross section designated in the display image. In short, the rendering processor 122 designates a cross section of the three dimensional image.

Further, the rendering processor 122 may construct a three dimensional partial image by cutting the three dimensional image at the cross section designated. The rendering processor 122 may apply rendering to the three dimensional partial image to construct an image for display.

The analyzing processor 123 is configured to apply analysis processing to an image of the subject's eye E. The image to which the analysis processing is applied may be at least one of the plurality of images acquired through scanning with the slit light, or may be an image created by processing at least one of the plurality of images, for example. Examples of the latter include a three dimensional image constructed by the three dimensional image constructing processor 121, a rendered image constructed by the rendering processor 122, and other processed images.

The analysis processing includes, for example, measurement relating to a predetermined parameter. The measurement of some aspect examples may include any of the following processes: a process of obtaining measurement data regarding a parameter indicating the morphology of a tissue such as the thickness, diameter, area, volume, angle, or shape of the tissue; and a process of obtaining data regarding a parameter indicating a relationship between tissues such as the distance, direction, or orientation. Further, examples of such measurement parameters include the following: the corneal curvature of the anterior surface; the corneal curvature radius of the anterior surface; the corneal curvature of the posterior surface; the corneal curvature radius of the posterior surface; the corneal diameter; the corneal thickness; the corneal topography; the anterior chamber depth; the corner angle; the curvature of the anterior surface of the crystalline lens; the curvature radius of the anterior surface of the crystalline lens; the curvature of the posterior surface of the crystalline lens; the curvature radius of the posterior surface of the crystalline lens; and the crystalline lens thickness. Measurement data of some aspect examples may be distribution data of a measurement parameter.

The analysis processing may further include a process of evaluating the measurement data. The evaluation of some aspect examples may include comparison with standard data (reference data). The standard data may be normal eye data (normal eye database, healthy eye, healthy eye database), or may be diseased eye data (diseased eye database) relating to a specific disease, for example. Examples of the evaluation include the following: evaluation of corneal shape (curvature radius, curvature radius distribution, topography, etc.); evaluation of corneal thickness (corneal thickness distribution); evaluation of anterior chamber depth; evaluation of corner angle (corner angle distribution); evaluation of crystalline lens shape (curvature radius, curvature radius distribution, topography, etc.); evaluation of crystalline lens thickness (crystalline lens thickness distribution); and evaluation of cataract (opacity).

The slit lamp microscope 200 may include a communication device that performs data communication with other apparatuses. The communication device executes transmission of data to another apparatus and reception of data sent from another apparatus. The data communication system used in the communication device is optional. For example, the communication device includes one or more of various kinds of communication interfaces such as a communication interface conforming to the Internet, a communication interface conforming to a dedicated line, a communication interface conforming to LAN, and a communication interface conforming to near field communication. The data communication may include at least one of wireless communication and wired communication. Data to be transmitted and/or data to be received by the communication device may have been encrypted. If this is the case, for example, the controller 101 and/or the data processor 120 includes an encryptor and/or a decryptor. The encryptor is configured to execute encryption of data to be transmitted by the communication device. The decryptor is configured to execute decryption of data that has been received by the communication device 9.

The slit lamp microscope 200 may include a display device and an operation device. Alternatively, at least one of the display device and the operation device may be a peripheral device of the slit lamp microscope 200. The display device is configured to display various kinds of information under control of the controller 101. The display device may include a flat panel display such as a liquid crystal display (LCD). The operation device includes a device or tool for operating the slit lamp microscope 200 and a device or tool for inputting information. The operation device includes, for example, a button, a switch, a lever, a dial, a handle, a knob, a mouse, a keyboard, a trackball, an operation panel, and the like. A device in which a display device and an operation device are integrated, such as a touch screen, may be used.

<Second Aspect>

Figure 6:
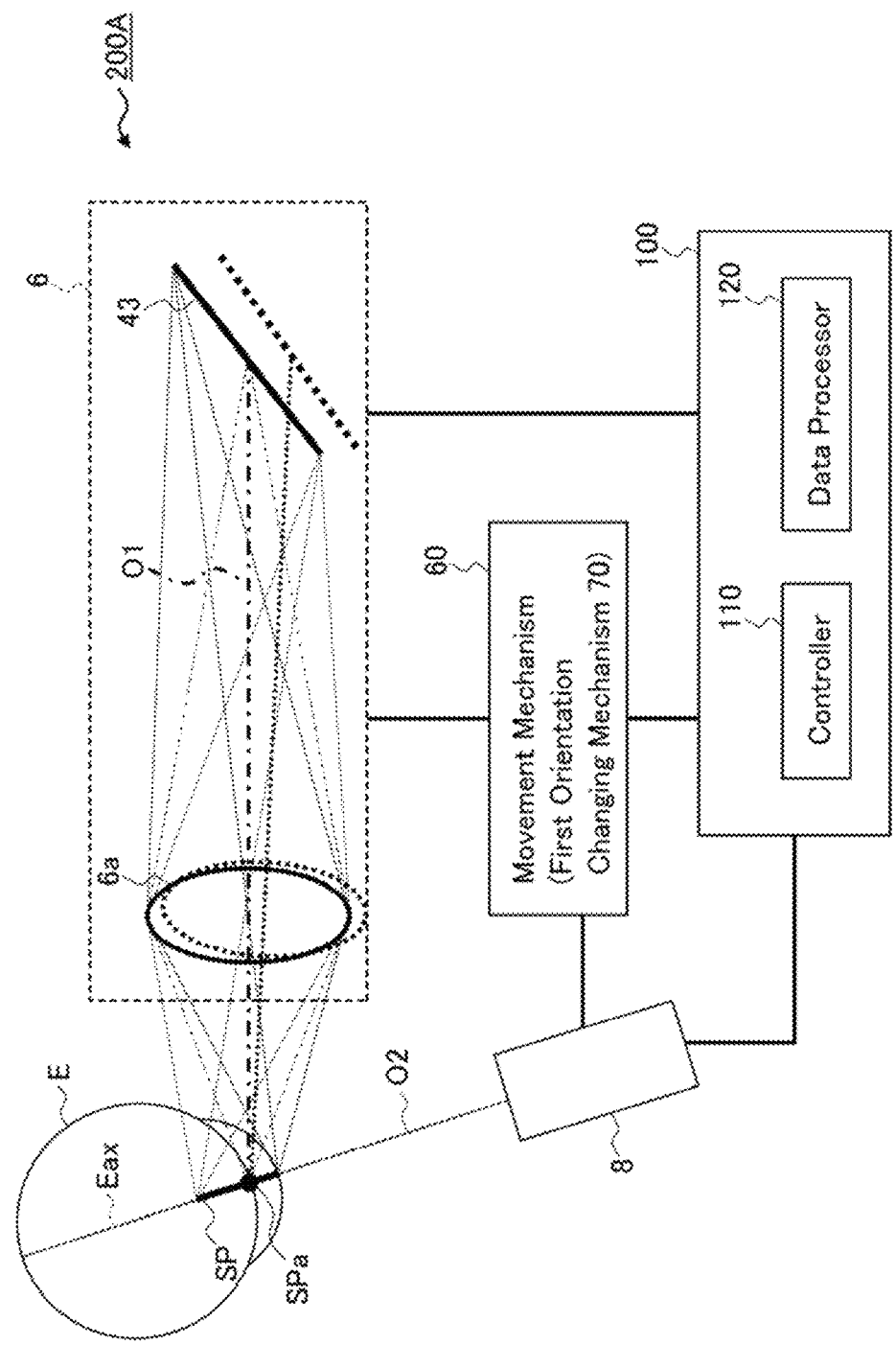
FIG. 6 is a schematic diagram illustrating the configuration of the slit lamp microscope according to the aspect example.
Figure 7:
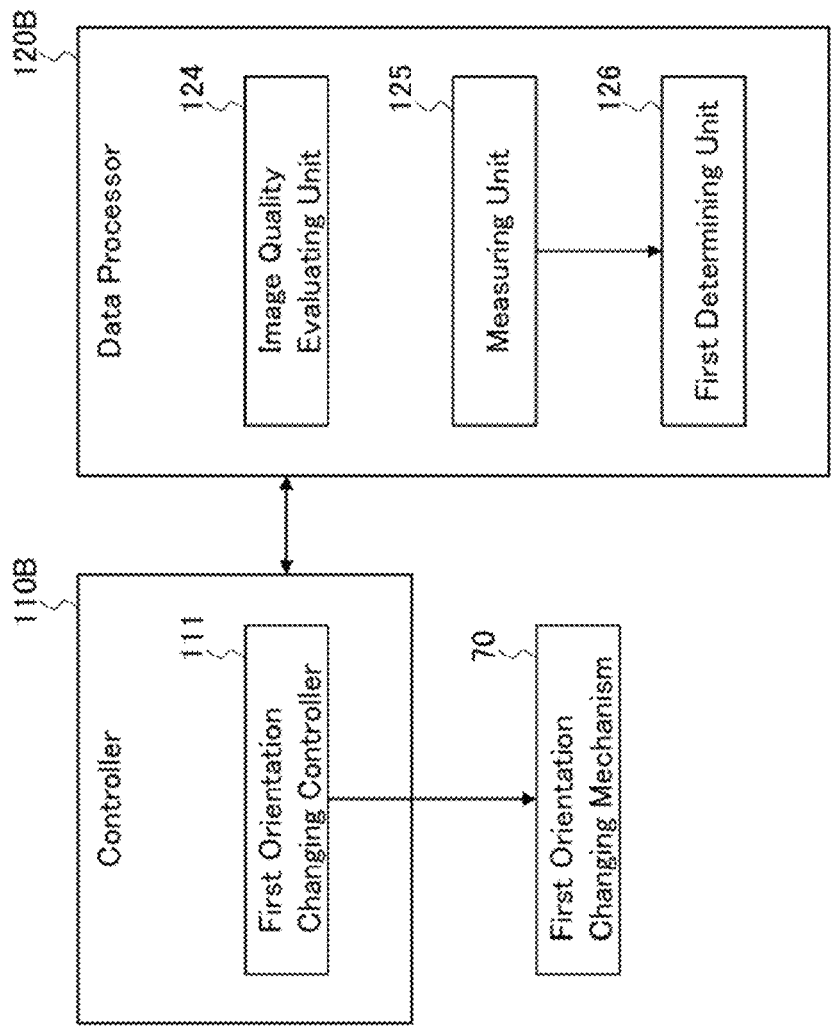
FIG. 7 is a schematic diagram illustrating the configuration of the slit lamp microscope according to the aspect example.

The slit lamp microscope according to the second aspect will be described. FIG. 6 and FIG. 7 show examples of the configuration of the slit lamp microscope 200A according to the present aspect.

As shown in FIG. 6, the slit lamp microscope 200A includes the photographing system 6, the illumination system 8, the movement mechanism 60, and the computer 100, as with the slit lamp microscope 200 according to the first aspect. The movement mechanism 60 according to the present aspect functions as the first orientation changing mechanism 70.

The computer 100 includes the controller 110 and the data processor 120. The controller 110B and the data processor 120B shown in FIG. 7 are an example of the controller 110 of the present aspect and an example of the data processor 120 of the present aspect, respectively. The controller 110B includes the first orientation changing controller 111. The data processor 120B includes the image quality evaluating processor 124, the measuring processor 125, and the first determining processor 126. The data processor 120 (120B) of the present aspect may further include any of the three dimensional image constructing processor 121, the rendering processor 122, and the analyzing processor 123.

The first orientation changing mechanism 70 is configured to change the orientation of the optical axis of the photographing system 6 (the photographing optical axis O1). That is, the first orientation changing mechanism 70 is configured to change the orientation of the photographing system 6. In other words, the first orientation changing mechanism 70 is configured to turn the photographing system 6. For example, the first orientation changing mechanism 70 turns the photographing system 6 substantially about (around) the intersection between the subject plane SP and the photographing optical axis O1, in the state where the aforementioned alignment has already been carried out. The reference character SPa in FIG. 6 denotes a virtual turning axis (virtual pivot) of the photographing system 6, which is substantially located at the intersection of the subject plane SP and the photographing optical axis O1. The first orientation changing mechanism 70 operates under the control of the first orientation changing controller 111. The first orientation changing mechanism 70 of some aspect examples may include an actuator that generates a rotational driving force, or may include an actuator that generates a linear driving force and a mechanism that converts the linear driving force into a rotational driving force.

The image quality evaluating processor 124 is configured to analyze an image of the subject's eye E acquired by the photographing system 6 to evaluate the image quality of the image. An image quality evaluation parameter of some aspect examples may be an edge strength (the magnitude of a gradient, the magnitude of a differential value), or may be any kind of parameter other than an edge strength. The image quality evaluating processor 124 analyzes the image of the subject's eye E to calculate the value of the image quality evaluation parameter, and performs the image quality evaluation by comparing the calculated parameter value with a threshold value determined in advance.

The first orientation changing controller 111 may be configured to control the first orientation changing mechanism 70 based on a result of the evaluation performed by the image quality evaluating processor 124. For example, if the image quality evaluating processor 124 has determined that the parameter value is less than the threshold value, the first orientation changing controller 111 may execute control of the first orientation changing mechanism 70 in order to change the orientation of the photographing system 6.

The measuring processor 125 and the first determining processor 126 are configured to generate information to be used for changing the orientation of the photographing system 6 from the orientation at present (orientation at a certain time) to a preferred orientation (target orientation). Some aspect examples may combine the information generation performed by the measuring processor 125 and the first determining processor 126, and the image quality evaluation performed by the image quality evaluating processor 124 with each other. Alternatively, some aspect examples may execute only one of the information generation and the image quality evaluation.

The measuring processor 125 is configured to analyze an image of the subject's eye E acquired by the photographing system 6 to measure the corneal curvature radius of the subject's eye E. In some aspect examples, the image analyzed by the measuring processor 125 may be one cross sectional image or two or more cross sectional images acquired using the slit light, or may be a three dimensional image constructed based on scanning with the slit light. The measuring processor 125 may be configured as the analyzing processor 123 of the first aspect or as a part thereof.

For example, the measuring processor 125 may analyze an image of the subject's eye E acquired by the photographing system 6 to identify an image region corresponding to the anterior surface of the cornea. This image region identification of some aspect examples may include any of segmentation, edge detection, thresholding, filtering, labeling, and machine learning using a convolutional neural network.

The measuring processor 125 may perform measurement on a parameter other than the corneal curvature radius. The measurement parameter may be any kind of parameter that can be used for changing the orientation of the photographing system 6.

The first determining processor 126 is configured to determine a target orientation of the photographing system 6 (a target orientation of the photographing optical axis O1) based at least on a result of the measurement performed by the measuring processor 125. The target orientation is determined to be the orientation of the photographing system 6 (the orientation of the principal plane and the orientation of the image plane) such that the Scheimpflug condition is satisfied between the predetermined subject plane SP (e.g., the subject plane SP that is coincident with the ocular optical axis Eax), the predetermined principal plane of the optical system 6a, and the light detecting surface of the image sensor 43 (image plane).

Examples of a parameter that can be used in the calculation for determining the target orientation, may include any kind of parameter relating to the slit lamp microscope 200A, such that any of the following: the relative position between the illumination system 8 and the photographing system 6 (e.g., the imaging angle); the relative position of the illumination system 8 with respect to the subject's eye E (e.g., the shift angle of the illumination optical axis O2 with respect to the ocular optical axis Eax); the relative position of the photographing system 6 with respect to the subject's eye E; a setting of an element of the illumination system 6 (e.g., the slit width, the slit length); and a setting of an element of the photographing system 6 (e.g., the focal length, the aperture value). Further, in addition to or in place of the corneal curvature radius, Examples of the parameters available for the calculation for determining the target orientation, may include any kind of parameter relating to the eye, such as any of the following: the refractive index of the cornea; the refractive index of the aqueous humor; the refractive index of the crystalline lens; the corneal thickness; the anterior chamber depth; the curvature radius of the anterior surface of the crystalline lens; the crystalline lens thickness; and the curvature radius of the posterior surface of the crystalline lens. A value of the parameter relating to the eye may be a standard value or a measured value of the subject's eye E.

The calculation for determining the target orientation of some aspect examples may be performed based on a predetermined calculation equation (formula) including any of the above parameters, and/or based on a graph and/or a table related to any of the above parameters. In some aspect examples, the calculation for determining the target orientation may include processing using ray tracing, machine learning, or the like.

The first orientation changing controller 111 may execute control of the first orientation changing mechanism 70 so as to change the orientation of the photographing system 6 (the orientation of the photographing optical axis O1) to the target orientation determined by the first determining processor 126.

In the case of combining the information generation performed by the measuring processor 125 and the first determining processor 126, and the image quality evaluation performed by the image quality evaluating processor 124, some aspect examples may execute determination of the target orientation by the measuring processor 125 and the first determining processor 126 in the case where the image quality evaluating processor 124 has determined that the image quality is insufficient, and then may change the orientation of the photographing system 6 (the orientation of the photographing optical axis O1) based on the target orientation determined.

Figure 8:
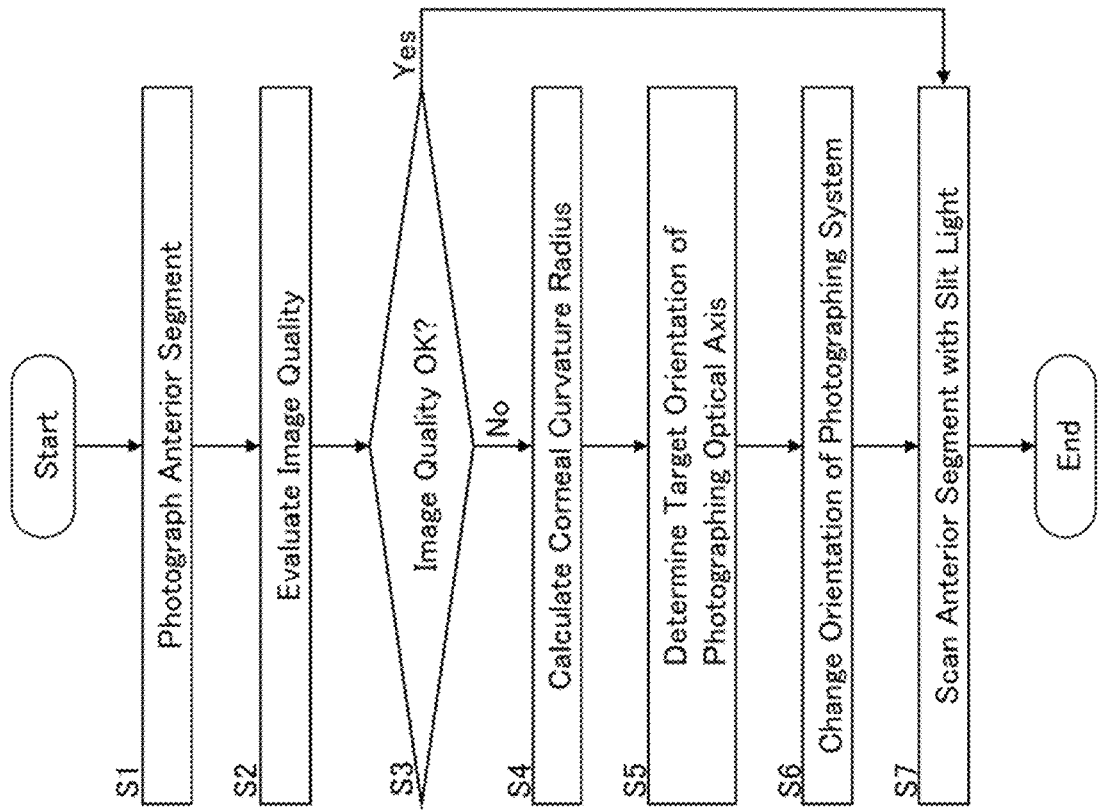
FIG. 8 is a flowchart illustrating the operation of the slit lamp microscope according to the aspect example.

An example of the operation of the slit lamp microscope 200A according to the present aspect will be described. FIG. 8 shows an example of the operation of the slit lamp microscope 200A. It is assumed that preparatory processes such as alignment have already been performed.

(S1: Photograph Anterior Segment)

To begin with, the slit lamp microscope 200A photographs the anterior segment of the subject's eye E. The anterior segment photography is carried out using the slit light, and includes one or more times of photographing operations, for example.

(S2: Evaluate Image Quality)

The image quality evaluating processor 124 analyzes the image(s) of the anterior segment acquired in the step S1 to evaluate the image quality thereof. For example, the image quality evaluating processor 124 calculates the edge strength of the image of the anterior segment and compares the calculated edge strength with a threshold value. If the edge strength is equal to or larger than the threshold value, the image is deemed to have sufficient image quality. On the other hand, if the edge strength is smaller than the threshold value, the image is deemed to have insufficient image quality.

(S3: Image Quality OK?)

In the case where the image quality evaluating processor 124 has determined in the step S2 that the image quality is sufficient (S3: Yes), the process proceeds to the step S7. On the other hand, in the case where the image quality evaluating processor 124 has determined in the step S2 that the image quality is not sufficient (S3: No), the process proceeds to the step S4.

(S4: Calculate Corneal Curvature Radius)

In the case where the image quality evaluating processor 124 has determined that the image quality of the anterior segment image acquired in the step S1 is not sufficient (S3: No), the measuring processor 125 analyzes an image of the subject's eye E to measure the corneal curvature radius. The image of the subject's eye E here may be the anterior segment image acquired in the step S1, or may be another image.

A description of an example will be given of processing that may be performed when calculating a corneal curvature radius from an image other than the anterior segment image acquired in the step S1. When the image quality evaluating processor 124 has determined that the image quality of the anterior segment image acquired in the step S1 is not sufficient (S3: No), the slit lamp microscope 200A carries out another photographing of the anterior segment of the subject's eye E. In this anterior segment photography, at least the anterior surface of the cornea is targeted and captured. The measuring processor 125 determines a corneal curvature radius by analyzing the image acquired by this anterior segment photography.

(S5: Determine Target Orientation of Photographing Optical Axis)

The first determining processor 126 determines the target orientation of the photographing system 6 (the target orientation of the photographing optical axis O1) based at least on the corneal curvature radius calculated in the step S4.

(S6: Change Orientation of Photographing System)

The first orientation changing controller 111 controls the first orientation changing mechanism 70 in such a way that the orientation of the photographing system 6 (the orientation of the photographing optical axis O1) becomes to coincide with the target orientation determined in the step S5.

(S7: Scan Anterior Segment with Slit Light)

In response to the completion of the orientation changing of the photographing system 6 in the step S6, the slit lamp microscope 200A applies a scan with the slit light to the anterior segment of the subject's eye E. In some aspect examples, such slit light scanning can yield a clear image group (a group of clear images) covering an area at least from the anterior surface of the cornea to the posterior surface of the crystalline lens.

The data processor 120B (the three dimensional image constructing processor 121) may construct a three dimensional image based on the image group. Thereby, a three dimensional image in which a three dimensional region at least from the anterior surface of the cornea to the posterior surface of the crystalline lens is represented with high definition can be obtained in some aspect examples.

The data processor 120B (the rendering processor 122) may construct a rendered image of an arbitrary kind, from the three dimensional image. Such rendering allows the user to conduct observation of a high quality image of a desired site or tissue of the subject's eye E.

The data processor 120B (the analyzing processor 123) may apply predetermined analysis processing to at least one of the plurality of images acquired in the step S7 or to an image generated by processing at least one of the plurality of images acquired in the step S7. As a result of this, an arbitrary kind of analysis data of the subject's eye E can be obtained.

In the present example, the completion of the orientation changing of the photographing system 6 (S6) triggers the scanning with the slit light (S7). However, the trigger for commencement of slit light scanning is not limited to this. In some aspect examples, scanning with the slit light may be started in response to a user's instruction. In some aspect examples, in response to the completion of the orientation changing of the photographing system 6 (S6), the process may return to the step S1, and then the slit lamp microscope 200A may once again perform any of the anterior segment photographing, the image quality evaluation, the corneal curvature radius measurement, the target orientation determination, and the change (control) of the orientation of the photographing system 6.

<Third Aspect>

Figure 9:
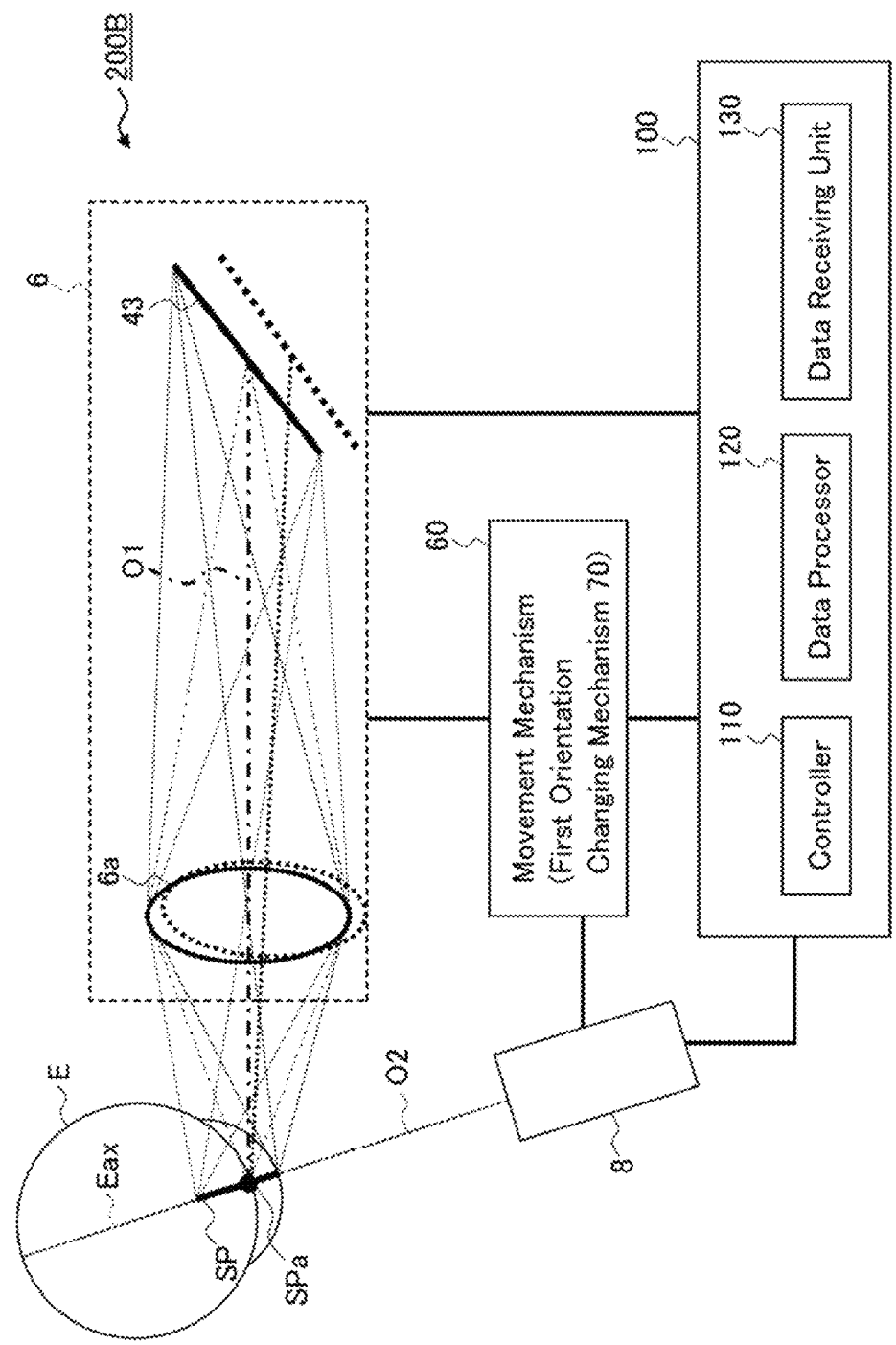
FIG. 9 is a schematic diagram illustrating the configuration of the slit lamp microscope according to the aspect example.
Figure 10:
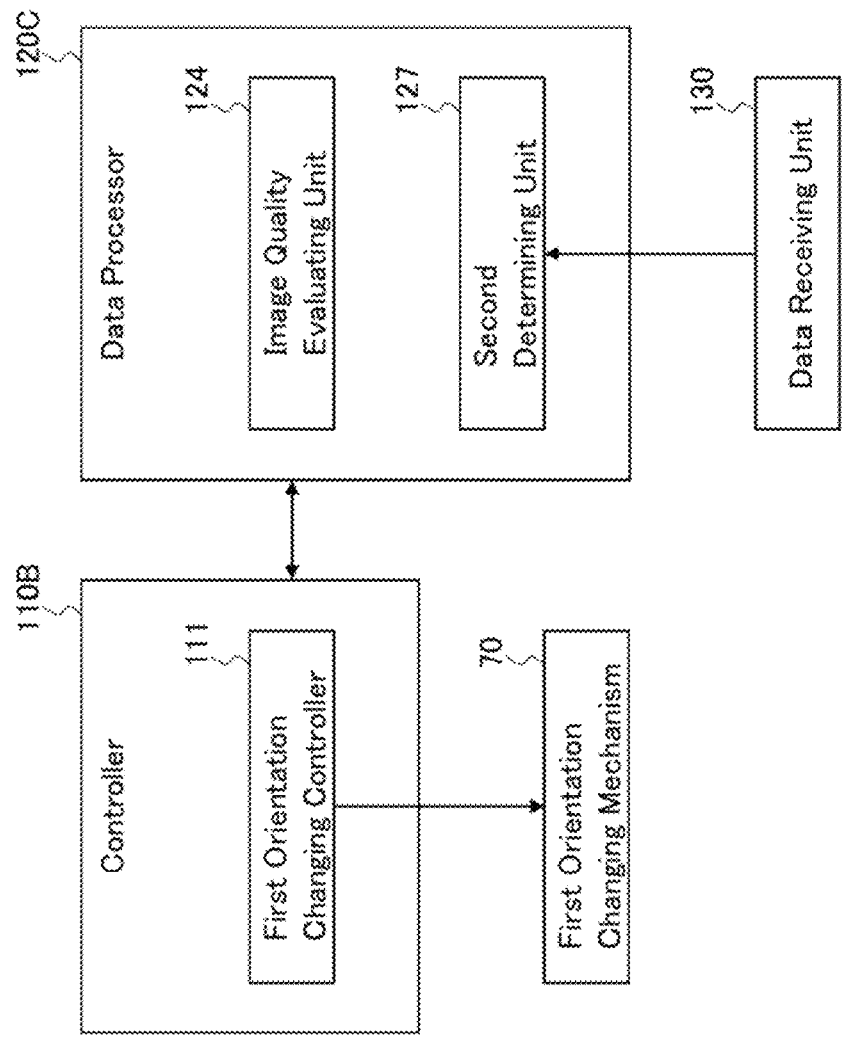
FIG. 10 is a schematic diagram illustrating the configuration of the slit lamp microscope according to the aspect example.

A description will be given of the slit lamp microscope according to the third aspect. FIG. 9 and FIG. 10 show configuration examples of the slit lamp microscope 200B according to the present aspect.

As shown in FIG. 9, the slit lamp microscope 200B includes the photographing system 6, the illumination system 8, the movement mechanism 60 functioning as the first orientation changing mechanism 70, and the computer 100, as with the slit lamp microscope 200A according to the second aspect.

The computer 100 includes the controller 110, the data processor 120, and the data receiver 130. The controller 110B and the data processor 120C illustrated in FIG. 10 are an example of the controller 110 of the present aspect and an example of the data processor 120 of the present aspect, respectively. The controller 110B includes the first orientation changing controller 111 similar to that of the second aspect. The data processor 120C includes the second determining processor 127 in addition to the image quality evaluating processor 124 similar to that of the second aspect. The data processor 120 (120C) of the present aspect may further include any of the three dimensional image constructing processor 121, the rendering processor 122, the analyzing processor 123, the measuring processor 125, and the first determining processor 126. As to these optional elements, corresponding matters and items described in the first aspect and/or second aspects may be adopted to the present embodiment.

As in the case with the second aspect, the first orientation changing controller 111 may control the first orientation changing mechanism 70 based on a result of the evaluation performed by the image quality evaluating processor 124.

The data receiver 130 receives measurement data of the corneal curvature radius of the subject's eye E acquired in advance. The data receiver 130 according to some aspect examples may include at least part of the communication device described above. If this is the case, the data receiver 130 receives the measurement data of the corneal curvature radius of the subject's eye E from a filing system such as an electronic medical record system (electronic health record system), for example. The data receiver 130 according to some other aspect examples includes a device that acquires data recorded on a recording medium, such as a drive device, a data reader, or a data scanner. If this is the case, the data receiver 130 (such as a drive device) reads out the measurement data of the corneal curvature radius of the subject's eye E recorded on a non-transitory computer-readable recording medium such as a magnetic disk, an optical disk, a magneto-optical disk, or a semiconductor memory, for example. Alternatively, the data receiver 130 (such as a data scanner) reads or scans the measurement data of the corneal curvature radius of the subject's eye E printed on a sheet.

The second determining processor 127 is configured to determine a target orientation of the photographing system 6 (a target orientation of the photographing optical axis O1) based at least on the measurement data of the corneal curvature radius of the subject's eye E acquired by the data receiver 130. A target orientation and a method of determining a target orientation (such as a calculation method) may be the same as those of the first determining processor 126 according to the second aspect.

In the case of combining the information generation performed by the second determining processor 127 and the image quality evaluation performed by the image quality evaluating processor 124, the present aspect may determine a target orientation by the second determining processor 127 when the image quality evaluating processor 124 has determined that the image quality is insufficient, and then change the orientation of the photographing system 6 based on the target orientation determined.

Figure 11:
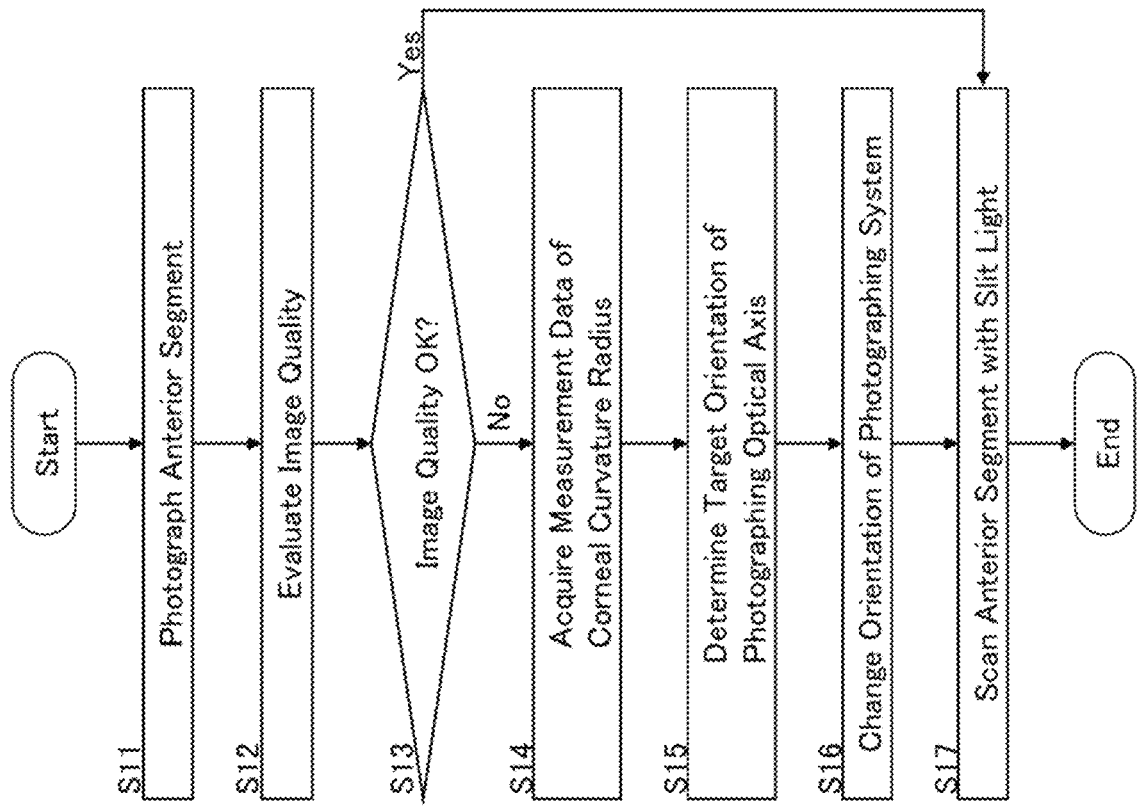
FIG. 11 is a flowchart illustrating the operation of the slit lamp microscope according to the aspect example.

An operation example of the slit lamp microscope 200B according to the present aspect will be described. FIG. 11 shows an example of the operation of the slit lamp microscope 200B. It is assumed that preparatory processes such as alignment have already been performed.

(S11: Photograph Anterior Segment)

First, the slit lamp microscope 200B performs photographing of the anterior segment of the subject's eye E, for example, in the same manner as in the step S1 of the second aspect.

(S12: Evaluate Image Quality)

The image quality evaluating processor 124 analyzes the image of the anterior segment acquired in the step S11 to evaluate the image quality thereof, in the same manner as in the step S2 of the second aspect, for example.

(S13: Image Quality OK?)

In the case where the image quality evaluating processor 124 has determined in the step S12 that the image quality is sufficient (S13: Yes), the process proceeds to the step S17. On the other hand, in the case where the image quality evaluating processor 124 has determined in the step S12 that the image quality is not sufficient (S13: No), the process proceeds to the step S14.

(S14: Acquire Measurement Data of Corneal Curvature Radius)

In the case where the image quality evaluating processor 124 has determined that the image quality of the anterior segment image acquired in the step S11 is not sufficient (S13: No), the data receiver 130 receives measurement data of the corneal curvature radius of the subject's eye E acquired in advance.

(S15: Determine Target Orientation of Photographing Optical Axis)

The second determining processor 127 determines the target orientation of the photographing system 6 (the target orientation of the photographing optical axis O1) based at least on the measurement data of the corneal curvature radius acquired in the step S14. Calculation executed here may be performed in the same manner as in the step S5 of the second aspect, for example.

(S16: Change Orientation of Photographing System)

The first orientation changing controller 111 executes control of the first orientation changing mechanism 70 such that the orientation of the photographing system 6 (the orientation of the photographing optical axis O1) becomes to coincide with the target orientation determined in the step S15, for example, in the same manner as in the step S6 of the second aspect.

(S17: Scan Anterior Segment with Slit Light)

In response to the completion of the orientation changing of the photographing system 6 in the step S16, the slit lamp microscope 200B applies a scan with the slit light to the anterior segment of the subject's eye E, for example, in the same manner as in the step S7 of the second aspect. With this, for example, a clear image group can be obtained which covers an area at least from the anterior surface of the cornea to the posterior surface of the crystalline lens.

The data processor 120C (the three dimensional image constructing processor 121) may construct a three dimensional image based on the image group obtained. Thereby, for example, a three dimensional image can be obtained in which a three dimensional region at least from the anterior surface of the cornea to the posterior surface of the crystalline lens is expressed with high definition.

The data processor 120C (the rendering processor 122) may construct an arbitrary rendered image from the three dimensional image. This enables the user to observe a high quality image of a desired site or tissue of the subject's eye E.

The data processor 120C (the analyzing processor 123) may apply predetermined analysis processing to at least one of the plurality of images acquired in the step S17 or to an image generated by processing at least one of the plurality of images acquired in the step S17. As a result of this, desired analysis data regarding the subject's eye E can be obtained.

For example, in the case where the image quality of the image of the subject's eye E acquired in the step S17 is insufficient or like cases, the data processor 120C (the measuring processor 125) may perform measurement of the corneal curvature radius of the subject's eye E by executing either of the follow processes: a process of analyzing at least one of the plurality of images acquired in the step S17 or an image generated by processing at least one of the plurality of images acquired in the step S17; or a process of analyzing an image obtained by another photographing performed after the step S17 or an image obtained by processing an image obtained by another photographing performed after the step S17. Based at least on the measurement data of the corneal curvature radius acquired in this way, the data processor 120C (the first determining processor 126) may determine a new target orientation of the photographing system 6 (a new target orientation of the photographing optical axis O1). Further, the first orientation changing controller 111 may control the first orientation changing mechanism 70 so as to change the orientation of the photographing system 6 (the orientation of the photographing optical axis O1) to the new target orientation. Such a series of processes is effective, for example, when there is a substantial difference between the measurement data of the corneal curvature radius acquired in the past and the corneal curvature radius at present.

In the present example, the completion of the orientation changing of the photographing system 6 (S16) triggers the scanning with the slit light (S17), but the trigger for the slit light scanning is not limited to this. Some aspect examples may start scanning with the slit light in response to a user's instruction. In some other aspect examples, the process may return to the step S11 in response to the completion of the orientation changing of the photographing system 6 (S16). If this is the case, the slit lamp microscope 200B may once again perform the photographing of the anterior segment, the evaluation of the image quality, and the change of the orientation of the photographing system 6. Alternatively, as in the case of the second aspect, the slit lamp microscope 200B may be configured to perform the photographing of the anterior segment, the evaluation of the image quality, the measurement of the corneal curvature radius, the determination of the target orientation, and the change of the orientation of the photographing system 6.

<Fourth Aspect>

Figure 12:
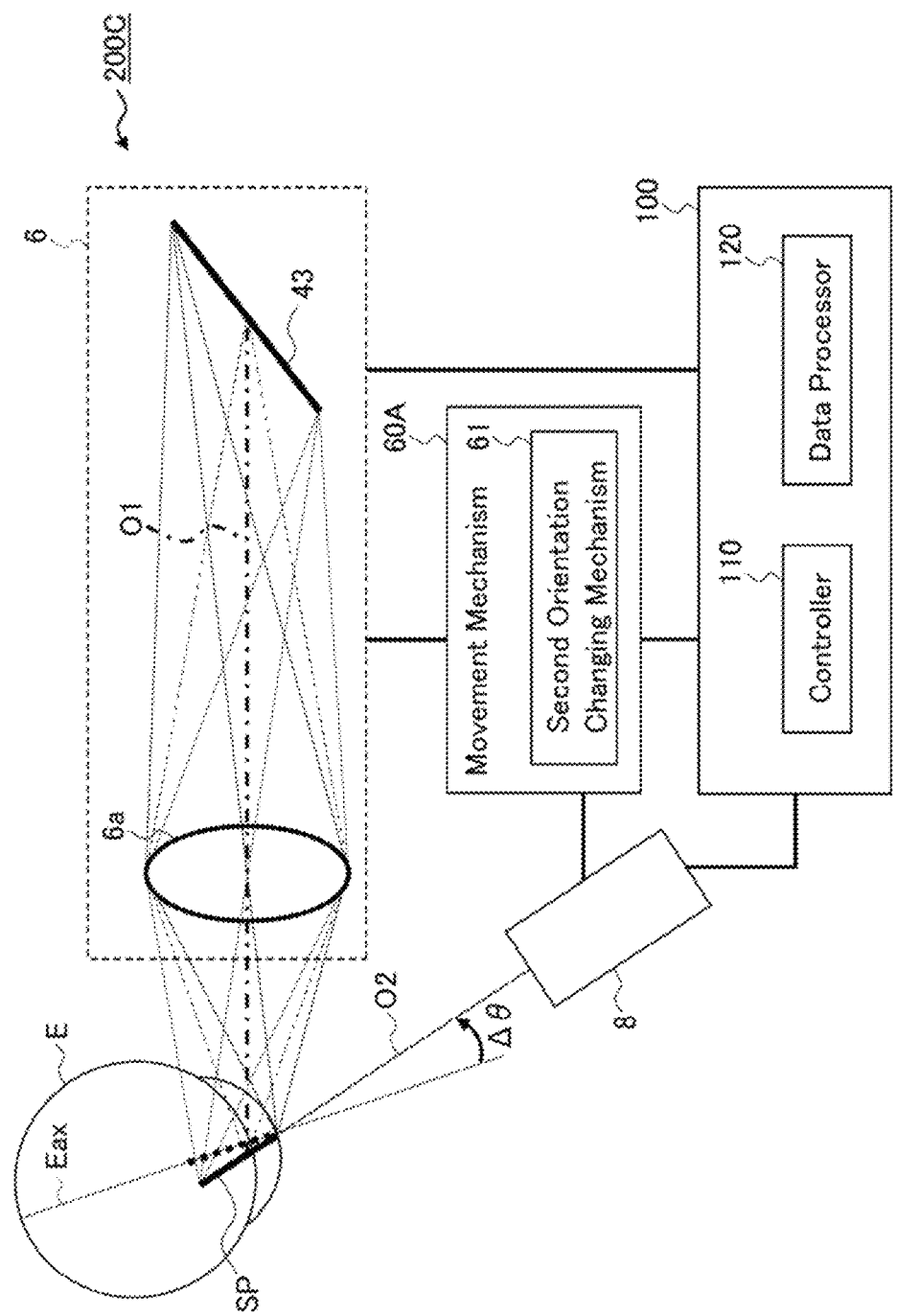
FIG. 12 is a schematic diagram illustrating the configuration of the slit lamp microscope according to the aspect example.
Figure 13:
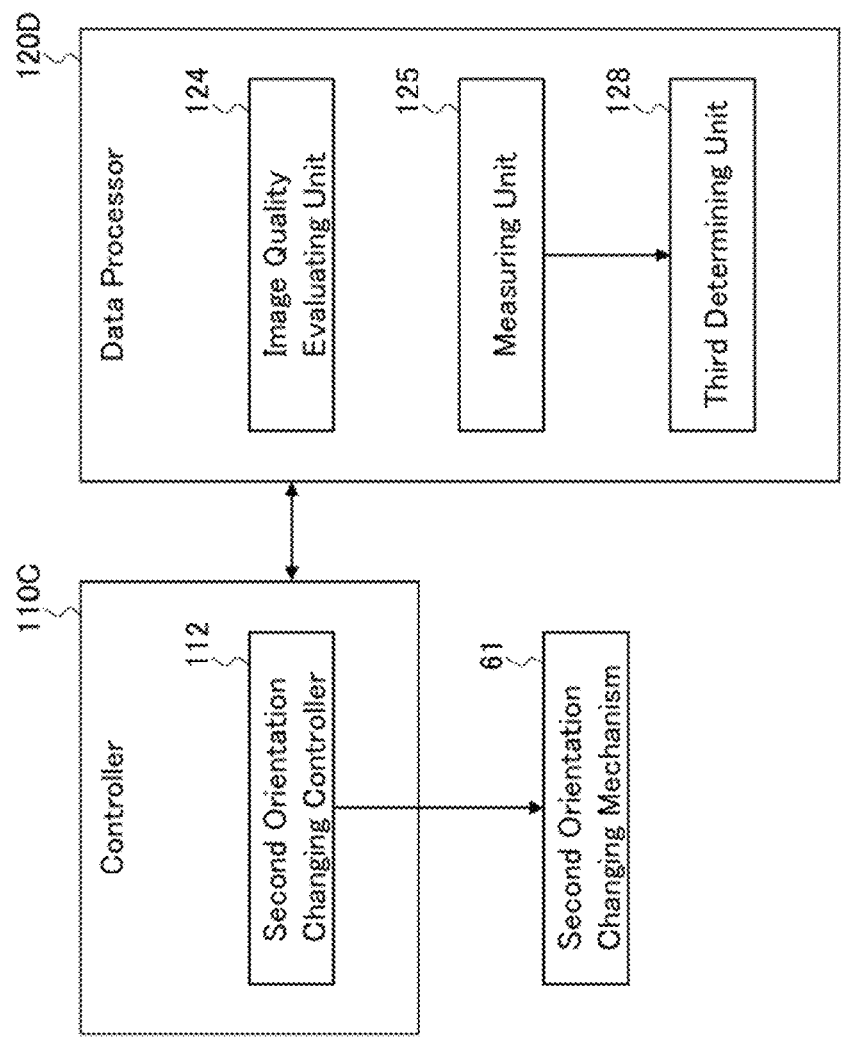
FIG. 13 is a schematic diagram illustrating the configuration of the slit lamp microscope according to the aspect example.

A description will be given of the slit lamp microscope according to the fourth aspect. FIG. 12 and FIG. 13 show configuration examples of the slit lamp microscope 200C according to the present aspect.

As shown in FIG. 12, the slit lamp microscope 200C includes the photographing system 6, the illumination system 8, and the computer 100, as with the slit lamp microscope 200 according to the first aspect. In addition, the slit lamp microscope 200C further includes the movement mechanism 60A that includes the second orientation changing mechanism 61.

The computer 100 includes the controller 110 and the data processor 120. The controller 110C and the data processor 120D illustrated in FIG. 13 are an example of the controller 110 of the present aspect and an example of the data processor 120 of the present aspect, respectively. The controller 110C includes the second orientation changing controller 112. The data processor 120D includes the image quality evaluating processor 124, the measuring processor 125, and the third determining processor 128. The data processor 120 (120D) of the present aspect may further include any of the three dimensional image constructing processor 121, the rendering processor 122, the analyzing processor 123, the first determining processor 126, and the second determining processor 127. In addition, the slit lamp microscope 200C may include the first orientation changing mechanism 70, and may further include the first orientation changing controller 111.

The second orientation changing mechanism 61 changes the orientation of the optical axis of the illumination system 8 (the orientation of the illumination optical axis O2). That is, the second orientation changing mechanism 61 changes the orientation of the illumination system 8, in other words, turns the illumination system 8. For example, the second orientation changing mechanism 61 turns the illumination optical axis O2 about (around) the intersection of the cornea of the subject's eye E and the illumination optical axis O2, in the state where the above-described alignment has been performed (see FIG. 12). The second orientation changing mechanism 61 operates under the control of the second orientation changing controller 112. The second orientation changing mechanism 61 includes, for example, an actuator that generates a rotational driving force, or an actuator that generates a linear driving force and a mechanism that converts the linear driving force into a rotational driving force.

In the present aspect, the second orientation changing mechanism 61 is included in the movement mechanism 60A. The movement mechanism 60A may be the same element as the movement mechanism 60 of the first aspect, and may include at least a mechanism for turning the illumination optical axis O2 (the second orientation changing mechanism 61).

As with the case in the second aspect, the image quality evaluating processor 124 analyzes an image of the subject's eye E acquired by the photographing system 6 to evaluate the image quality of the image. The second orientation changing controller 112 may execute control of the second orientation changing mechanism 61 based on a result of the evaluation performed by the image quality evaluating processor 124. For example, in the case where the image quality evaluating processor 124 has determined that the parameter value is less than the threshold value, the second orientation changing controller 112 may execute control of the second orientation changing mechanism 61 in order to change the orientation of the illumination optical axis O2.

The measuring processor 125 and the third determining processor 128 generate information to be used for changing the orientation of the illumination optical axis O2 from the orientation at present to a preferred orientation (the target orientation). Some aspect examples may combine the information generation performed by the measuring processor 125 and the third determining processor 128, with the image quality evaluation performed by the image quality evaluating processor 124. In some other aspect examples, only one of the information generation and the image quality evaluation may be performed.

As with the case in the second aspect, the measuring processor 125 analyzes the image of the subject's eye E acquired by the photographing system 6 to measure the corneal curvature radius thereof. The measuring processor 125 may perform measurement of a parameter other than the corneal curvature radius. This measurement parameter may be any kind of parameter that can be used for a process of changing the orientation of the illumination optical axis O2.

The third determining processor 128 is configured to determine a target orientation of the illumination optical axis O2 based at least on a result of the measurement by the measuring processor 125. The target orientation is the orientation of the illumination optical axis O2 (the orientation of the subject plane SP) such that the subject plane SP, the predetermined principal plane of the optical system 6a, and the light detecting surface (the predetermined image plane) of the image sensor 43 meet the Scheimpflug condition.

Examples of a parameter that can be used in the calculation for determining the target orientation may include any kind of parameter relating to the slit lamp microscope 200C, and may include any of the following: the relative position between the illumination system 8 and the photographing system 6 such as the imaging angle; the relative position of the illumination system 8 with respect to the subject's eye E such as the shift angle of the illumination optical axis O2 with respect to the ocular optical axis Eax; the relative position of the photographing system 6 with respect to the subject's eye E; the settings of the elements of the illumination system 6 such as the slit width and the slit length; and the settings of the elements of the photographing system 6 such as the focal length and the aperture value. Further, examples of a parameter that can be used for the calculation of determining the target orientation may include, in addition to the corneal curvature radius, any kinds of parameters relating to the eye such as any of the following: the refractive index of the cornea, the refractive index of the aqueous humor, the refractive index of the crystalline lens, the corneal thickness, the anterior chamber depth, the curvature radius of the anterior surface of the crystalline lens, the crystalline lens thickness, the curvature radius of the posterior surface of the crystalline lens. The value of the parameter relating to the eye may be a standard value or a measured value of the subject's eye E.

The calculation for determining the target orientation of some aspect examples may be performed based on a predetermined calculation equation (formula) including any of the above parameters, and/or based on a graph and/or a table related to any of the above parameters. In some aspect examples, the calculation for determining the target orientation may include processing using ray tracing, machine learning, or the like.

The second orientation changing controller 112 may execute control of the second orientation changing mechanism 61 so as to change the orientation of the illumination optical axis O2 to the target orientation determined by the third determining processor 128, which is illustrated in FIG. 12 (the rotation of the angle Δθ of the illumination optical axis O2). This makes it possible to realize the subject plane SP that satisfies the Scheimpflug condition in the relationship with the principal plane of the optical system 6a and the light detecting surface of the image sensor 43 (image plane).

In the case of combining the information generation performed by the measuring processor 125 and the third determining processor 128 with the image quality evaluation performed by the image quality evaluating processor 124, some aspect examples may execute determination of the target orientation by the measuring processor 125 and the third determining processor 128 in the case where the image quality evaluating processor 124 has determined that the image quality is insufficient, and then may change the orientation of the illumination optical axis O2 based on the target orientation determined.

Figure 14:
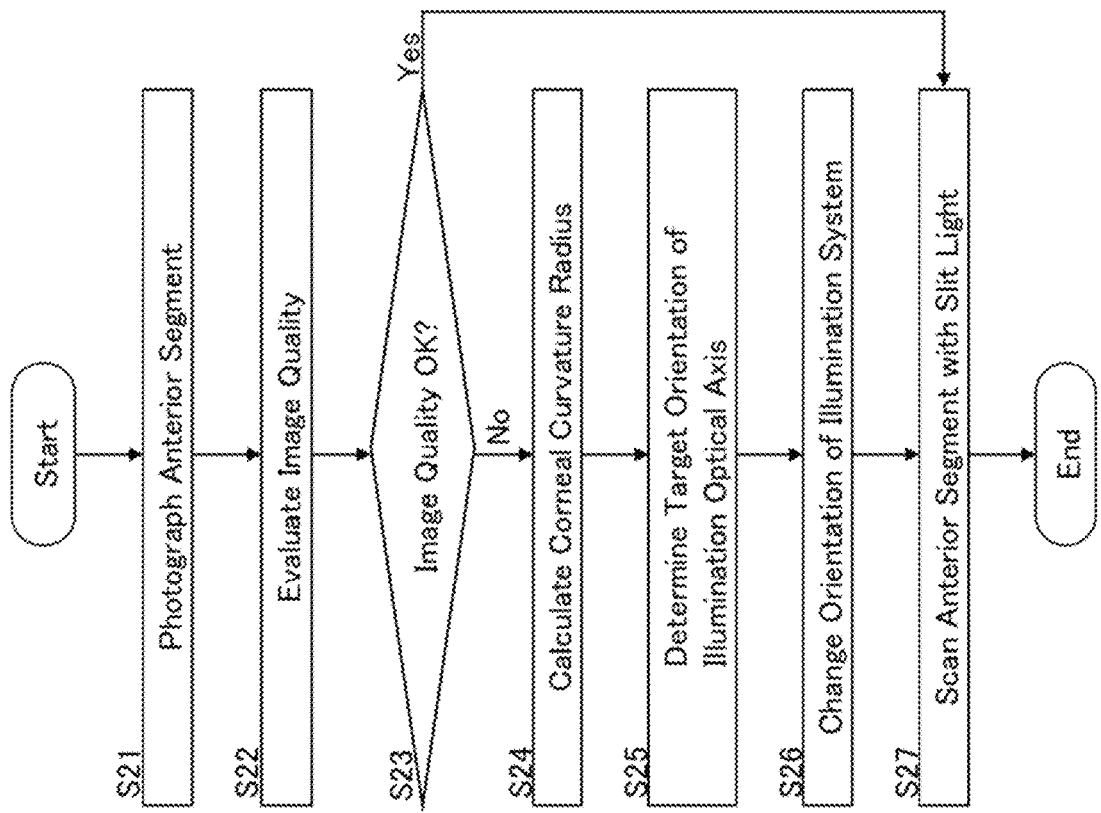
FIG. 14 is a flowchart illustrating the operation of the slit lamp microscope according to the aspect example.

An operation example of the slit lamp microscope 200C according to the present aspect will be described. FIG. 14 shows an example of the operation of the slit lamp microscope 200C. It is assumed that preparatory processes such as alignment have already been performed.
(S21: Photograph Anterior Segment)

First, the slit lamp microscope 200C photographs the anterior segment of the subject's eye E, for example, in the same manner as in the step S1 of the second aspect.
(S22: Evaluate Image Quality)

The image quality evaluating processor 124 analyzes the image of the anterior segment acquired in the step S21 to evaluate the image quality thereof, in the same manner as in the step S2 of the second aspect, for example.
(S23: Image Quality OK?)

In the case where the image quality evaluating processor 124 has determined in the step S22 that the image quality is sufficient (S23: Yes), the process proceeds to the step S27. On the other hand, in the case where the image quality evaluating processor 124 has determined in the step S22 that the image quality is not sufficient (S23: No), the process proceeds to the step S24.
(S24: Calculate Corneal Curvature Radius)

In the case where the image quality evaluating processor 124 has determined that the image quality of the anterior segment image acquired in the step S21 is not sufficient (S23: No), the measuring processor 125 analyzes an image of the subject's eye E to measure the corneal curvature radius, for example, in the same manner as in the step S4 of the second aspect. (S25: Determine target orientation of illumination optical axis)

The third determining processor 128 determines the target orientation of the illumination optical axis O2 based at least on the corneal curvature radius calculated in the step S24.
(S26: Change Orientation of Illumination System)

The second orientation changing controller 112 executes control of the second orientation changing mechanism 61 to change the orientation of the illumination system 8 in such a way that the orientation of the illumination optical axis O2 becomes to coincide with the target orientation determined in the step S25.
(S27: Scan Anterior Segment with Slit Light)

In response to the completion of the orientation changing of the illumination system 8 in the step S26, the slit lamp microscope 200C applies a scan with the slit light to the anterior segment of the subject's eye E. With this, for example, a clear image group covering an area at least from the anterior surface of the cornea to the posterior surface of the crystalline lens, can be obtained.

The data processor 120D (the three dimensional image constructing processor 121) may construct a three dimensional image based on the image group obtained. Thereby, for example, a three dimensional image in which a three dimensional region at least from the anterior surface of the cornea to the posterior surface of the crystalline lens is expressed with high definition, can be obtained.

The data processor 120D (the rendering processor 122) may construct an arbitrary rendered image from the three dimensional image. This enables the user to observe a high quality image of a desired site or tissue of the subject's eye E.

The data processor 120D (the analyzing processor 123) may apply predetermined analysis processing to at least one of the plurality of images acquired in the step S27 or to an image generated by processing at least one of the plurality of images acquired in the step S27. As a result of this, desired analysis data regarding the subject's eye E can be obtained.

In the present example, the completion of the orientation changing of the illumination system 8 (S26) triggers the scanning with the slit light (S27), but the trigger for the scanning with the slit light is not limited to this. For example, scanning with the slit light may be started in response to a user's instruction. In some aspect examples, in response to the completion of the orientation changing of the illumination system 8 (S26), the process may return to the step S21 and the slit lamp microscope 200C may once again perform the following processes: the photographing of the anterior segment; the evaluation of the image quality; the measurement of the corneal curvature radius; the determination of the target orientation; and the change of the orientation of the illumination system 8.

<Fifth Aspect>

Figure 15:
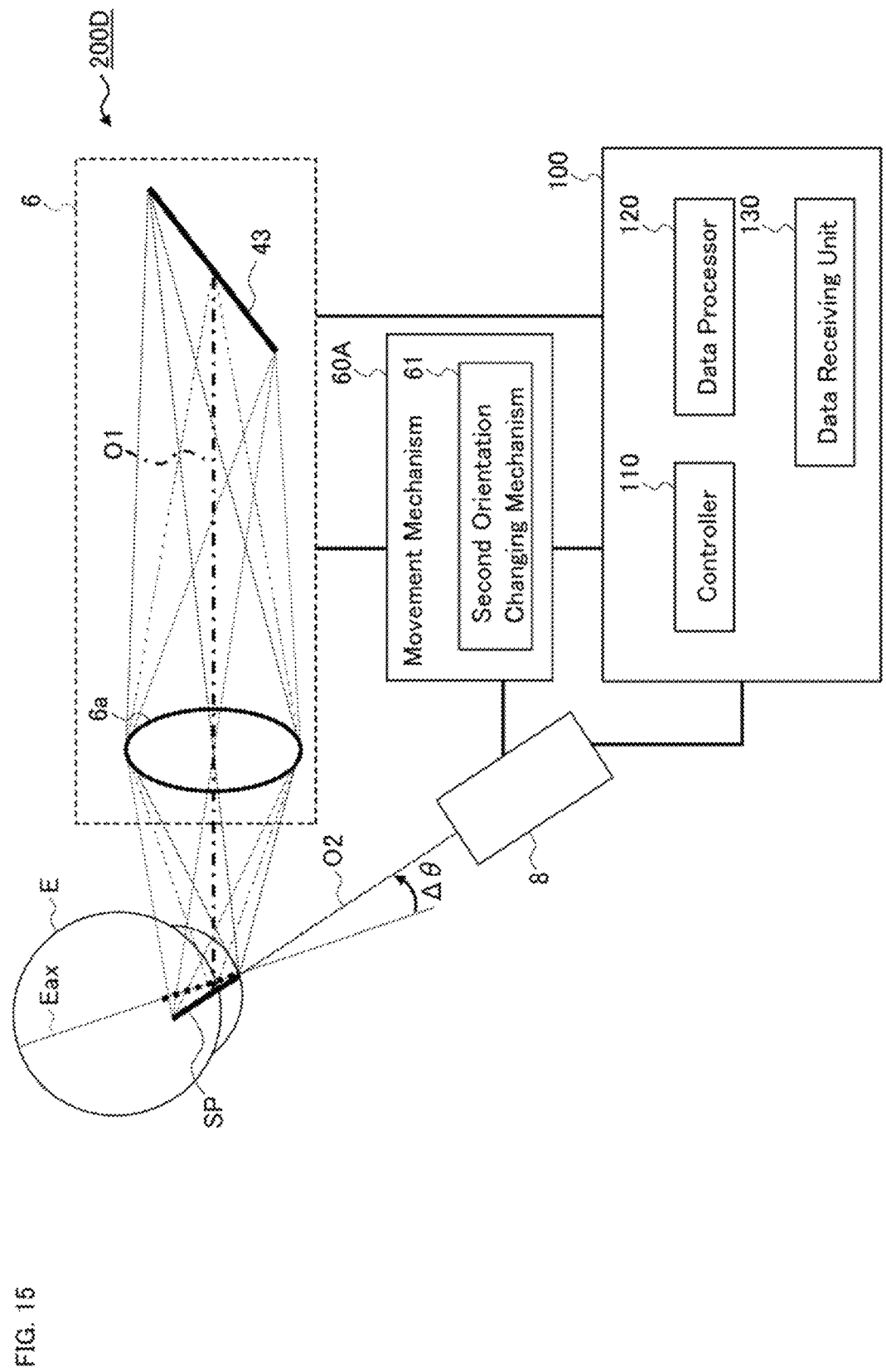
FIG. 15 is a schematic diagram illustrating the configuration of the slit lamp microscope according to the aspect example.
Figure 16:
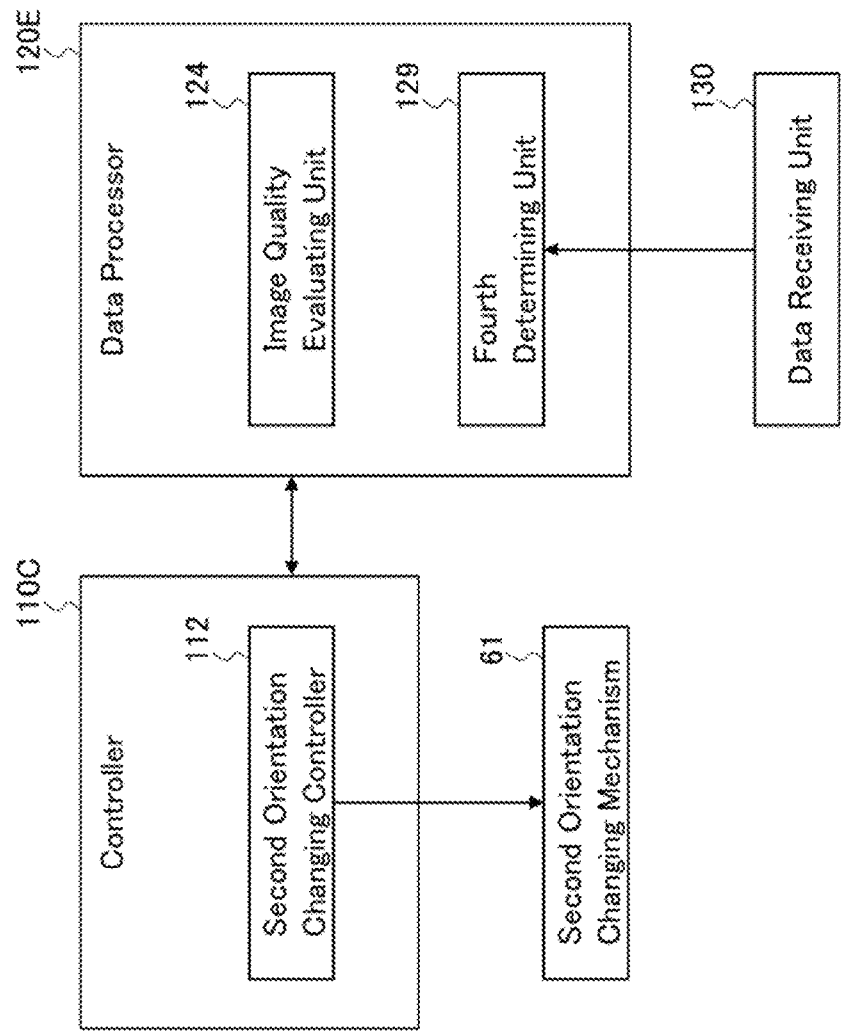
FIG. 16 is a schematic diagram illustrating the configuration of the slit lamp microscope according to the aspect example.

The slit lamp microscope according to the fifth aspect will be described. FIG. 15 and FIG. 16 show examples of the configuration of the slit lamp microscope 200D according to the present aspect.

As shown in FIG. 15, the slit lamp microscope 200D includes the photographing system 6, the illumination system 8, the movement mechanism 60A including the second orientation changing mechanism 61, and the computer 100, as with the slit lamp microscope 200C according to the fourth aspect.

The computer 100 includes the controller 110, the data processor 120, and the data receiver 130. The controller 110C and the data processor 120E illustrated in FIG. 16 are an example of the controller 110 of the present aspect and an example of the data processor 120 of the present aspect, respectively. The controller 110C includes the second orientation changing controller 112 similar to that of the fourth aspect. The data processor 120E includes the fourth determining processor 129 in addition to the image quality evaluating processor 124 similar to that of the second aspect. The data processor 120 (120E) of the present aspect may further include any of the three dimensional image constructing processor 121, the rendering processor 122, the analyzing processor 123, the measuring processor 125, the first determining processor 126, the second determining processor 127, and the third determining processor 128. Further, the slit lamp microscope 200D may include the first orientation changing mechanism 70, and may further include the first orientation changing controller 111. The data receiver 130 receives measurement data of the corneal curvature radius of the subject's eye E acquired in advance, as in the case with the third aspect.

The fourth determining processor 129 is configured to determine a target orientation of the illumination optical axis O2 based at least on the measurement data of the corneal curvature radius of the subject's eye E acquired by the data receiver 130. A target orientation and the determination method of a target orientation (such as a calculation method) may be the same as those of the third determining processor 128 according to the fourth aspect.

In the case of combining the information generation performed by the fourth determining processor 129 with the image quality evaluation performed by the image quality evaluating processor 124, for example, if the image quality evaluating processor 124 has determined that the image quality is insufficient, the target orientation may be determined by the fourth determining processor 129, and then the orientation of the illumination system 8 may be changed based on the target orientation determined.

Figure 17:
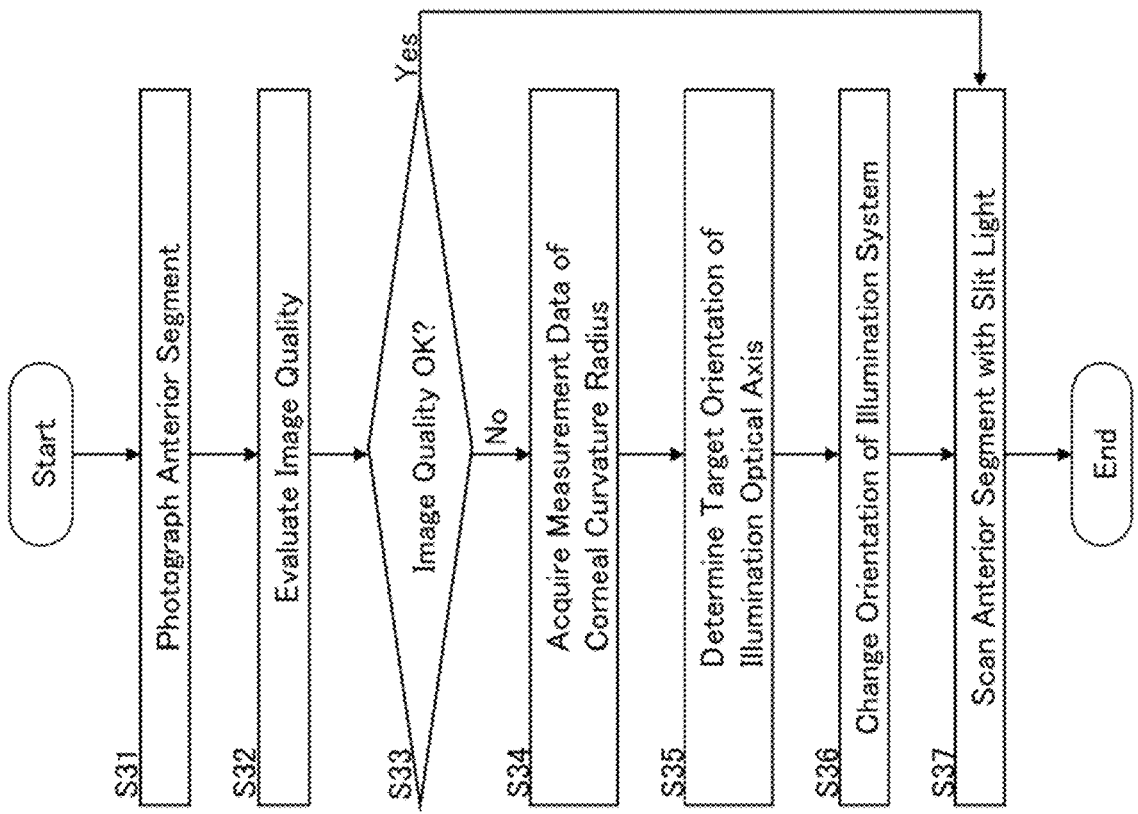
FIG. 17 is a flowchart illustrating the operation of the slit lamp microscope according to the aspect example.

An operation example of the slit lamp microscope 200D according to the present aspect will be described. FIG. 17 shows an example of the operation of the slit lamp microscope 200D. It is assumed that preparatory processes such as alignment have already been performed.

(S31: Photograph Anterior Segment)

First, the slit lamp microscope 200D performs photographing of the anterior segment of the subject's eye E, for example, in the same manner as in the step S1 of the second aspect.

(S32: Evaluate Image Quality)

The image quality evaluating processor 124 analyzes the image of the anterior segment acquired in the step S31 to evaluate the image quality thereof, for example, in the same manner as in the step S2 of the second aspect, (S33: Image Quality OK?)

In the case where the image quality evaluating processor 124 has determined in the step S32 that the image quality is sufficient (S33: Yes), the process proceeds to the step S37. On the other hand, in the case where the image quality evaluating processor 124 has determined in the step S32 that the image quality is not sufficient (S33: No), the process proceeds to the step S34.

(S34: Acquire Measurement Data of Corneal Curvature Radius)

In the case where the image quality evaluating processor 124 has determined that the image quality of the anterior segment image acquired in the step S31 is not sufficient (S33: No), the data receiver 130 receives measurement data of the corneal curvature radius of the subject's eye E acquired in advance.

(S35: Determine Target Orientation of Illumination Optical Axis)

The fourth determining processor 129 determines the target orientation of the illumination optical axis O2 based at least on the measurement data of the corneal curvature radius acquired in the step S34. The calculation here is performed, for example, in the same manner as in the step S25 of the fourth aspect.

(S36: Change Orientation of Illumination System)

For example, in the same manner as in the step S26 of the fourth aspect, the second orientation changing controller 112 executes control of the second orientation changing mechanism 61 to change the orientation of the illumination system 8 such that the orientation of the illumination optical axis O2 becomes to coincide with the target orientation determined in the step S35.

(S37: Scan Anterior Segment with Slit Light)

In response to the completion of the orientation changing of the illumination system 8 in the step S36, the slit lamp microscope 200D applies a scan with the slit light to the anterior segment of the subject's eye E, for example, in the same manner as in the step S7 of the second aspect. With this, for example, a clear image group covering an area at least from the anterior surface of the cornea to the posterior surface of the crystalline lens, can be obtained.

The data processor 120E (the three dimensional image constructing processor 121) may construct a three dimensional image based on this image group. Thereby, for example, a three dimensional image in which a three dimensional region at least from the anterior surface of the cornea to the posterior surface of the crystalline lens is expressed with high definition, can be obtained.

The data processor 120E (the rendering processor 122) may construct an arbitrary rendered image from the three dimensional image. This enables the user to observe a high quality image of a desired site or tissue of the subject's eye E.

The data processor 120E (the analyzing processor 123) may apply predetermined analysis processing to at least one of the plurality of images acquired in the step S37 or to an image generated by processing at least one of the plurality of images acquired in the step S37. As a result of this, desired analysis data regarding the subject's eye E can be obtained.

For example, in the case where the image quality of the image of the subject's eye E acquired in the step S37 is insufficient or like cases, the data processor 120E (the measuring processor 125) may perform measurement of the corneal curvature radius of the subject's eye E by carrying out either of the following steps: a step of analyzing at least one of the plurality of images acquired in the step S37 or an image generated by processing at least one of the plurality of images acquired in the step S37; or a process of analyzing an image obtained by another photographing performed after the step S37 or an image obtained by processing an image obtained by another photographing performed after the step S37. Based at least on the measurement data of the corneal curvature radius acquired in this way, the data processor 120E (the fourth determining processor 129) may determine a new target orientation of the illumination optical axis O2. In addition, the second orientation changing controller 112 may change the orientation of the illumination system 8 by controlling the second orientation changing mechanism 61 so as to change the orientation of the illumination optical axis O2 to the new target orientation determined. Such a series of processes is effective, for example, when there is a substantial difference between the measurement data of the corneal curvature radius acquired in the past and the corneal curvature radius at present.

In the present example, the completion of the orientation changing of the illumination system 8 (S36) triggers the scanning with the slit light (S37), but the trigger for the scanning with the slit light is not limited to this. For example, scanning with the slit light may be started in response to a user's instruction. In some aspect examples, the process may return to the step S31 in response to the completion of the orientation changing of the illumination system 8 (S36). If this is the case, the slit lamp microscope 200D may once again perform the photographing of the anterior segment, the evaluation of the image quality, and the change of the orientation of the illumination system 8. Alternatively, as in the case of the fourth aspect, the slit lamp microscope 200D may be configured to perform the photographing of the anterior segment, the evaluation of the image quality, the measurement of the corneal curvature radius, the determination of the target orientation, and the change of the orientation of the illumination system 8.

Effects

The effects of the slit lamp microscope according to some embodiment examples will be described.

A slit lamp microscope according to some aspect examples include an illumination system and a photographing system. The illumination system is configured to project slit light onto the anterior segment of a subject's eye. The photographing system includes an optical system and an image sensor. The optical system is configured to direct light coming from the anterior segment onto which the slit light is being projected. The image sensor has a light detecting surface and is configured to receive the light directed by the optical system with the light detecting surface. In addition, the subject plane, the principal plane of the optical system, and the light detecting surface are arranged in such a manner that the Scheimpflug condition is satisfied. Here, the subject plane includes the focal point of the illumination system in which the position of the focal point is shifted on account of the refractive index of a tissue of the anterior segment.

For example, the slit lamp microscope 200 includes the illumination system 8 and the photographing system 6. The illumination system 8 is configured to project slit light onto the anterior segment of the subject's eye. The photographing system 6 includes the optical system 6a and the image sensor 43. The optical system 6a is configured to direct light from the anterior segment onto which the slit light is being projected. The image sensor 43 includes a light detecting surface and is configured to receive the light directed by the optical system 6a with the light detecting surface. In addition, the subject plane SP, the principal plane of the optical system 6a, and the light detecting surface of the image sensor 43 are arranged so as to meet the Scheimpflug condition. Here, the subject plane SP includes the focal point of the illumination system 8 in which the position of the focal point is shifted on account of the refractive index of a tissue of the anterior segment.

The slit lamp microscope configured in this way is capable of obtaining an in-focus image of a region of the subject's eye corresponding to the subject plane. This is because the slit lamp microscope is configured in a manner that the subject plane, the principal plane of the optical system, and the light detecting surface satisfy the Scheimpflug condition, taking into account the positional shift (displacement) of the focal point of the illumination system attributable to the refractive index of the tissue of the anterior segment.

In some aspect examples, the shift angle of the subject plane on account of the refractive index of the tissue of the anterior segment may belong to the range between 3 degrees and 13 degrees, and further, may belong to the range between 6 degrees and 10 degrees. In some aspect examples, the shift angle of the subject plane on account of the refractive index of the tissue of the anterior segment may be determined based at least on a value of the corneal curvature radius and a value of the ocular refractive index according to an eye model.

In some aspect examples, the slit lamp microscope may further include a movement mechanism configured to move the illumination system and the photographing system. Furthermore, the photographing system may be configured to acquire a plurality of images of the anterior segment by performing repetitive photographing in parallel with the movement of the illumination system and the photographing system made by the movement mechanism.

For example, the slit lamp microscope 200 includes the movement mechanism 60 configured to move the illumination system 8 and the photographing system 6. The photographing system 6 may acquire a plurality of images of the anterior segment by performing repetitive photographing in parallel with the movement of the illumination system 8 and the photographing system 6 made by the movement mechanism 60. The mode or aspect of simultaneous execution of the movement of the illumination system 8 and the photographing system 6, and the repetitive photographing may be optional. In some aspect examples, the repetitive photographing may be performed in parallel with continuous movement of the illumination system 8 and the photographing system 6. Some other aspect examples perform photographing and movement of the illumination system 8 and the photographing system 6 in an alternate manner (one after the other).

According to such a slit lamp microscope, an in-focus image can be obtained for a region of the subject's eye corresponding to the range of the movement of the subject plane. This is because the slit lamp microscope is capable of performing repetitive photographing in parallel with the movement of the subject plane.

In some aspect examples, the slit lamp microscope may further include a three dimensional image constructing processor that is configured to construct a three dimensional image based on the plurality of images of the anterior segment acquired by the repetitive photographing executed in parallel with the movement of the illumination system and the photographing system.

For example, the slit lamp microscope 200 may construct, by the three dimensional image constructing processor 121, a three dimensional image based on the plurality of images of the anterior segment acquired by the repetitive photographing executed in parallel with the movement of the illumination system 8 and the photographing system 6.

According to such a slit lamp microscope, an in-focus three dimensional image can be obtained for a three dimensional region of the subject's eye corresponding to the range of the movement of the subject plane.

In some aspect examples, the slit lamp microscope may further include a rendering processor that is configured to construct a rendered image by applying rendering to the three dimensional image constructed by the three dimensional image constructing processor.

For example, the slit lamp microscope 200 may construct, by the rendering processor 122, a rendered image by applying rendering to the three dimensional image constructed by the three dimensional image constructing processor 121.

Such a slit lamp microscope is capable of constructing a desired rendered image from an in-focus three dimensional image of a three dimensional region of the subject's eye, and the user can observe the rendered image constructed in this way.

In some aspect examples, the slit lamp microscope may include an analyzing processor that is configured to apply analysis processing to at least one of the plurality of images of the anterior segment acquired by the repetitive photographing executed in parallel with the movement of the illumination system and the photographing system, or to an image (e.g., a three dimensional image, a rendered image, or other processed images) acquired by processing at least one of the plurality of images of the anterior segment acquired by the repetitive photographing executed in parallel with the movement of the illumination system and the photographing system.

For example, the slit lamp microscope 200 may apply analysis processing, by the analyzing processor 123, to at least one of the plurality of images of the anterior segment acquired by the repetitive photographing executed in parallel with the movement of the illumination system and the photographing system, or to an image generated by processing at least one of the plurality of images of the anterior segment acquired by the repetitive photographing executed in parallel with the movement of the illumination system and the photographing system.

Such a slit lamp microscope is capable of obtaining analysis data of highly accurate and highly precise since the slit lamp microscope can analyze a high quality image that is in focus on the subject plane.

In some aspect examples, the slit lamp microscope may further include the first orientation changing mechanism that is configured to change the orientation of the optical axis of the photographing system.

For example, the slit lamp microscope 200A (or 200B) includes the first orientation changing mechanism 70 that is configured to change the orientation of the optical axis O1 of the photographing system 6 (the photographing optical axis O1).

Such a slit lamp microscope is capable of performing adjustment of the orientation of the optical axis of the photographing system 6 on the basis of differences in the shapes of a tissue of individual eyes and in characteristics of individual eyes, in such a manner that the subject plane, the principal plane of the optical system, and the light detecting surface of the image sensor satisfy the Scheimpflug condition.

In some aspect examples, the first orientation changing mechanism may be configured to turn the photographing system about (around) a point (pivot) substantially coincident with the intersection between the subject plane and the optical axis of the photographing system.

For example, the first orientation changing mechanism 70 of the slit lamp microscope 200A (or 200B) is configured to turn the photographing system 6 about (around) the virtual turning axis SPa substantially located at the intersection between the subject plane SP and the optical axis O1 of the photographing system 6 (the photographing optical system O1).

Such a slit lamp microscope is capable of performing adjustment of the orientation of the photographing system in order that the Scheimpflug condition is satisfied, without having to change the position of the illumination system with respect to the cornea of the subject's eye.

In some aspect examples, the slit lamp microscope may further include an image quality evaluating processor and the first orientation changing controller. The image quality evaluating processor is configured to perform image quality evaluation by executing an analysis on an image of the subject's eye acquired by the photographing system. The first orientation changing controller is configured to executed control of the first orientation changing mechanism based at least on a result of the evaluation performed by the image quality evaluating processor.

For example, the slit lamp microscope 200A (or 200B) further includes the image quality evaluating processor 124 and the first orientation changing controller 111. The image quality evaluating processor 124 is configured to perform image quality evaluation on an image of the subject's eye E acquired by the photographing system 6, by executing an analysis on the image. The first orientation changing controller 111 is configured to execute control of the first orientation changing mechanism 70 based at least on a result of the evaluation performed by the image quality evaluating processor 124.

Such a slit lamp microscope is capable of perform the adjustment of the orientation of the photographing system so as to meet the Scheimpflug condition, on the basis of the image quality of the image acquired by actual measurement. For example, an image of low quality is obtained when the Scheimpflug condition is not met. In such a case, the present aspect can automatically perform the adjustment of the orientation of the photographing system.

In some aspect examples, the slit lamp microscope may further include a measuring processor and the first determining processor. The measuring processor is configured to perform measurement of a corneal curvature radius by executing an analysis on an image of the subject's eye acquired by the photographing system. The first determining processor is configured to determine a target orientation of the optical axis of the photographing system based at least on a result of the measurement performed by the measuring processor. Furthermore, the slit lamp microscope of the present aspect may be configured to change the orientation of the photographing system to the determined target orientation, by the first orientation changing mechanism.

For example, the slit lamp microscope 200A further includes the measuring processor 125 and the first determining processor 126. The measuring processor 125 is configured to perform measurement of a corneal curvature radius by executing an analysis on an image of the subject's eye E acquired by the photographing system 6. The first determining processor 126 is configured to determine a target orientation of the optical axis O1 of the photographing system 6 (the photographing optical axis O1) based at least on a result of the measurement performed by the measuring processor 125. The slit lamp microscope 200A may change the orientation of the photographing system 6 to the target orientation determined by the first determining processor 126, by the first orientation changing mechanism 70.

Such a slit lamp microscope is capable of performing the actual measurement of the corneal curvature radius of the subject's eye, the determination of the target orientation of the optical axis of the photographing system from the data obtained by the actual measurement, and then the adjustment of the orientation of the photographing system in order to satisfy the Scheimpflug condition. This allows the adjustment of the orientation of the photographing system to be performed with high accuracy and high precision.

In some aspect examples, the slit lamp microscope may further include a data receiver and the second determining processor. The data receiver is configured to receive measurement data of the corneal curvature radius of the subject's eye acquired in advance. The second determining processor is configured to determine a target orientation of the optical axis of the photographing system based at least on the measurement data received. In addition, the slit lamp microscope of the present aspect may be configured to change the orientation of the optical axis of the photographing system to the target orientation, by the first orientation changing mechanism.

For example, the slit lamp microscope 200B further includes the data receiver 130 and the second determining processor 127. The data receiver 127 is configured to receive measurement data of the corneal curvature radius of the subject's eye E acquired in advance. The second determining processor 127 is configured to determine a target orientation of the optical axis O1 of the photographing system 6 (the photographing optical axis O1) based at least on the measurement data received. By the first orientation changing mechanism 70, the slit lamp microscope 200B may change the orientation of the optical axis O1 of the photographing system 6 (the photographing optical axis O1) to the target orientation determined by the second determining processor 127.

According to such a slit lamp microscope, the target orientation of the optical axis of the photographing system can be determined from the actual measurement data of the corneal curvature radius of the subject's eye, and then the adjustment for the orientation of the photographing system in order to meet the Scheimpflug condition can be conducted. As a result, the adjustment for the orientation of the photographing system can be carried out with high accuracy and high precision.

Some aspect examples may be configured to start anterior segment photography with the photographing system in response to the event that the change of the orientation of the optical axis of the photographing system has been made by the first orientation changing mechanism.

For example, the slit lamp microscope 200A (or 200B) may start photographing of the anterior segment with the illumination system 8 and the photographing system 6, in response to the event that the change of the orientation of the optical axis O1 of the photographing system 6 (the photographing optical axis O1) has been made by the first orientation changing mechanism 70.

According to such a slit lamp microscope, the anterior segment photographing can be automatically performed after the orientation of the photographing system has been adjusted. Therefore, a situation or an event can be avoided in which anterior segment photographing is carried out in a state where the Scheimpflug condition is not met.

In some aspect examples, the slit lamp microscope may further include the second orientation changing mechanism configured to change the orientation of the optical axis of the illumination system.

For example, the slit lamp microscope 200C (or 200D) further includes the second orientation changing mechanism 61 that is configured to change the orientation of the optical axis O2 of the illumination system 8 (the illumination optical axis O2).

Such a slit lamp microscope is capable of performing adjustment of the orientation of the illumination system on the basis of differences in the shapes of a tissue of individual eyes and in characteristics of individual eyes, in such a manner that the subject plane, the principal plane of the optical system, and the light detecting surface of the image sensor satisfy the Scheimpflug condition.

In some aspect examples, the second orientation changing mechanism may be configured to turn the illumination optical axis about (around) the intersection of the cornea of the subject's eye and the illumination optical axis.

For example, the second orientation changing mechanism 61 of the slit lamp microscope 200C (or 200D) is configured to turn the illumination optical axis O2 (the illumination system 8) about (around) the intersection between the cornea of the subject's eye E and the illumination optical axis O2.

According to such a slit lamp microscope, the adjustment of the orientation of the illumination system in order to meet the Scheimpflug condition can be carried out without having to change the position of the photographing system with respect to the cornea of the subject's eye.

In some aspect examples, the slit lamp microscope may further include an image quality evaluating processor and the second orientation changing controller. The image quality evaluating processor is configured to evaluate image quality by analyzing an image of the subject's eye acquired by the photographing system. The second orientation changing controller is configured to control the second orientation changing mechanism based at least on a result of the evaluation performed by the image quality evaluating processor.

For example, the slit lamp microscope 200C (or 200D) further includes the image quality evaluating processor 124 and the second orientation changing controller 112. The image quality evaluating processor 124 is configured to perform image quality evaluation by executing an analysis on an image of the subject's eye E acquired by the photographing system 6. The second orientation changing controller 112 is configured to perform control of the second orientation changing mechanism 61 based at least on a result of the evaluation performed by the image quality evaluating processor 124.

According to such a slit lamp microscope, the adjustment of the orientation of the illumination system to meet the Scheimpflug condition can be performed on the basis of the image quality of the image actually obtained. For example, a low quality image is obtained when the Scheimpflug condition is not met. In such a case, adjustment for the orientation of the illumination system can be conducted automatically according to the present aspect.

In some aspect examples, the slit lamp microscope may further include a measuring processor and the third determining processor. The measuring processor is configured to measure the corneal curvature radius of the subject's eye by analyzing an image of the subject's eye acquired by the photographing system. The third determining processor is configured to determine a target orientation of the optical axis of the illumination system based at least on a result of the measurement performed by the measuring processor. In addition, the slit lamp microscope of the present aspect may be configured to change the orientation of the illumination optical axis to the determined target orientation, by the second orientation changing mechanism.

For example, the slit lamp microscope 200C further includes the measuring processor 125 and the third determining processor 128. The measuring processor 125 is configured to measure the corneal curvature radius of the subject's eye E by analyzing an image of the subject's eye E acquired by the photographing system 6. The third determining processor 128 is configured to determine a target orientation of the illumination optical axis O2 based at least on a result of the measurement performed by the measuring processor 125. The slit lamp microscope 200C may change the orientation of the illumination optical axis O2 to the determined target orientation, by the second orientation changing mechanism 61.

Such a slit lamp microscope is capable of performing the actual measurement of the corneal curvature radius of the subject's eye, the determination of the target orientation of the illumination optical axis from the data actually measured, and then the adjustment for the orientation of the illumination system in order to meet the Scheimpflug condition. As a result, the adjustment for the orientation of the illumination system can be conducted with high accuracy and high precision.

In some aspect examples, the slit lamp microscope may further include a data receiver and the fourth determining processor. The data receiver is configured to receive measurement data of the corneal curvature radius of the subject's eye acquired in advance. The fourth determining processor is configured to determine a target orientation of the illumination optical axis based at least on the measurement data received. Furthermore, the slit lamp microscope of the present aspect may be configured to change the orientation of the illumination optical axis to the determined target orientation, by the second orientation changing mechanism.

For example, the slit lamp microscope 200D further includes the data receiver 130 and the fourth determining processor 129. The data receiver 130 is configured to receive measurement data of the corneal curvature radius of the subject's eye E acquired in advance. The fourth determining processor 129 is configured to determine a target orientation of the illumination optical axis O2 based at least on the measurement data received. In addition, the slit lamp microscope 200D may change the orientation of the illumination optical axis O2 to the determined target orientation, by the second orientation changing mechanism 61.

Such a slit lamp microscope is capable of performing the determination of the target orientation of the illumination optical axis from the actual measurement data of the corneal curvature radius of the subject's eye, and then the adjustment for the orientation of the illumination system to meet the Scheimpflug condition. As a result, the adjustment for the illumination system can be conducted with high accuracy and high precision.

In some aspect examples, the photographing system may be configured to start photography of the anterior segment in response to the operation of changing the orientation of the illumination system made by the second orientation changing mechanism.

For example, the slit lamp microscope 200C (or 200D) may start anterior segment photographing with the illumination system and the photographing system, in response to the change of the orientation of the illumination system made by the second orientation changing mechanism.

According to such a slit lamp microscope, the anterior segment photographing can be automatically performed after the orientation of the illumination system has been adjusted. Therefore, a situation or an event can be avoided in which anterior segment photographing is carried out in a state where the Scheimpflug condition is not met.

<Sixth Aspect>

In the first to fifth aspects described above, it is assumed that the directions of all principal rays that are incident on the light detecting surface of the image sensor are the same. That is, it is assumed that the incident angles of all principal rays are equal. However, considering the fact that the light detecting surface is eccentrically and obliquely placed with respect to the optical axis of the optical system, strictly speaking, the incident angles of the principal rays respectively reaching different positions on the light detecting surface are different. The present aspect provides some configuration examples of the optical system in which such incident angle differences are taken into consideration.

Figure 18:
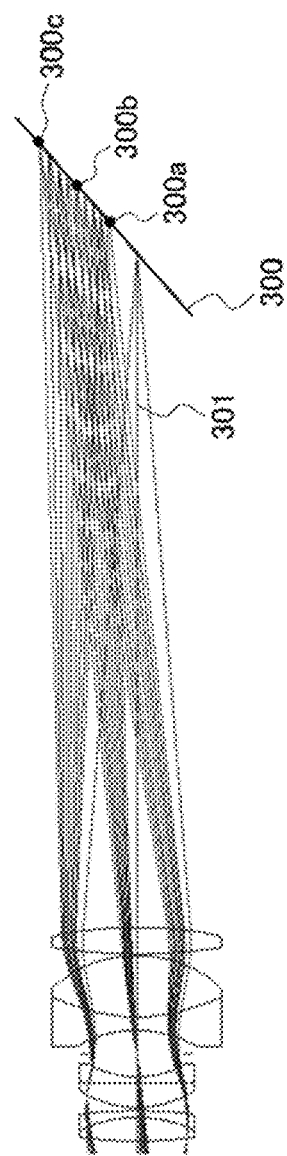
FIG. 18 is a schematic diagram for describing the slit lamp microscope according to the aspect example.

To begin with, an optical simulation carried out by the inventors of the present invention will be described. As shown in FIG. 18 as an example, the three positions 300*a*, 300*b*, and 300*c* on the light detecting surface of the image sensor 300 are considered. The reference character 301 denotes the optical axis of the optical system passing through the center of the diaphragm, or denotes the principal ray traveling along the optical axis of the optical system. The angle of view of an image obtained by the image sensor 300 is determined with reference to the optical axis 301 of the optical system. The position 300*b* corresponds to the center of the angle of view. The incident angle of the principal ray (the principal ray incident angle) at the position 300*b* is set to 38.11 degrees. Then, the principal ray incident angle at the position 300*a* (the lower end position of the angle of view) becomes 40.09 degrees, and the principal ray incident angle at the position 300*c* (the upper end position of the angle of view) becomes 36.06 degrees. From this example, it can be understood that the errors in the principal ray incident angles within the angle of view reach a maximum of approximately 4 degrees.

In the first to fifth aspects, typically, the principal ray incident angle of 38.11 degrees at the position 300*b* corresponding to the center of the angle of view, is applied to the entire angle of view. In contrast, the present aspect applies different principal ray incident angles to different positions in the angle of view, respectively. In other words, while the first to fifth aspects assume that the principal ray incident angles are uniform (constant), the present aspect considers the nonuniformity (nonconstancy) of the principal ray incident angles.

The results of such simulation will now be described. The positions on the light detecting surface respectively corresponding to the corneal apex, the anterior lens capsule, the lens nucleus, and the posterior lens capsule, will be referred to as the cornea corresponding position, the anterior capsule corresponding position, the nucleus corresponding position, and the posterior capsule corresponding position.

The distance between the cornea corresponding position and the anterior capsule corresponding position is set to 2.55 mm, the distance between the cornea corresponding position and the nucleus corresponding position is set to 4.91 mm, and the distance between the cornea corresponding position and the posterior capsule corresponding position is set to 7.14 mm.

Further, the design value (specification value) of the principal ray incident angle at the cornea corresponding position is set to 39.11 degrees, and its correction value of 39.11 degrees is obtained. The design value of the principal ray incident angle at the anterior capsule corresponding position is set to 38.61 degrees, and its correction value of 34.63 degrees is obtained. The design value of the principal ray incident angle at the nucleus corresponding position is set to 38.11 degrees, and its correction value of 31.64 degrees is obtained. The design value of the principal ray incident angle at the posterior capsule corresponding position is set to 37.61 degrees, and its correction value of 29.24 degrees was obtained.

The average of the above correction values is 33.65 degrees. In the present aspect, the optical system may be designed such that the principal ray incident angle with respect to the light detecting surface is set to the average value of 33.65 degrees.

Some examples of the calculation for determining correction values of principal ray incident angles will be described below. The reference character 400 in FIG. 19 denotes an eyeball (eye model). The eyeball 400 is positioned such that the corneal apex 401 is located at the origin of the xy coordinate system and the ocular optical axis coincides with the y-axis. The reference character 410 denotes the light detecting surface of the image sensor calculated in-air (referred to as the in-air image plane hereinafter). The in-air image plane 410 passes through the corneal apex 401. The reference character 420 denotes the principal ray. The reference character 421 denotes the imaging position of a light beam including the principal ray 420. Further, the angle formed by the principal ray 420 with respect to the y-axis is denoted by $\theta_1$, and the angle formed by the in-air image plane 410 with respect to the y-axis is denoted by $\theta_2$. Then, the incident angle $\theta$ of the principal ray 420 with respect to the in-air image plane 410 is represented by $\theta=\theta_1+\theta_2$.

Figure 19:
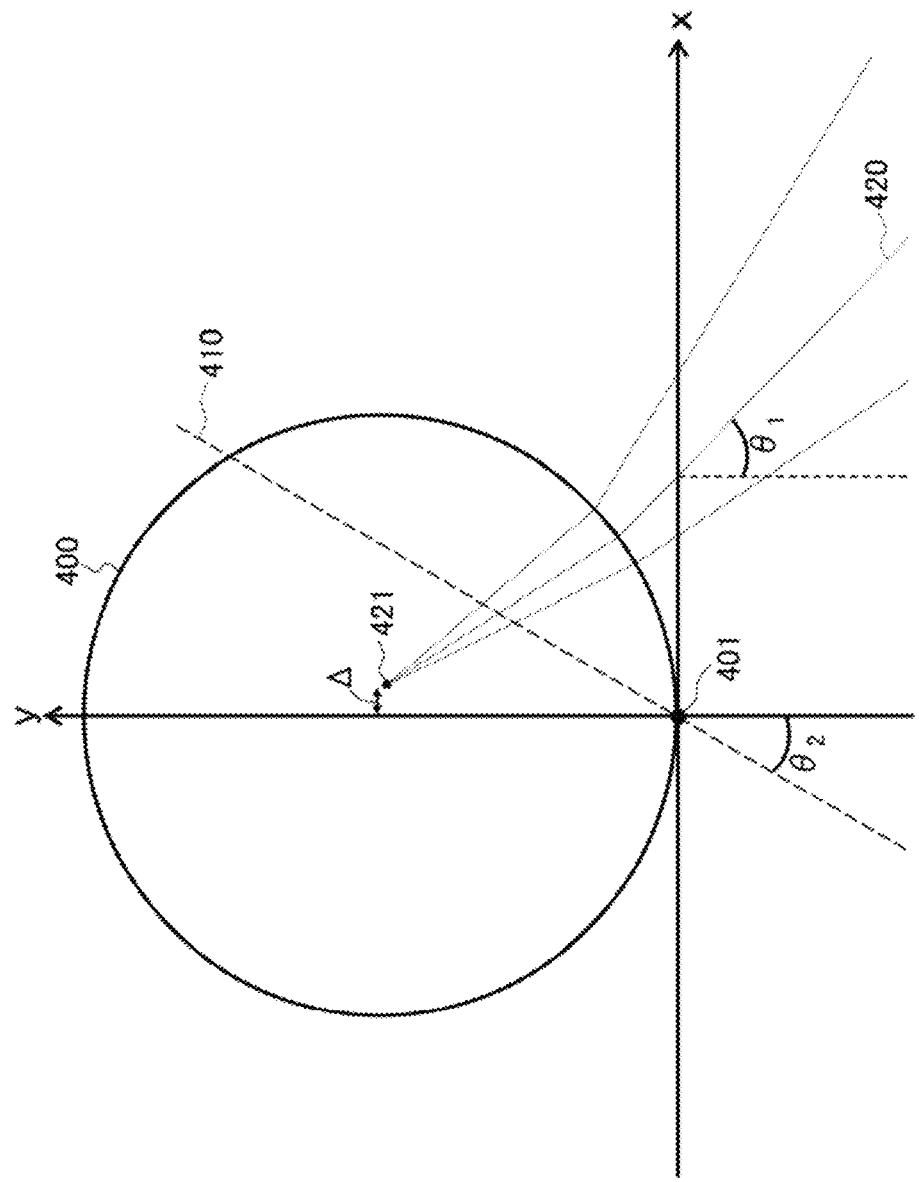
FIG. 19 is a schematic diagram for describing the slit lamp microscope according to the aspect example.

A correction value for the principal ray incident angle can be determined by finding a condition under which the optical axis of the image plane calculated in-eye becomes to coincide with the ocular optical axis (typically, with the illumination optical axis) in the model of FIG. 19. As can be seen from FIG. 19, the event that the optical axis of the image plane calculated in-eye coincides with the ocular optical axis is equivalent to the event that the imaging position 421 of the light beam including the principal ray 420 is positioned on the y-axis, which is also equivalent to the event that the positional shift Δ (displacement, deviation, error) in the x direction of the imaging position 421 with respect to the y-axis is set to zero (the positional shift Δ approaches zero: Δ→0).

For any principal ray incident angle $\theta$ ($\theta=\theta_1+\theta_2$), that is, for any position on the light detecting surface, the positional shift Δ can be obtained by the following four steps of calculation, for example.

(1) $\theta_1$ and $\theta_2$ are set. If one of $\theta_1$ and $\theta_2$ is set, the other is uniquely determined. For example, since $\theta$ is given, setting $\theta_1$ results in $\theta_2=\theta-\theta_1$.

(2) The intersection of the principal ray 420 and the in-air image plane 410 is determined without considering the refraction caused by the eyeball 400. In other words, the design position of the imaging position 421 is determined.

(3) The position where the principal ray 420 enters the eyeball 400 (cornea) is determined. In other words, the intersection of the surface of the eyeball 400 and the principal ray 420 is determined. Further, the incident angle and the output angle (exit angle, outgoing angle) of the principal ray 420 at the intersection are determined. That is, the refraction point and the refraction angle of the principal ray 420 are determined.

(4) The distance in the x direction between the (intraocular, in-eye) imaging position 421 and the ocular optical axis (the y-axis) is calculated, taking into consideration the refraction caused by the eyeball 400 (cornea). That is, the positional shift Δ described above is calculated.

The series of the above four calculation steps (1) to (4) is iterated while changing $\theta_1$ and $\theta_2$ until the magnitude of the positional shift Δ (the absolute value of the positional shift Δ) becomes less than a predetermined threshold value. Here, the threshold value may be set to 0.0001, for example. By such an iterative calculation, a correction value of the principal ray incident angle can be obtained for a state that the positional shift Δ is sufficiently small, for a state that the optical axis of the image plane and the ocular optical axis (the illumination optical axis) are substantially coincide with each other.

As an example of such calculation, calculation for the nucleus corresponding position will be described below. Note that $\theta=38.11107$ degrees at the nucleus corresponding position. Further, the corneal curvature radius of the eyeball 400 is set to r=7.72 mm, and the ocular refractive index is set to n=1.337.

(1) First, $\theta_1$ and $\theta_2$ are set. It is assumed that $\theta_2=5$ degrees. Then, the following is obtained: $\theta_1=\theta-\theta_2=38.11107-5=33.11107$ degrees.

(2) Next, the intersection of the principal ray 420 and the in-air image plane 410 is obtained, ignoring the refraction caused by the eyeball 400. In order to do this, first, an equation representing the in-air image plane 410 and an equation representing the principal ray 420 are obtained. Since the angle formed by the in-air image plane 410 and the x-axis is 90−$\theta_2$ degrees, the equation representing the in-air image plane 410 is y=(tan(90−$\theta_2$))x=(tan(90−5))x=11.43005x.

On the other hand, since the angle formed by the principal ray 420 and the x-axis is 90+$\theta_1$ degrees, the gradient (slope) of the principal ray 420 for the nucleus corresponding position is tan(90+$\theta_1$)=tan(90+33.11107)=−1.53335.

The y-intercept (y=$y_s$) of the principal ray 420 is calculated with reference to the design data of the optical system. The distance between the origin of the xy coordinate system (the corneal apex 401) and the intersection of the principal ray 420 and the in-air image plane 410, is denoted by $I_m$. For example, the distance $I_m$ for the cornea corresponding position is 0.00000 mm, the distance $I_m$ for the anterior capsule corresponding position is 1.81661 mm, the distance $I_m$ for the nucleus corresponding position is 3.68280 mm, and the distance $I_m$ for the posterior capsule corresponding position is 5.57288 mm.

Figure 20:
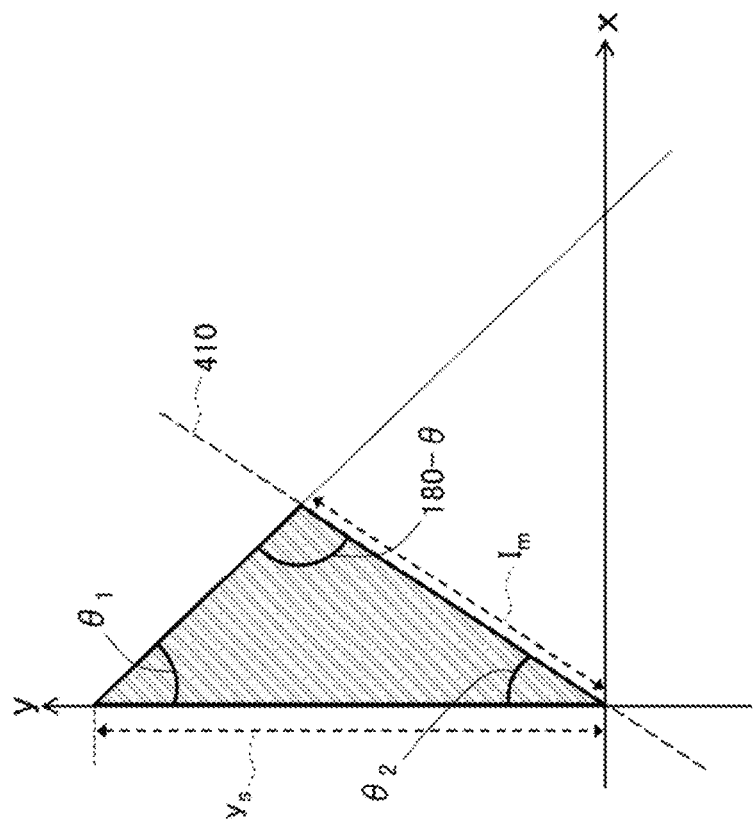
FIG. 20 is a schematic diagram for describing the slit lamp microscope according to the aspect example.

Moving now on to refer to FIG. 20. FIG. 20 shows a triangle with three vertices. The three vertices are the origin of the xy coordinate system (the corneal apex 401), the intersection of the principal ray 420 and the in-air image plane 410, and the y-intercept (the point where (x, y)=(0, $y_s$)). Applying the law of sines to the triangle, the value $y_s$ of the y-intercept for the nucleus corresponding position is calculated as follows: $y_s = I_m \times \sin(180-\theta)/\sin \theta_1 = 3.68280 \times \sin(180-38.11107)/\sin(38.11107) = 4.16096$.

From the above, the equation representing the principal ray 420 for the nucleus corresponding position is represented as the following: y=−1.53335x+4.16096. Therefore, the coordinates ($x_i$, $y_i$) of the intersection between the principal ray 420 and the in-air image plane 410 for the nucleus corresponding position are calculated by solving the system of equations consisting of the following equations: the equation representing the principal ray 420, y=−1.53335x+4.16096; and the equation representing the in-air image plane 410, y=11.43005x. Solving the system of equations results in ($x_i$, $y_i$)=(0.32098, 3.66879). This is the end of the calculation step (2).

(3) Next, the refraction point and the refraction angle of the principal ray 420 are obtained. The cornea of the eyeball 400 is represented by the following equation: $x^2 + (y-r)^2 = r^2 = 7.72^2$. The coordinates ($x_c$, $y_c$) of the intersection between the cornea and the principal ray 420 can be obtained by solving the system of equations consisting of the equation representing the cornea and the equation representing the principal ray 420. The coordinates ($x_c$, $y_c$) of the intersection for the nucleus corresponding position are as follows: ($x_c$, $y_c$)= (2.45277, 0.40001).

Subsequently, the incident angle and the output angle of the principal ray 420 at the intersection ($x_c$, $y_c$) are obtained. For that purpose, first, the gradient of the tangent line 430 of the eyeball 400 (cornea) at the intersection ($x_c$, $y_c$) is obtained. For the nucleus corresponding position, the gradient of the tangent line 430 corresponds to the x derivative at the intersection ($x_c$, $y_c$) of the curve $x^2+(y-r)^2=7.72^2$ representing the cornea. Differentiating the curve $x^2+(y-r)^2=7.72^2$ representing the cornea with respect to x gives the following equation: $y'=x/(r^2-x^2)^{1/2}$. By substituting the x coordinate $x_c$ of the intersection ($x_c$, $y_c$) into the equation of the x derivative, the gradient of the tangent line 430, $\tan \theta_y = 0.33508$ is obtained, and then $\theta_y = \arctan(0.33508) = 18.52486$ is obtained.

Figure 21:
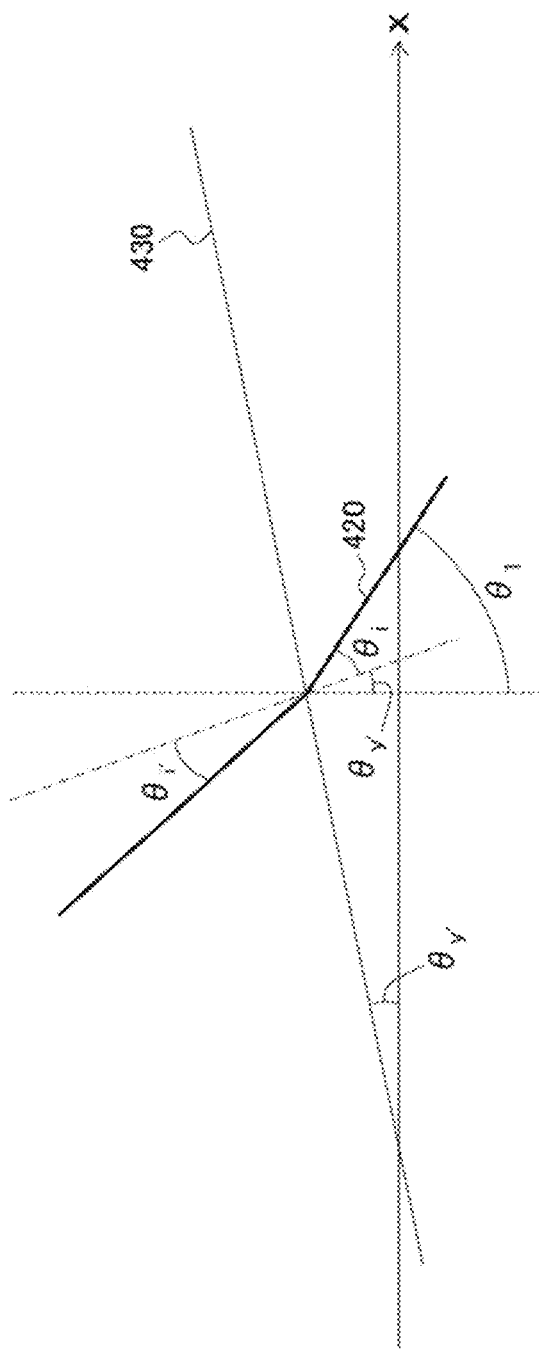
FIG. 21 is a schematic diagram for describing the slit lamp microscope according to the aspect example.

Further, as can be seen from FIG. 21, the incident angle $\theta_i$ of the principal ray 420 at the intersection ($x_c$, $y_c$) for the nucleus corresponding position is the following: $\theta_i = \theta_1 - \theta_y = 33.11107 - 18.52486 = 14.58621$.

In addition, the output angle $\theta_i'$ of the principal ray 420 at the intersection ($x_c$, $y_c$) for the nucleus corresponding position can be obtained using Snell's law: $\theta_i' = \arcsin((\sin \theta_i)/n) = \arcsin((\sin(14.58621))/1.337) = 10.85705$. This is the end of the calculation step (3).

(4) Finally, the distance (the positional shift Δ) in the x direction between the ocular optical axis and the imaging position 421 determined by taking into account the refraction caused by the eyeball 400, is obtained. For that purpose, first, the intersection of the principal ray 420 and the x-axis is obtained. Puting y=0 in the equation y=−1.53335x+4.16096 representing the principal ray 420 for the nucleus corresponding position, the intersection ($x_0$, $y_0$) between the principal ray 420 and the x-axis is obtained as follows: ($x_0$, $y_0$)= (2.71364, 0).

Next, the image forming position of the incident light beam when ignoring the refraction caused by the eyeball 400, is determined. That is, the distance between the x-axis and the in-air image plane 410 when ignoring the refraction caused by the eyeball 400, is obtained. The triangle is considered which defined by the following three points as vertices: the intersection of the principal ray 420 and the x-axis; the intersection of the principal ray 420 and the in-air image plane 410; and the foot of the perpendicular that passes through the intersection of the principal ray 420 and the in-air image plane 410 and that is perpendicular to the x-axis. By applying the Pythagorean theorem to this triangle, the distance L between the x-axis and the in-air image plane 410 is determined as follows: $L=((x_0-x_i)^2+(y_0-y_i)^2)^{1/2} = ((2.71364-0.32098)^2+(0-3.66879)^2)^{1/2}=4.38005$.

Figure 22:
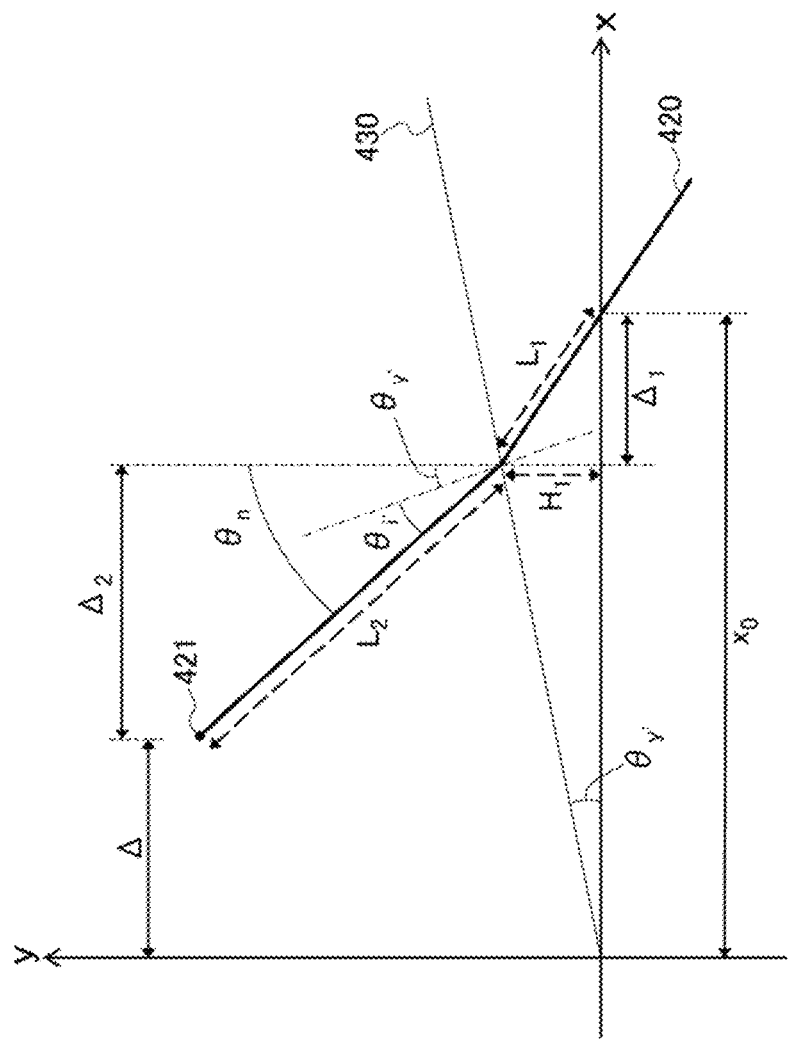
FIG. 22 is a schematic diagram for describing the slit lamp microscope according to the aspect example.

Further, referring now to FIG. 22, the distance $\Delta_1$ by which the principal ray 420 travels in the x direction from the time point when the principal ray 420 passes through the x-axis to the time point when the principal ray 420 is incident on the eyeball 400, that is, the x component $\Delta_1$ of the distance between the position at which the principal ray 420 intersects the x-axis and the position at which the principal ray 420 intersects the eyeball 400, can be obtained by the following equation: $\Delta_1 = |x_c - x_0| = |2.45277 - 2.71364| = 0.26087$.

Similarly, the distance $H_1$ by which the principal ray 420 travels in the y direction from the time point when the principal ray 420 passes through the x-axis to the time point when the principal ray 420 is incident on the eyeball 400, that is, the y component $H_1$ of the distance between the position at which the principal ray 420 intersects the x-axis and the position at which the principal ray 420 intersects the eyeball 400 is obtained as follows: $H_1 = |y_c - y_0| = 0.40001$.

Therefore, the distance $L_1$ by which the principal ray 420 travels from the time point when the principal ray 420 passes through the x-axis to the time point when the principal ray 420 is incident on the eyeball 400, that is, the distance $L_1$ between the position at which the principal ray 420 intersects the x-axis and the position at which the principal ray 420 intersects the eyeball 400 is obtained by the following calculation: $L_1 = (\Delta_1^2 + H_1^2)^{1/2} = (0.26087^2 + 0.40001^2)^{1/2} = 0.47755$.

Thus, the length $L_2$ of the principal ray 420 in the eyeball 400, that is, the distance $L_2$ between the point at which the principal ray 420 intersects the eyeball 400 (cornea) and the imaging position 421, can be obtained by multiplying the difference between the distance L and the distance $L_1$ by the ocular refractive index n as follows: $L_2 = (L - L_1) \times n = (4.38005 - 0.47755) \times 1.337 = 5.21764$. Here, the distance L is the distance between the x-axis and the in-air image plane 410 when ignoring the refraction, and the distance $L_1$ is the distance by which the principal ray 420 travels from the time at which the principal ray 420 passes through the x-axis to the time at which the principal ray 420 is incident on the eyeball 400.

The angle $\theta_n$ formed by the principal ray 420 in the eyeball 400 with respect to the optical axis of the eyeball 400 (the y-axis) can be obtained by the following equation: $\theta_n = \theta_y + \theta_i' = 18.52486 + 10.85705 = 29.38191$.

Furthermore, the distance $\Delta_2$ by which the principal ray 420 travels in the x direction in the eyeball 400 can be obtained by the following calculation: $L_2 \times \sin \theta_n = 5.21764 \times \sin(29.38191) = 2.55992$.

Therefore, the distance $\Delta$ (the target positional shift $\Delta$) in the x direction between the ocular optical axis (the y-axis) and the imaging position 421 determined by taking into account the refraction caused by the eyeball 400 (the subject's eye), can be obtained by the following equation: $\Delta = x_0 - \Delta_1 - \Delta_2 = 2.71364 - 0.26087 - 2.55992 = 0.10715$.

The magnitude of the positional shift $\Delta$ thus obtained (the absolute value of the positional shift $\Delta$) is compared with a predetermined threshold value (e.g., 0.0001). In the present example, the positional shift $\Delta = 0.10715 > 0.0001$. Therefore, $\theta_1$ and $\theta_2$ are changed, and the four calculation steps (1) to (4) are executed again. This iterative calculation is repeated until the magnitude of the positional shift $\Delta$ becomes less than the threshold value. Such iterative calculation gives a correction value of the incident angle of the principal ray 420 when the positional shift $\Delta$ is sufficiently small, that is, when the optical axis of the image plane substantially coincides with the ocular optical axis (the illumination optical axis).

The following table shows the values of various parameters for the cornea corresponding position, the anterior capsule corresponding position, the nucleus corresponding position, and the posterior capsule corresponding position, which have been determined to meet the condition that the positional shift $\Delta < 0.0001$ by using the calculation described above.

TABLE 1

| | Cornea | Anterior capsule | Nucleus | Posterior capsule |
|---|---|---|---|---|
| $\theta_1$ | 39.11025 | 34.62912 | 31.63867 | 29.23846 |
| $\theta_2$ | 0 | 3.98356 | 6.47240 | 8.36637 |
| $y_s$ | 0 | 1.99496 | 4.33311 | 6.96216 |
| $x_i$ | 0 | 0.12620 | 0.41514 | 0.81087 |
| $y_i$ | 0 | 1.81222 | 3.65933 | 5.51357 |
| $x_c$ | 0 | 1.30143 | 2.42834 | 3.44346 |
| $y_c$ | 0 | 0.11049 | 0.39186 | 0.81052 |
| $\theta_{y'}$ | 0 | 9.70517 | 18.33375 | 26.49017 |
| $\theta_i$ | 39.11025 | 24.92395 | 13.30492 | 2.74829 |
| $\theta_{i'}$ | 28.15208 | 18.37255 | 9.91149 | 2.05522 |
| $x_0$ | 0 | 1.37773 | 2.66978 | 3.89716 |
| L | 0 | 2.20238 | 4.29815 | 6.31860 |
| $\Delta_1$ | 0 | 0.07630 | 0.24144 | 0.45370 |
| $L_1$ | 0 | 0.13427 | 0.46027 | 0.92886 |
| $L_2$ | 0 | 2.76505 | 5.13124 | 7.20608 |
| $\theta_n$ | 28.15208 | 28.07772 | 28.24524 | 28.54539 |
| $\Delta_2$ | 0 | 1.30143 | 2.42834 | 3.44346 |
| $\Delta$ | 0 | 0.00000002 | 0.00000035 | 0.00000054 |

Based on the knowledge obtained by the above simulation, the shift angle of the subject plane on account of the refractive index of the subject's eye E may be determined in the following manner.

First, the shift angle of the subject plane on account of the refractive index of the subject's eye E may be determined based at least on the angle formed by the optical axis of the illumination system 8 (the illumination optical axis O2) and the optical axis of the photographing system 6 (the photographing optical axis O1).

Here, the angle formed by the illumination optical axis O2 and the photographing optical axis O1 may be set to a value greater than 0 degrees and not exceeding 60 degrees. Note that the Scheimpflug principle requires that the angle range does not include 0 degrees. On the other hand, the maximum value of the angle range, namely 60 degrees, is a finding obtained from the examination on anterior segment photography using the Scheimpflug principle conducted by the inventors of the present invention. The maximum value of the angle range, namely 60 degrees, is the limit value of the angle formed by the illumination optical axis O2 and the photographing optical axis O1 in order to implement suitable acquisition of images of the area from the cornea to the crystalline lens.

The shift angle of the subject plane on account of the refractive index of the subject's eye E may be determined based at least on the corneal curvature radius in addition to the angle formed by the illumination optical axis O2 and the photographing optical axis O1.

Here, a value of the corneal curvature radius may be set based on an eye model. This eye model may be any of, for example, the Gullstrand eye model, the Navarro eye model, the Liou-Brennan eye model, the Badal eye model, the Arizona eye model, the Indiana eye model, any standardized eye model, and any eye model equivalent to any of the above eye models.

Typically, as in the calculation example described above, the value of the corneal curvature radius may be set to a value, for example, belonging to the range of 7.7 mm±0.5 mm according to the Gullstrand eye model.

The shift angle of the subject plane on account of the refractive index of the subject's eye E may be determined based at least on the ocular refractive index in addition to the angle formed by the illumination optical axis O2 and the photographing optical axis O1.

Here, a value of the ocular refractive index may be determined based on a predetermined eye model. This eye model may be any of, for example, the Gullstrand eye model, the Navarro eye model, the Liou-Brennan eye model, the Badal eye model, the Arizona eye model, the Indiana eye model, any standardized eye model, and any eye model equivalent to any of the above eye models.

Typically, as in the calculation example described above, the value of the ocular refractive index may be set to a value, for example, belonging to a range of 1.336±0.001 according to the Gullstrand eye model.

The shift angle of the subject plane on account of the refractive index of the subject's eye E may be determined based at least on the corneal curvature radius and the ocular refractive index in addition to the angle formed by the illumination optical axis O2 and the photographing optical axis O1.

Here, each of a value of the corneal curvature radius and a value of the ocular refractive index may be determined based on a predetermined eye model as described above. Typically, as in the calculation example described above, according to the Gullstrand eye model, the value of the corneal curvature radius may be set to a value belonging to the range of 7.7 mm±0.5 mm, as well as the value of the ocular refractive index may be set to a value belonging to the range of 1.336±0.001.

In the case where the value of the corneal curvature radius is set to a value belonging to the range of 7.7 mm±0.5 mm, the value of the ocular refractive index is set to a value belonging to the range of 1.336±0.001, and further, the angle formed by the illumination optical axis O2 and the photographing optical axis O1 is set to a value greater than 0 degrees and not exceeding 60 degrees, the shift angle of the subject plane on account of the refractive index of the subject's eye E may be set to a value greater than 0 degrees and not exceeding 11.09 degrees. Here, the condition that the shift angle of the subject plane is greater than 0 degrees is a natural consequence derived from the Scheimpflug principle. Furthermore, the maximum value of 11.09 degrees in the range of the shift angle is a value obtained by executing the calculation steps (1) to (4) under the following conditions: the corneal curvature radius r=7.2 mm; the ocular refractive index n=1.337; the angle θ formed by the illumination optical axis O2 and the photographing optical axis O1, θ=θ$_1$+θ$_2$=60 degrees; and the positional shift Δ<0.0001.

According to the present aspect, the deviation from the Scheimpflug condition attributable to the difference between the refractive index inside the subject's eye and the refractive index outside the subject's eye, can be avoided with higher precision and higher accuracy as compared with the first to fifth aspects.

The present aspect may be combined with any one or two or more of the first to fifth aspects. In addition, any known technology or technique may be combined with an embodiment that include at least part of the present aspect. Further, modifications (e.g., additions, replacements, substitutions, etc.) may also be made on the basis of any known technology or technique.

<Other Matters and Items>

The aspects described above are merely examples. Therefore, any modifications (e.g., omissions, replacements, substitutions, additions, etc.) may be made within the scope of the gist of the present invention.

For example, in some aspect examples, remote operations of a slit lamp microscope may be possible. For that purpose, the slit lamp microscope may include a receiver, a controller, and a transmitter, for example.

The receiver of the slit lamp microscope of the present aspect receives an instruction from the first apparatus via a communication line. The receiver includes at least part of the communication device described above. The first apparatus includes, for example, an operation device for inputting an instruction for remotely operating the slit lamp microscope, a computer that receives the instruction input using the operation device, and a transmission device that transmits the received instruction to the slit lamp microscope.

The controller of the slit lamp microscope of the present aspect controls at least the illumination system and the photographing system in accordance with the instructions received by the receiver. With this, acquisition of images of the subject's eye is carried out. The controller includes at least part of the computer 100.

The transmitter of the slit lamp microscope of the present aspect transmits images of the subject's eye acquired in accordance with the instruction, or transmits data (e.g., images, analysis data, etc.) obtained by processing the images, to the second apparatus via a communication line. The transmitter includes at least part of the communication device described above. The second apparatus includes at least a receiving device that receives the images or the data sent from the slit lamp microscope. The second apparatus may further include a storage device that stores the images or the data received, and a computer that processes the images or the data received, for example.

A light field camera may be employed as an imaging device instead of the configuration that is capable of changing the orientation of the optical axis of the photographing system like the slit lamp microscopes 200A and 200B. If this is the case, optical space image processing may be applied to an image obtained by this imaging device to generate an image in which at least the entire subject plane is in focus.

A program may be configured which causes a computer to execute one or more processes according to any one of some aspect examples or according to any combination of any two or more of some aspect examples. Further, a program may be configured which causes a computer to execute one or more processes realized by applying any modifications within the scope of the gist of the present invention to any one of some aspect examples or to any combination of any two or more of some aspect examples.

In addition, it is possible to create a non-transitory computer readable recording medium that stores one or more of the above programs. The non-transitory recording medium may be in any form, such as a magnetic disk, an optical disk, a magneto-optical disk, and a semiconductor memory.

The present invention includes a method implemented by any one of some aspect examples or by any combination of any two or more of some aspect examples. In addition, the present invention includes a method implemented by applying any modifications within the scope of the gist of the present invention to any one of some aspect examples or to any combination of any two or more of some aspect examples.

EXPLANATION OF REFERENCE CHARACTERS

200, 200A, 200B, 200C, 200D Slit lamp microscope
6 Photographing system
6a Optical system
8 Illumination system
O2 Illumination optical axis
43 Image sensor
60 Movement mechanism
61 Second orientation changing mechanism
70 First orientation changing mechanism
100 Computer
111 First orientation changing controller
112 Second orientation changing controller
121 Three dimensional image constructing processor
122 Rendering processor
123 Analyzing processor
124 Image quality evaluating processor
125 Measuring processor
126 First determining processor
127 Second determining processor
128 Third determining processor
129 Fourth determining processor
130 Data receiver

What is claimed is:

1. A slit lamp microscope comprising:
   an illumination system configured to project slit light onto an anterior segment of a subject's eye;
   a photographing system that includes an optical system and an image sensor, the optical system being configured to direct light from the anterior segment onto which the slit light is being projected, and the image sensor including a light detecting surface that receives the light directed by the optical system;
   a refractive index memory configured to store a refractive index of the anterior segment of the subject's eye;
   a movement mechanism configured to move at least one of the illumination system and the photographing system; and
   a controller configured to control the movement mechanism to move the at least one of the illumination system and the photographing system to shift a focal point of the illumination system by a shift angle determined based on the refractive index so that a subject plane including the shifted focal point, a principal plane of the optical system, and the light detecting surface are arranged so as to satisfy a Scheimpflug condition.

2. The slit lamp microscope of claim 1, further comprising the movement mechanism configured to move both the illumination system and the photographing system, wherein the photographing system is configured to acquire a plurality of images of the anterior segment by repetitively performing photography in parallel with movement of the illumination system and the photographing system by the movement mechanism.

3. The slit lamp microscope of claim 2, further comprising a three dimensional image constructing processor configured to construct a three dimensional image based on the plurality of images.

4. The slit lamp microscope of claim 3, further comprising a rendering processor configured to construct a rendered image by applying rendering to the three dimensional image.

5. The slit lamp microscope of claim 2, further comprising an analyzing processor configured to apply predetermined analysis processing to at least one of the plurality of images or an image generated by processing at least one of the plurality of images.

6. The slit lamp microscope of claim 1, wherein the shift angle belongs to a range of 3 to 13 degrees.

7. The slit lamp microscope of claim 6, wherein the shift angle belongs to a range of 6 to 10 degrees.

8. A slit lamp microscope comprising:
an illumination system configured to project slit light onto an anterior segment of a subject's eye;
a photographing system that includes an optical system and an image sensor, the optical system being configured to direct light from the anterior segment onto which the slit light is being projected, and the image sensor including a light detecting surface that receives the light directed by the optical system;
an optical axis angle measuring instrument configured to measure an angle formed by an optical axis of the illumination system and an optical axis of the photographing system;
a movement mechanism configured to move at least one of the illumination system and the photographing system; and
a controller configured to control the movement mechanism to move the at least one of the illumination system and the photographing system to shift a focal point of the illumination system by a shift angle determined based on the angle so that a subject plane including the shifted focal point, a principal plane of the optical system, and the light detecting surface are arranged so as to satisfy a Scheimpflug condition.

9. A slit lamp microscope comprising:
an illumination system configured to project slit light onto an anterior segment of a subject's eye;
a photographing system that includes an optical system and an image sensor, the optical system being configured to direct light from the anterior segment onto which the slit light is being projected, and the image sensor including a light detecting surface that receives the light directed by the optical system;
an optical axis angle measuring instrument configured to measure an angle formed by an optical axis of the illumination system and an optical axis of the photographing system;
a corneal curvature radius measuring instrument configured to measure a corneal curvature radius of the anterior segment of the subject's eye;
a movement mechanism configured to move at least one of the illumination system and the photographing system; and
a controller configured to control the movement mechanism to move the at least one of the illumination system and the photographing system to shift a focal point of the illumination system by a shift angle determined based on the angle and the corneal curvature radius so that a subject plane including the shifted focal point, a principal plane of the optical system, and the light detecting surface are arranged so as to satisfy a Scheimpflug condition.

10. A slit lamp microscope comprising:
an illumination system configured to project slit light onto an anterior segment of a subject's eye;
a photographing system that includes an optical system and an image sensor, the optical system being configured to direct light from the anterior segment onto which the slit light is being projected, and the image sensor including a light detecting surface that receives the light directed by the optical system;
an optical axis angle measuring instrument configured to measure an angle formed by an optical axis of the illumination system and an optical axis of the photographing system;
an ocular refractive index measuring instrument configured to measure an ocular refractive index of the subject's eye;
a movement mechanism configured to move at least one of the illumination system and the photographing system; and
a controller configured to control the movement mechanism to move the at least one of the illumination system and the photographing system to shift a focal point of the illumination system by a shift angle determined based on the angle and the ocular refractive index so that a subject plane including the shifted focal point, a principal plane of the optical system, and the light detecting surface are arranged so as to satisfy a Scheimpflug condition.

11. A slit lamp microscope comprising:
an illumination system configured to project slit light onto an anterior segment of a subject's eye;
a photographing system that includes an optical system and an image sensor, the optical system being configured to direct light from the anterior segment onto which the slit light is being projected, and the image sensor including a light detecting surface that receives the light directed by the optical system;
an optical axis angle measuring instrument configured to measure an angle formed by an optical axis of the illumination system and an optical axis of the photographing system;
a corneal curvature radius measuring instrument configured to measure a corneal curvature radius of the anterior segment of the subject's eye;
an ocular refractive index measuring instrument configured to measure an ocular refractive index of the subject's eye;
a movement mechanism configured to move at least one of the illumination system and the photographing system; and
a controller configured to control the movement mechanism to move the at least one of the illumination system and the photographing system to shift a focal point of the illumination system by a shift angle determined based on the angle, the corneal curvature radius, and the ocular refractive index so that a subject plane including the shifted focal point, a principal plane of the optical system, and the light detecting surface are arranged so as to satisfy a Scheimpflug condition.

* * * * *